(12) United States Patent
Singamaneni et al.

(10) Patent No.: US 10,744,461 B2
(45) Date of Patent: Aug. 18, 2020

(54) ULTRAFILTRATION MEMBRANE BASED ON BACTERIAL NANOCELLULOSE AND GRAPHENE OXIDE

(71) Applicants: Srikanth Singamaneni, St. Louis, MO (US); Young-Shin Jun, St. Louis, MO (US); Qisheng Jiang, St. Louis, MO (US); Deoukchen Ghim, St. Louis, MO (US)

(72) Inventors: Srikanth Singamaneni, St. Louis, MO (US); Young-Shin Jun, St. Louis, MO (US); Qisheng Jiang, St. Louis, MO (US); Deoukchen Ghim, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 16/276,106

(22) Filed: Feb. 14, 2019

(65) Prior Publication Data
US 2019/0247793 A1    Aug. 15, 2019

Related U.S. Application Data

(63) Continuation-in-part of application No. 15/653,942, filed on Jul. 19, 2017.

(60) Provisional application No. 62/426,979, filed on Nov. 28, 2016, provisional application No. 62/369,934, filed on Aug. 2, 2016.

(51) Int. Cl.
| | |
|---|---|
| *B01D 71/10* | (2006.01) |
| *B01D 61/14* | (2006.01) |
| *B01D 71/02* | (2006.01) |
| *C02F 1/44* | (2006.01) |
| *B01D 67/00* | (2006.01) |
| *C12N 1/22* | (2006.01) |
| *C12N 1/20* | (2006.01) |
| *C02F 1/14* | (2006.01) |
| *F24S 70/10* | (2018.01) |
| *B32B 1/00* | (2006.01) |
| *B01D 71/08* | (2006.01) |
| *C02F 1/10* | (2006.01) |
| *B01D 69/14* | (2006.01) |
| *B01D 65/08* | (2006.01) |
| *B01D 69/06* | (2006.01) |
| *F24S 80/00* | (2018.01) |

(52) U.S. Cl.
CPC .......... *B01D 61/145* (2013.01); *B01D 65/08* (2013.01); *B01D 67/0079* (2013.01); *B01D 67/0095* (2013.01); *B01D 69/148* (2013.01); *B01D 71/024* (2013.01); *B01D 71/08* (2013.01); *B01D 71/10* (2013.01); *B32B 1/00* (2013.01); *C02F 1/10* (2013.01); *C02F 1/14* (2013.01); *C02F 1/444* (2013.01); *C12N 1/20* (2013.01); *C12N 1/22* (2013.01); *F24S 70/10* (2018.05); *B01D 69/06* (2013.01); *B01D 2323/40* (2013.01); *B01D 2325/02* (2013.01); *B01D 2325/48* (2013.01); *C02F 2303/20* (2013.01); *F24S 2080/017* (2018.05); *Y02A 20/212* (2018.01); *Y02P 20/134* (2015.11); *Y02P 20/136* (2015.11); *Y02P 20/59* (2015.11); *Y02W 10/37* (2015.05)

(58) Field of Classification Search
None
See application file for complete search history.

(56) References Cited

U.S. PATENT DOCUMENTS

| | | |
|---|---|---|
| 2015/0072133 A1 | 3/2015 | Ghasemi et al. |
| 2015/0141711 A1 | 5/2015 | Chu et al. |
| 2016/0084532 A1 | 3/2016 | Tsutsui et al. |
| 2016/0192501 A1 | 6/2016 | Yan et al. |
| 2016/0199767 A1 | 7/2016 | Agrahari et al. |
| 2016/0235347 A1 | 8/2016 | Baig et al. |
| 2016/0319176 A1 | 11/2016 | Konogaya et al. |
| 2017/0142975 A1 | 5/2017 | Shi et al. |

FOREIGN PATENT DOCUMENTS

| | | |
|---|---|---|
| WO | 2013076372 A1 | 5/2013 |
| WO | 2016071573 A1 | 5/2016 |

OTHER PUBLICATIONS

Alagarasi A., "Introduction to nanomaterials," in Nanomaterials, Viswanathan B. (ed.), Alpha Science/Narosa Publishing House, 2009, Chapter 1, pp. 1-76.
Classification of Nanomaterials, The Four Main Types of Intentionally Produced Nanomaterials, sponsored by U.S. Environmental Protection Agency, Mar. 1, 2007, http://www.azonano.com/article.aspx?ArticleID=1872, 4 pages.
Ghasemi et al, "Solar steam generation by heat localization", Nature Communications, Jul. 21, 2014, 7 pages.
Ghasemi et al, "Solar steam generation by heat localization", Nature Communications, Jul. 21, 2014, Supplemental Material, 20 pages.
Ito et al, "Multifunctional Porous Graphene for High-Efficiency Steam Generation by Heat Localization", Advanced Materials, 2015, vol. 27, pp. 4302-4307.
Ito et al, "Multifunctional Porous Graphene for High-Efficiency Steam Generation by Heat Localization", Advanced Materials, 2015, vol. 27, Supporting Information, pp. 1-7.
Jiang et al., "Bilayered Biofoam for Highly Efficient Solar Steam Generation", Advanced Materials, 2016, vol. 28, Issue 42, pp. 1-8.
Jiang et al., "Bilayered Biofoam for Highly Efficient Solar Steam Generation", Advanced Materials, 2016, vol. 28, Issue 42, Supporting Information, 8 pages.

(Continued)

*Primary Examiner* — Heidi Reese
(74) *Attorney, Agent, or Firm* — Armstrong Teasdale LLP

(57) ABSTRACT

The present disclosure is directed to ultrafiltration membranes based on bacterial nanocellulose and graphene oxide. In particular, the present disclosure is directed to the novel design and incorporation of membranes for realizing new, highly efficient, and environmentally-friendly anti-biofouling membranes for water purification.

5 Claims, 39 Drawing Sheets

(56) References Cited

OTHER PUBLICATIONS

Jozala et al, "Bacterial nanocellulose production and application: a 10-year overview", Appl Microbiol Biotechnol, Jan. 8, 2016, 11 pages.
Liu et al., A Bioinspired, Reusable, Paper-Based System for High-Performance Large-Scale Evaporation, Advanced Materials, 2015, vol. 27, pp. 2768-2774.
Liu et al., A Bioinspired, Reusable, Paper-Based System for High-Performance Large-Scale Evaporation, Advanced Materials, 2015, vol. 27, Supporting Information, pp. 1-13.
Ouyang et al., "Scalable preparation of three-dimensional porous structures of reduced graphene oxide/cellulose composites and their application in supercapacitors", Carbon, 2013, vol. 62, pp. 501-509.
Ultrafiltration, Nanofiltration and Reverse Osmosis, www.safewater.org, Jan. 2017, Fact Sheet, pp. 1-6.

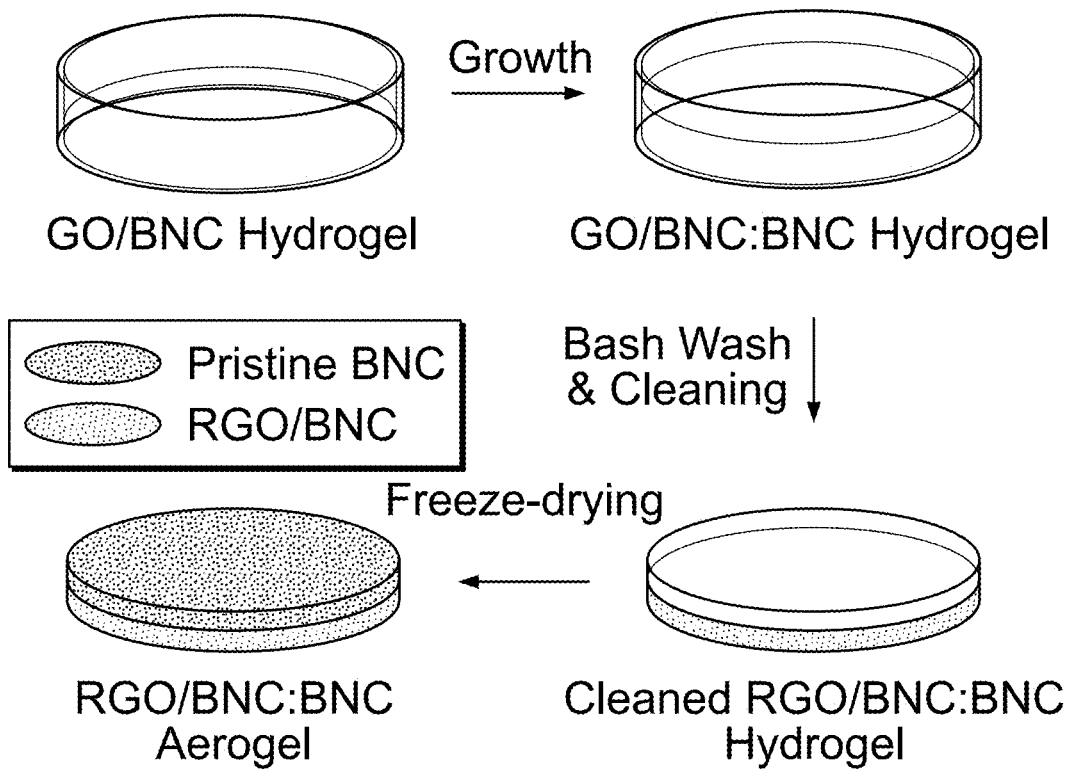
FIG. 1A
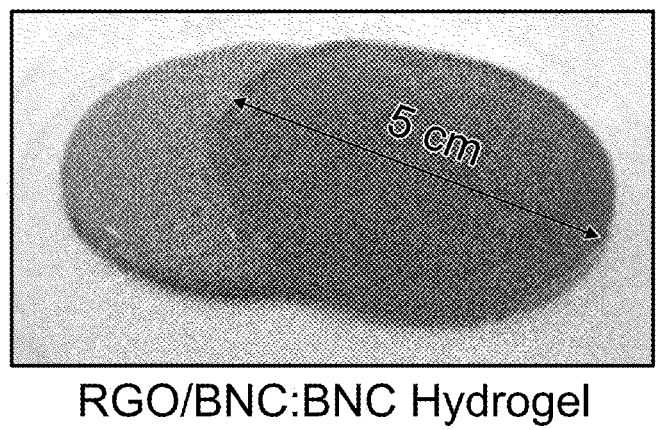
RGO/BNC:BNC Hydrogel
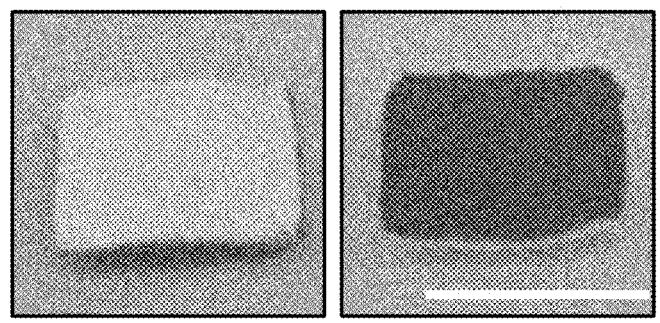
RGO/BNC:BNC Aerogel
FIG. 1B

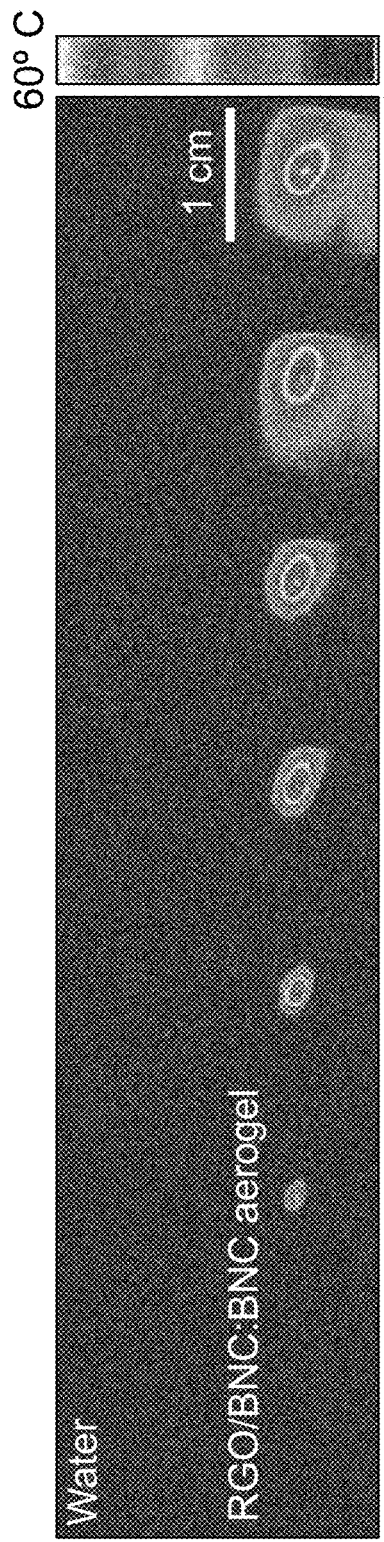
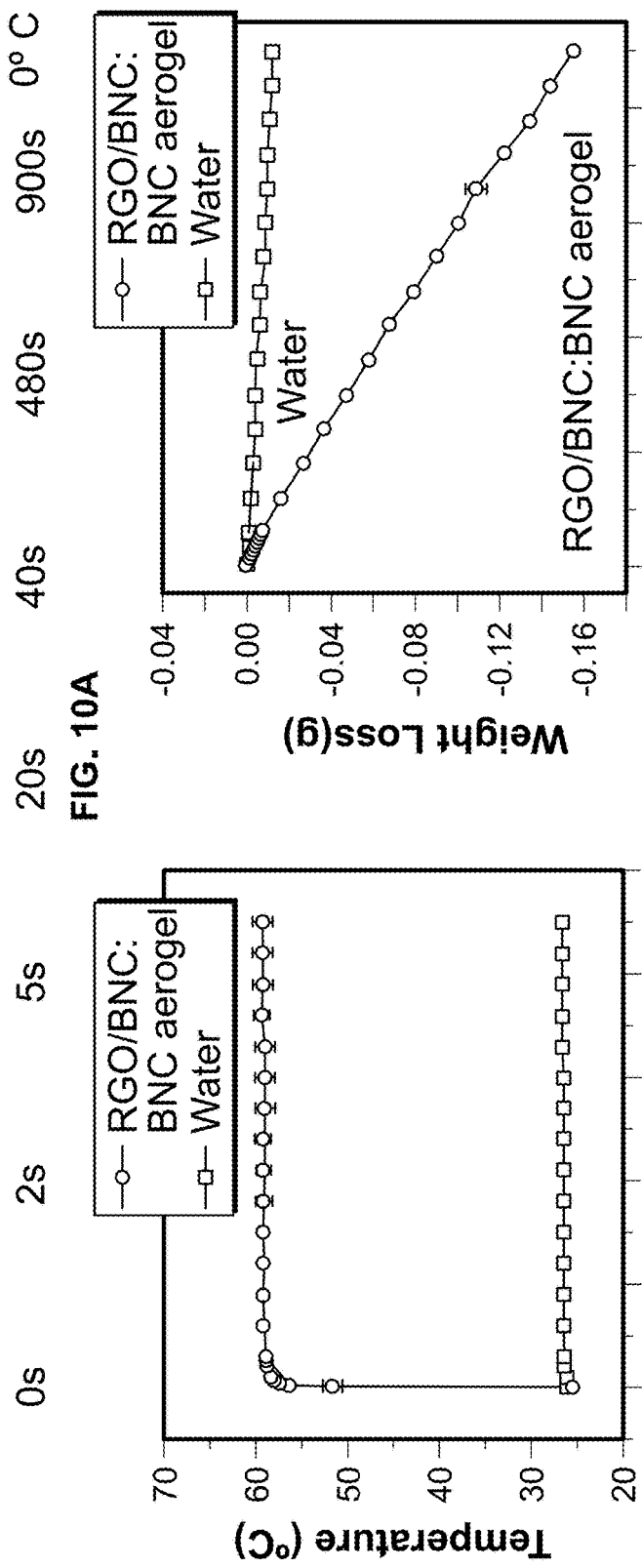
FIG. 10A
FIG. 10B
FIG. 10C

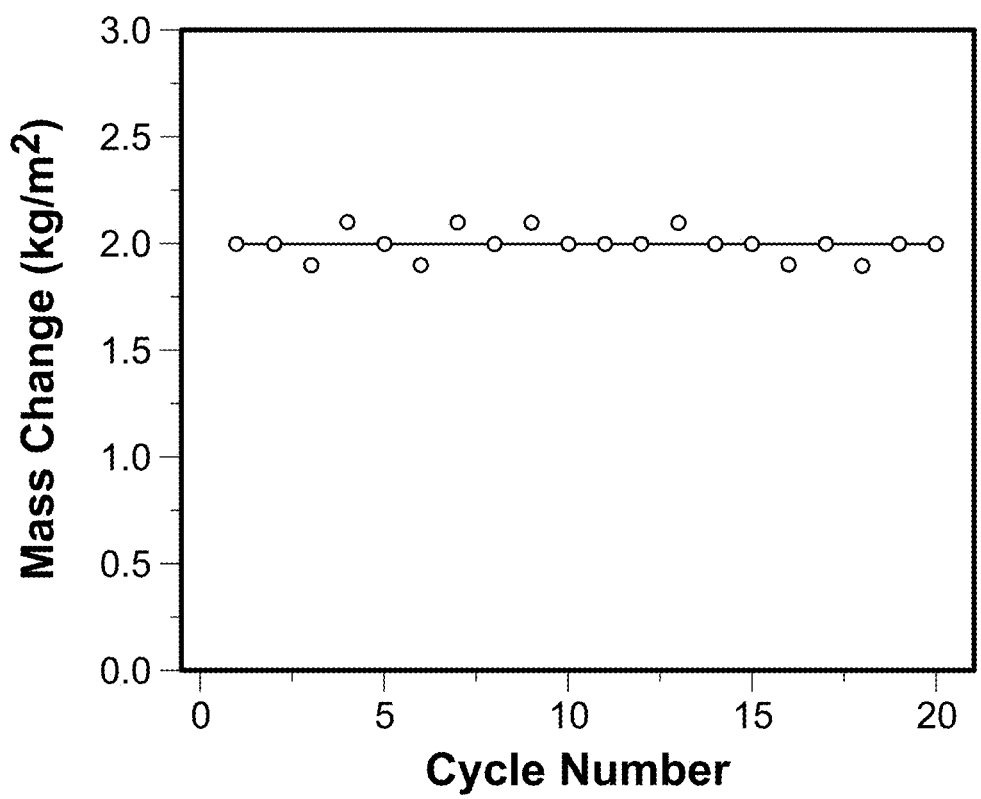
FIG. 21B
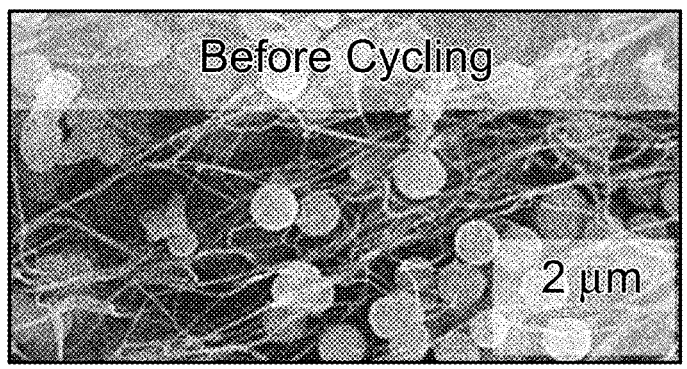
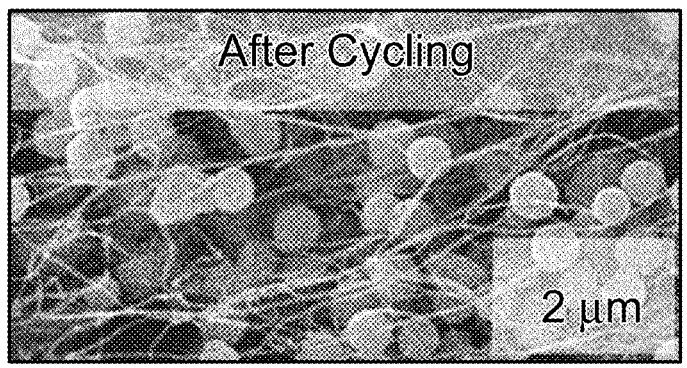
FIG. 21C

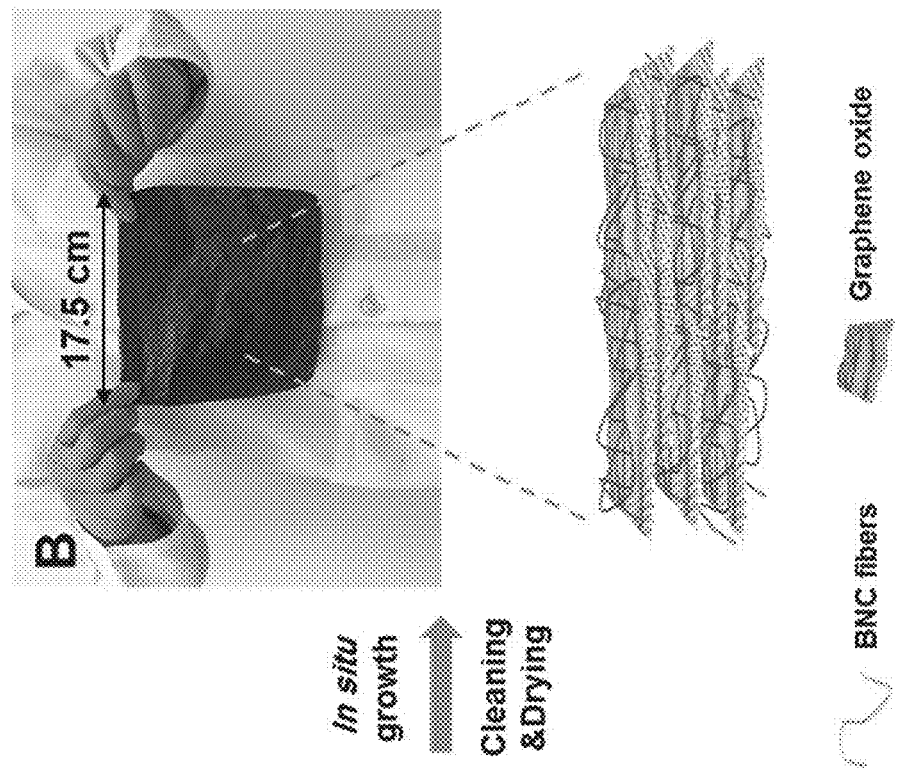
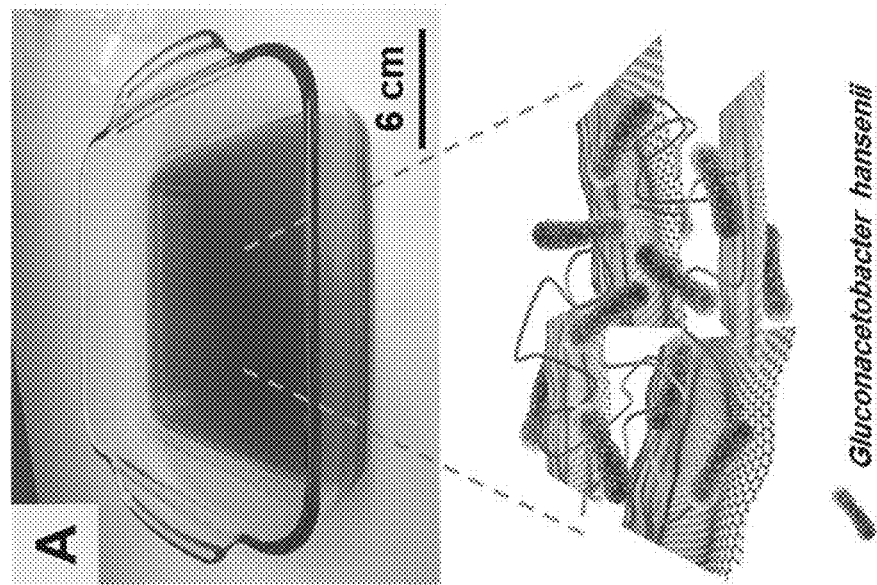

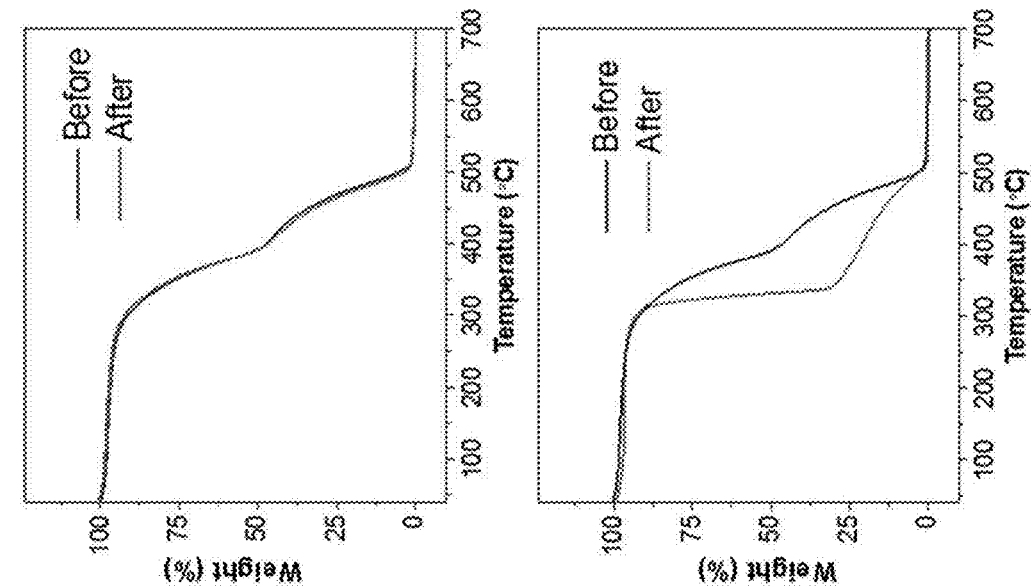
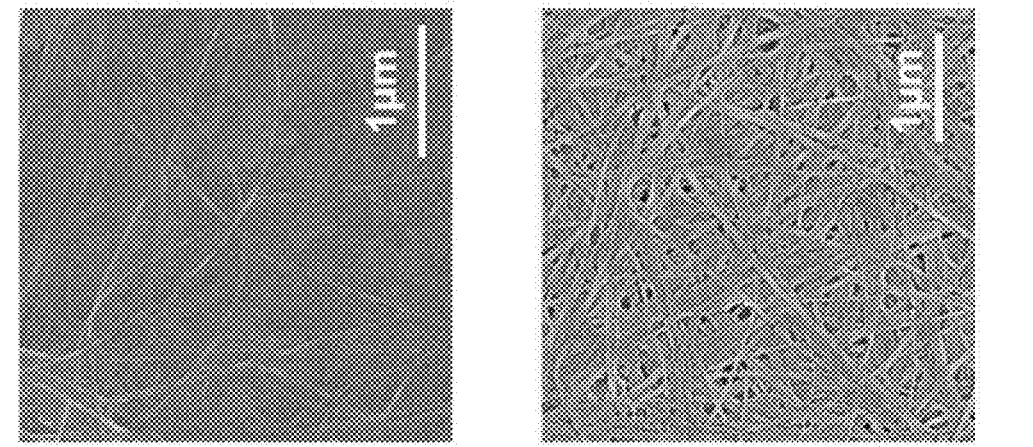
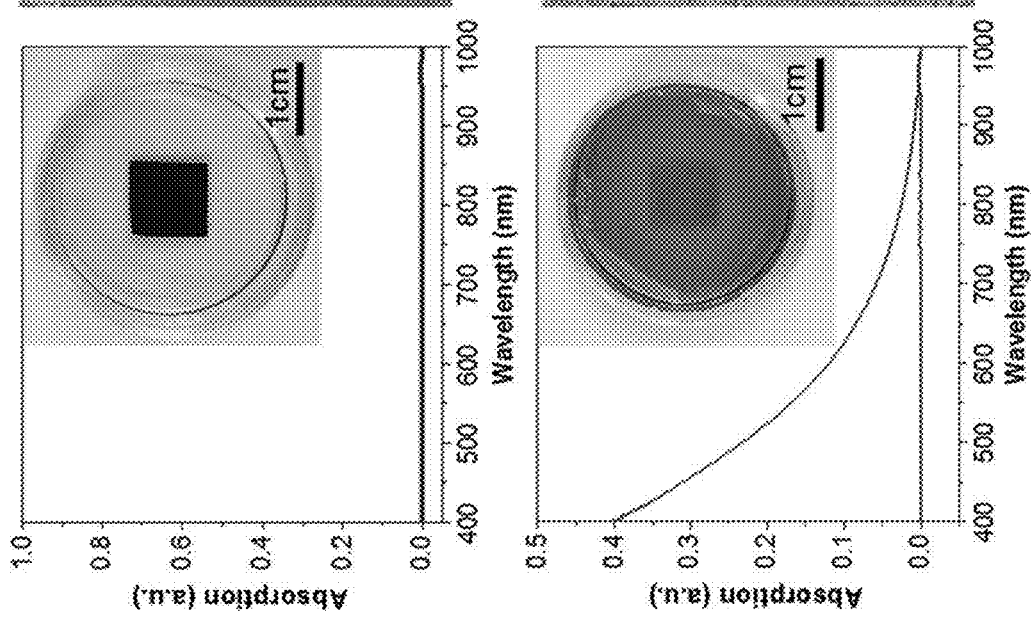

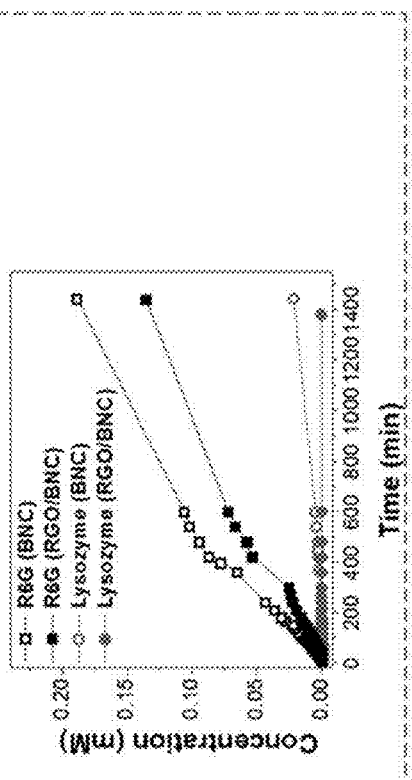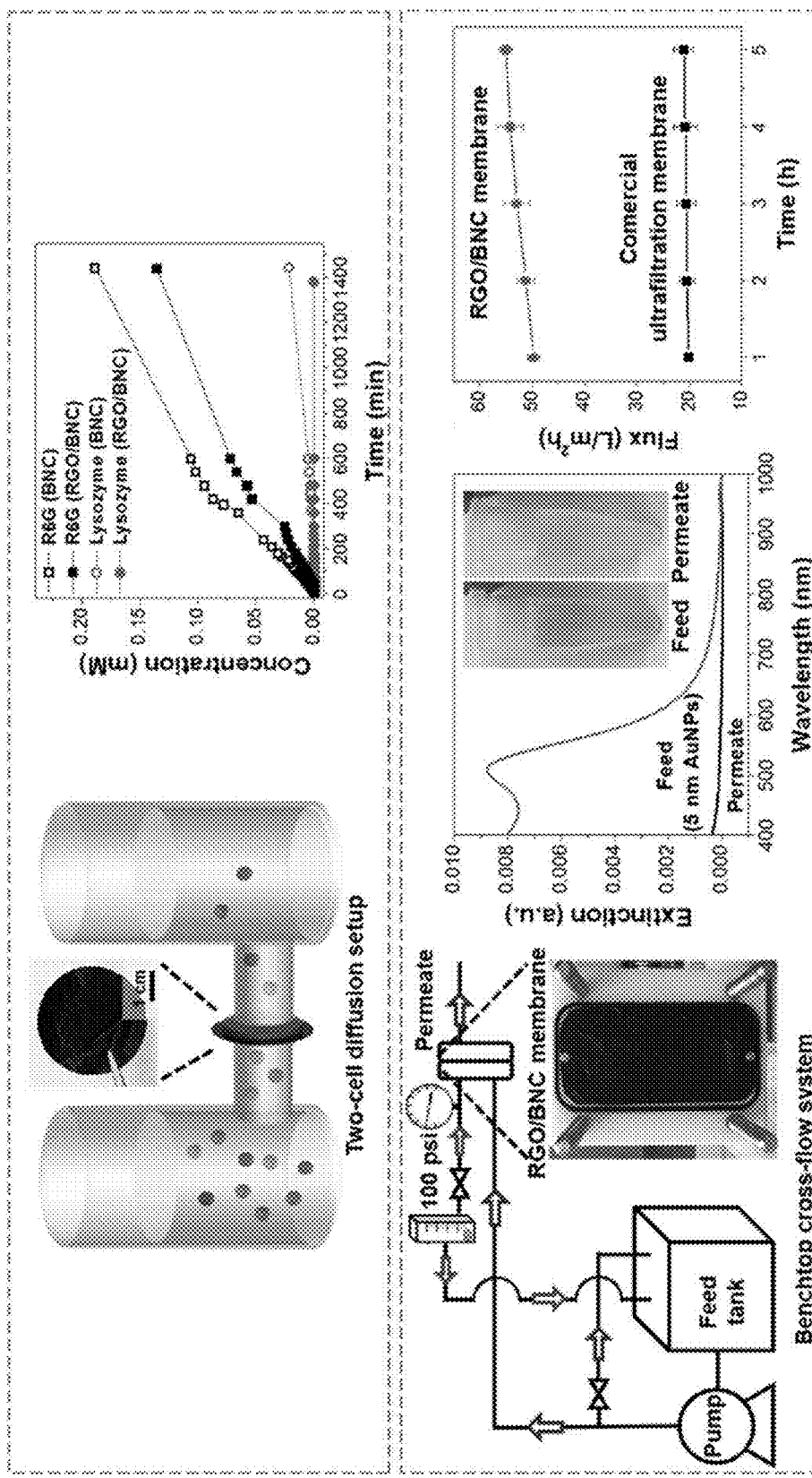
FIG. 29A FIG. 29B FIG. 29C FIG. 29D FIG. 29E

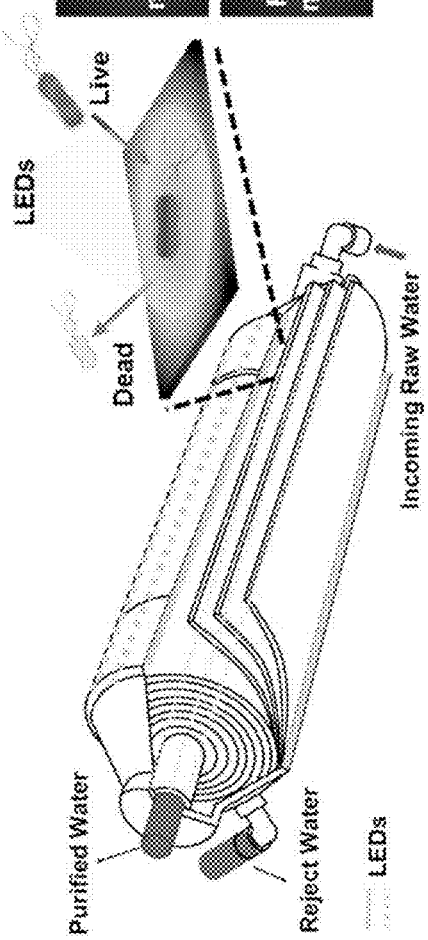
FIG. 30A
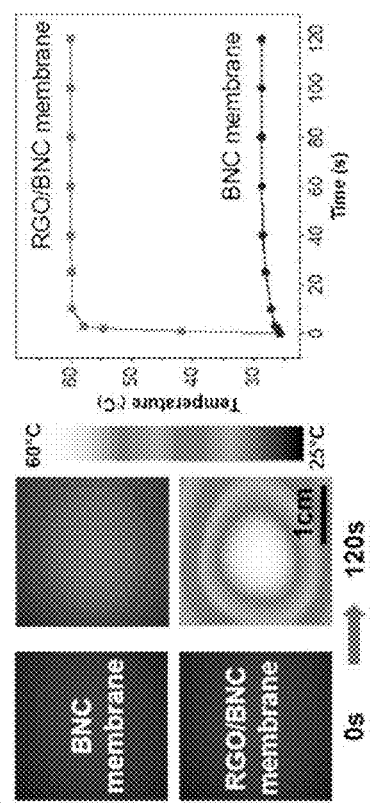
FIG. 30B
FIG. 30C
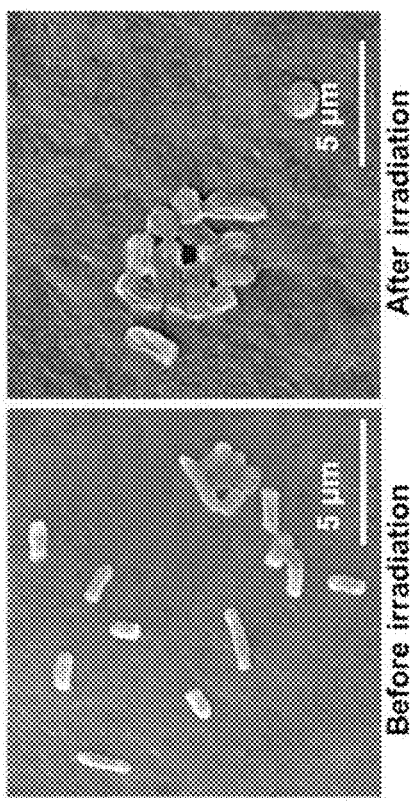
FIG. 30D  FIG. 30E
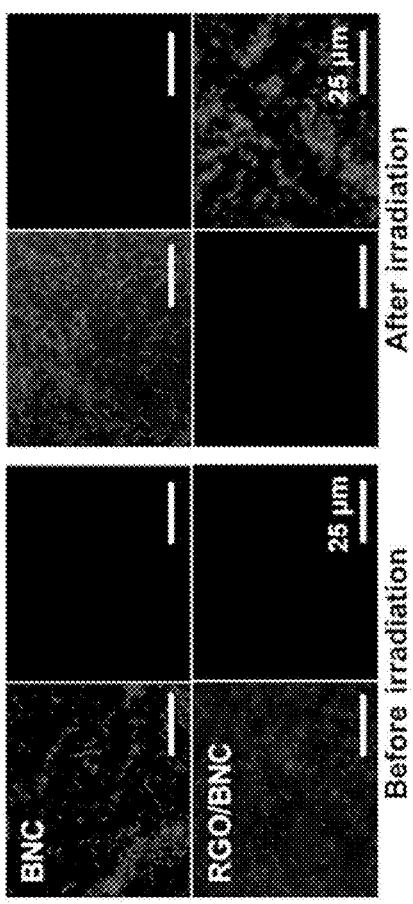
FIG. 30F  FIG. 30G

US 10,744,461 B2

ULTRAFILTRATION MEMBRANE BASED ON BACTERIAL NANOCELLULOSE AND GRAPHENE OXIDE

CROSS-REFERENCE TO RELATED APPLICATIONS

This application is a continuation-in-part application of U.S. application Ser. No. 15/653,942, filed on Jul. 19, 2017, and claims priority to U.S. Provisional Application 62/369,934 filed on Aug. 2, 2016 and U.S. Provisional Application 62/426,979 filed on Nov. 28, 2016, all of which are incorporated by reference in their entireties.

STATEMENT REGARDING FEDERALLY SPONSORED RESEARCH & DEVELOPMENT

This invention was made with government support under FA9550-15-1-0228 and 12RX11COR awarded by the United States Air Force Office of Scientific Research and CBET1604542 awarded by the national Science Foundation. The U.S. government has certain rights in the invention.

BACKGROUND OF THE DISCLOSURE

Meeting the ever increasing fresh water needs of the growing world population is one of the most serious global challenges of the $21^{st}$ century. Apart from the improved use of existing fresh water resources, desalination and water reuse are considered to be critical to overcome water scarcity that is affecting roughly half of the world's population. Two methods, namely, thermal desalination and reverse osmosis technology have been widely employed for desalination of sea water, which represents a virtually unlimited source. Solar water desalination, which relies on a sustainable and renewable energy source, is a promising method to alleviate fresh water scarcity in parts of the world with ample sunlight with low environmental impact. Steam generation using solar energy has been proven to be technically feasible and considered to be highly promising for water purification using sustainable energy source. However, low efficiency due to the heat loss associated with heating the bulk water and the requirement for high optical concentration limit the utilization of solar desalination in stand-alone solar power applications.

Previous designs involve either expensive materials or complex fabrication methods, with poor prospects in terms of scalability. Thus, there is a need for cost-effective and scalable heat-localization layers that provide high steam-generation efficiency. Additionally, most of these materials have a finite lifetime owing to pore clogging, degradation of the photothermal properties, and alteration of the surface properties of the water transport layer. Disposal of these materials can quickly pose a significant threat to the environment and ecosystems. For example, degradation and leaching of nanoscale photothermal materials into marine ecosystems, where these materials are most likely deployed can have lasting negative consequences. Thus, there is a need for a biodegradable composition for solar steam generation that provides high steam generation efficiency.

BRIEF SUMMARY OF THE DISCLOSURE

In one embodiment of the present disclosure, a composition comprising cellulose and a nanomaterial is disclosed.

In another embodiment of the present disclosure, a method for generating steam is disclosed. The method comprises placing a composition comprising cellulose and at least one nanomaterial in water; and exposing the composition to radiation thereby generating steam.

In yet another embodiment of the present disclosure, a method for the preparation of potable water is disclosed. The method comprises placing a composition comprising cellulose and at least one nanomaterial in water; exposing the composition to radiation thereby generating steam; and, condensing the steam thereby preparing potable water.

In another embodiment of the present disclosure, a method for the preparation of a bilayered biofilm comprising nanocellulose and a nanomaterial is disclosed. The method comprises providing a bacterial culture of *Gluconacetobacter hansenii* in a growth media; incubating the bacterial culture and the nanomaterial until a first biofilm layer forms; adding additional growth media on top of the first biofilm layer, the additional growth media comprising the bacterial culture and not comprising a nanomaterial; and, incubating the bacterial culture until a second biofilm layer forms thereby forming a bilayered biofilm. One of the bacterial cultures in growth media further comprises a nanomaterial.

BRIEF DESCRIPTION OF THE DRAWINGS

FIG. 1A is an exemplary embodiment of a schematic illustration showing the fabrication of RGO/BNC:BNC aerogel in accordance with the present disclosure. FIG. 1B is an exemplary embodiment of photographs of the cleaned RGO/BNC:BNC hydrogel and RGO/BNC:BNC aerogel in accordance with the present disclosure.

FIG. 10A is an exemplary embodiment of IR images showing the temperature of water and an RGO/BNC:BNC aerogel upon irradiation in accordance with the present disclosure. FIG. 10B is an exemplary embodiment of a plot showing the surface temperature of water and an RGO/BNC:BNC aerogel as a function of irradiation time in accordance with the present disclosure. FIG. 10C is an exemplary embodiment of a plot showing the cumulative weight loss of water through water evaporation under solar illumination as a function of irradiation time in accordance with the present disclosure.

FIG. 21B graphs the cycling of solar steam generation tests under 7 kW/m$^2$ solar irradiation for 15 min over 20 cycles. FIG. 21C is high-resolution SEM images of the PDA/BNC surface before and after 20 cycles of solar steam generation depicting the intact structure of the PDA/BNC foam.

FIGS. 26A-26B are exemplary embodiments of the fabrication of an RGO/BNC membrane in accordance with the present disclosure. FIG. 26A is an exemplary embodiment of GO in a bacterial medium in accordance with the present disclosure. FIG. 26B is an exemplary embodiment of an in situ grown RGO/BNC membrane after cleaning and drying in accordance with the present disclosure.

FIG. 27A is an exemplary embodiment of an AFM image of GO flakes deposited on a silicon substrate in accordance with the present disclosure. FIG. 27B is an exemplary embodiment of an X-ray photoelectron spectra of pristine GO in accordance with the present disclosure. FIG. 27C is an exemplary embodiment of an X-ray photoelectron spectra of base-washed GO in accordance with the present disclosure. FIG. 27D is an exemplary embodiment of a pristine BNC membrane in accordance with the present disclosure. FIG. 27E is an exemplary embodiment of SEM images of the surface of a pristine BNC membrane in accordance with the present disclosure. FIG. 27F is an exemplary embodiment of a cross-section of a pristine BNC membrane in accordance with the present disclosure. FIG. 27G is an exemplary embodiment of an RGO/BNC membrane in accordance with the present disclosure. FIG. 27H is an exemplary embodiment of SEM images of the surface of an RGO/BNC membrane in accordance with the present disclosure. FIG. 27I is an exemplary embodiment of a cross-section of an RGO/BNC membrane in accordance with the present disclosure.

FIGS. 28A-28F depict an exemplary embodiment of the stability of an RGO/BNC membrane in accordance with the present disclosure. FIG. 28A is an exemplary embodiment of the UV-Vis absorption spectra of an RGO/BNC immersed solution (at pH 7) before and after ultrasonic agitation for 5 hours in accordance with the present disclosure. The inset depicts an RGO/BNC membrane after sonication. FIG. 28B is an exemplary embodiment of an SEM image of an RGO/BNC membrane after ultrasonic agitation in accordance with the present disclosure. FIG. 28C is an exemplary embodiment of the TGA analysis of an RGO/BNC membrane before and after ultrasonic agitation in accordance with the present disclosure. FIG. 28D is an exemplary embodiment of the UV-Vis absorption spectra of an RGO-coated BNC immersed solution (at pH 7) before and after ultrasonic agitation for 5 hours in accordance with the present disclosure. The inset depicts an RGO-coated BNC membrane after sonication. FIG. 28E is an exemplary embodiment of an SEM image of an RGO-coated BNC membrane after ultrasonic agitation in accordance with the present disclosure. FIG. 28F is an exemplary embodiment of the TGA analysis of an RGO-coated BNC membrane before and after ultrasonic agitation in accordance with the present disclosure.

FIGS. 29A-29E depict an exemplary embodiment of mass transport performances and water flux tests in accordance with the present disclosure. FIG. 29A is an exemplary embodiment of a schematic diagram of a two-cell diffusion setup in accordance with the present disclosure. FIG. 29B is an exemplary embodiment of the diffusion of model solutes through pristine BNC and RGO/BNC membranes in accordance with the present disclosure. The average values of concentrations in the diffused part were obtained from three replicates for diffusion studies. FIG. 29C is an exemplary embodiment of a schematic diagram of a cross-flow flux test setup in accordance with the present disclosure. The RGO/BNC membranes were placed in between the cross-flow cell and tightly sealed. FIG. 29D is an exemplary embodiment of a UV-Vis extinction spectra in accordance with the present disclosure (indicating the rejection of 5 nm AuNPs filtered through RGO/BNC membranes in the cross-flow system under 100 psi—inset shows feed and permeate solutions). FIG. 29E is an exemplary embodiment of water fluxes of RGO/BNC membranes (about 8 micrometers thick) and commercial ultrafiltration membranes with three replicates in accordance with the present disclosure (100 psi was applied for the flux tests).

FIGS. 30A-30G depict an exemplary embodiment of photothermal and bactericidal performance under illumination in accordance with the present disclosure. FIG. 30A is an exemplary embodiment of a schematic showing the antifouling mechanism of an RGO/BNC membrane and a possible configuration of a spiral-wound UF module coupled with LEDs in accordance with the present disclosure. FIG. 30B is an exemplary embodiment of IR images showing the temperature of the pristine BNC and the RGO/BNC membranes in water under illumination in accordance with the present disclosure. FIG. 30C is an exemplary embodiment of a plot showing the temperature of pristine BNC and the RGO/BNC membranes in water under 2.9 kW/m$^2$ illumination (as a function of irradiation time) in accordance with the present disclosure. FIG. 30D is an exemplary embodiment of the fluorescence images of *E. coli* on BNC and RGO/BNC membranes before irradiation in accordance with the present disclosure. FIG. 30E is an exemplary embodiment of the fluorescence images of *E. coli* on BNC and RGO/BNC membranes after irradiation in accordance with the present disclosure. FIG. 30F is an exemplary embodiment of SEM images of *E. coli* on an RGO/BNC membrane before irradiation in accordance with the present disclosure. FIG. 30G is an exemplary embodiment of SEM images of *E. coli* on an RGO/BNC membrane after irradiation in accordance with the present disclosure.

DETAILED DESCRIPTION OF THE DISCLOSURE

Figure 1C:
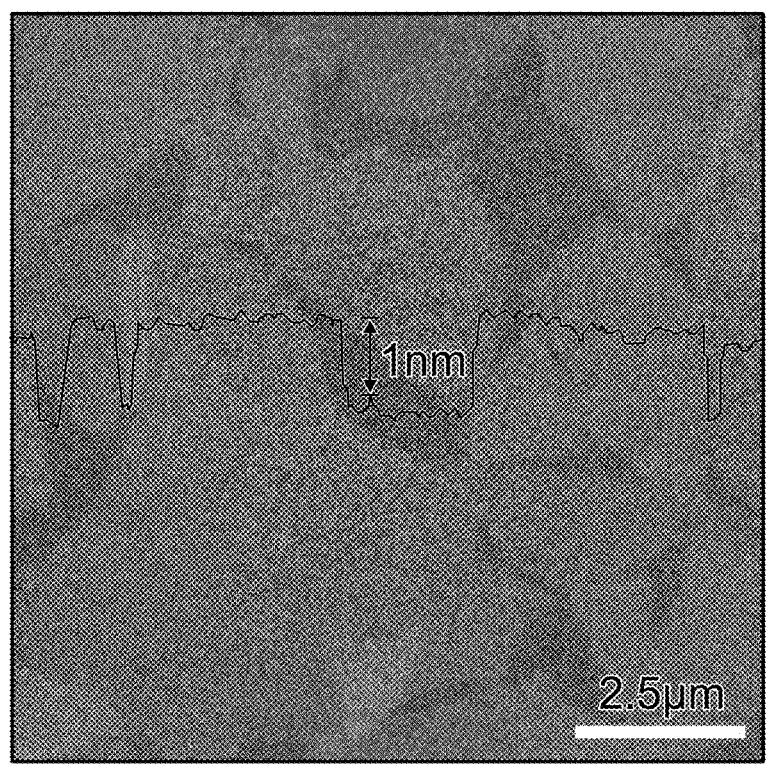
FIG. 1C is an exemplary embodiment of an AFM image of GO flakes deposited on a silicon substrate in accordance with the present disclosure.
Figure 1D:
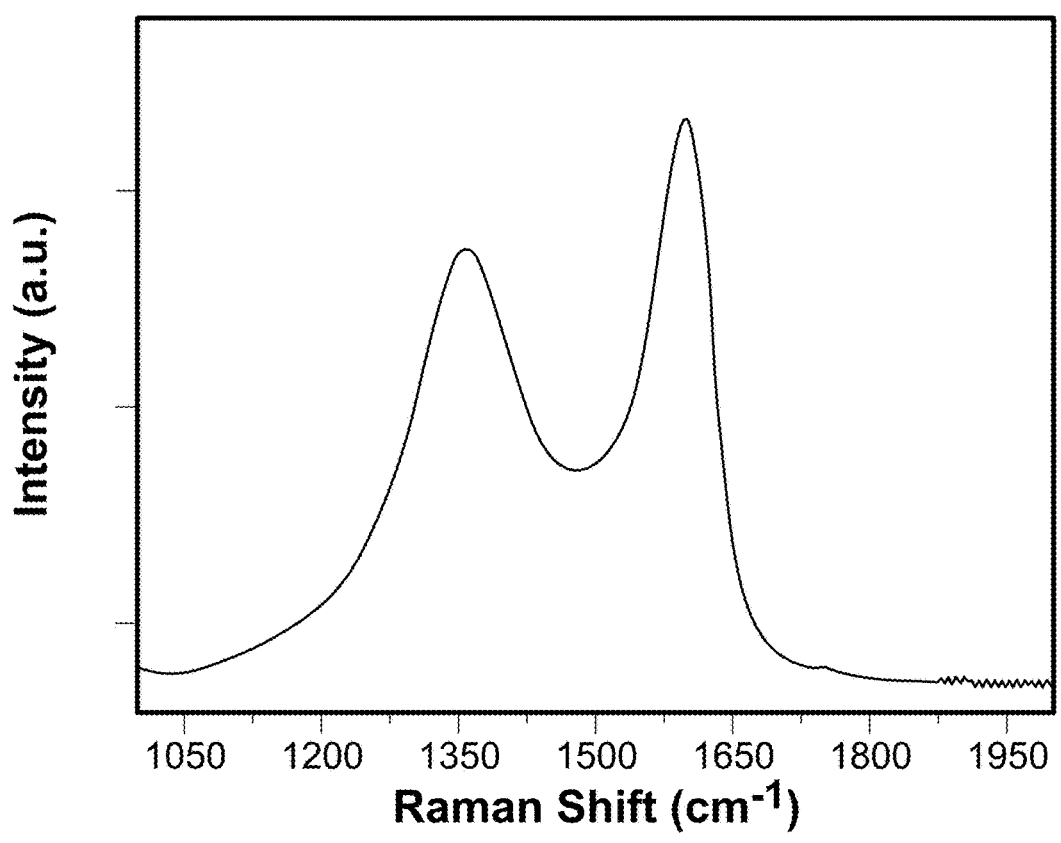
FIG. 1D is an exemplary embodiment of a Raman spectrum of GO flakes in accordance with the present disclosure.
Figure 2A:
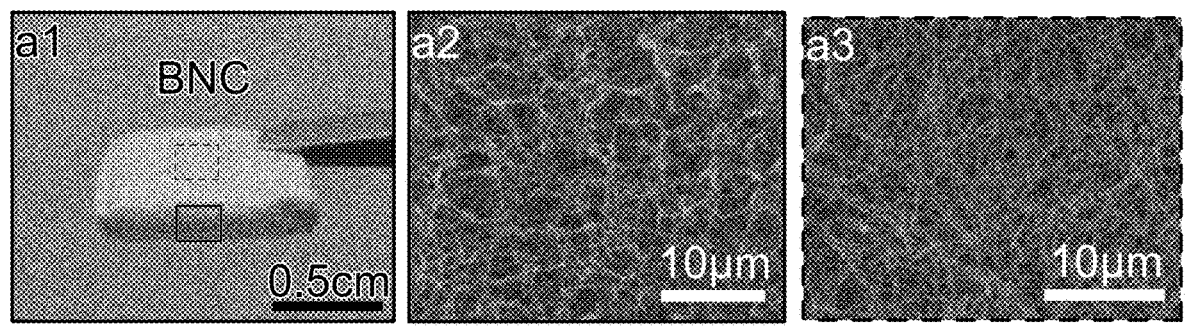
FIG. 2A is an exemplary embodiment of an optical image, an SEM image and a top surface image of a BNC aerogel in accordance with the present disclosure.
Figure 2B:
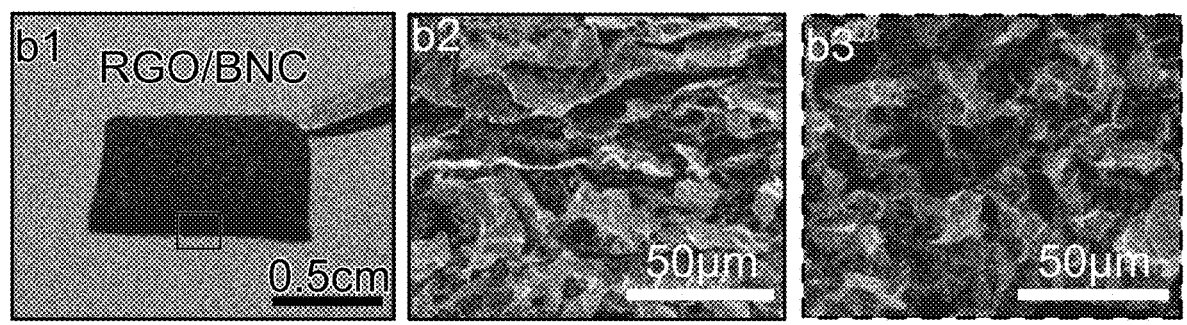
FIG. 2B is an exemplary embodiment of an optical image, an SEM image and a top surface image of an RGO/BNC aerogel in accordance with the present disclosure.
Figure 2C:
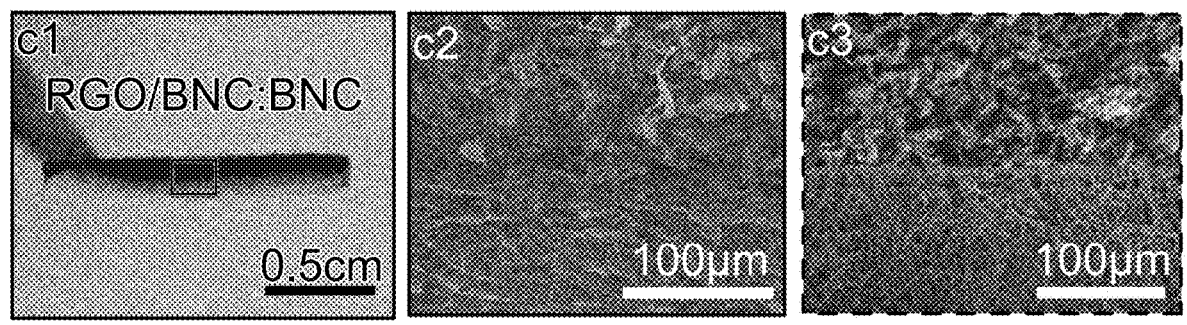
FIG. 2C is an exemplary embodiment of an optical image, an SEM image and a top surface image of an RBO/BNC:BNC aerogel in accordance with the present disclosure.

The present disclosure is directed to steam generation through the efficient harvesting of solar energy. In particular, the present disclosure is directed to bilayered structures that are cost-effective and scalable that provide high steam-generation efficiency. The bilayered structures include bilayered biofoams (e.g., RGO/BNC) and wood-graphene oxide composites. Steam generation through efficient harvesting of solar energy is highly promising for large-scale power generation, desalination, and water purification.

Confining heat to air/water interface (i.e., the evaporating surface) is considered to be a highly promising approach to improve the efficiency of evaporation and the steam-generation process. Steam generation through heat localization at the evaporation surface involves large optical absorption at the surface, photothermal (light-to-heat) conversion of incident light, confinement of heat to the evaporative surface, and transport of water from the bulk to the heat localization layer for efficient evaporation. Over the past several years, various heat localization layers have been demonstrated to significantly improve the steam-generation efficiency compared to conventional bulk heating methods.

A number of efforts have been dedicated to the use of novel nanomaterials as light absorbing and heat generating materials. For example, plasmonic nanostructures, which exhibit large absorption and scattering of light in the visible and near infrared (NIR) regions of the electromagnetic spectrum, have been demonstrated to be excellent candidates for steam generation. Owing to their photothermal properties, carbon-based materials such as graphene, carbon black nanoparticles and carbon foam have also been employed for solar steam generation.

Apart from the materials employed in the photothermal layers, support materials on which the photothermal layers are deposited are equally important for a high-efficiency solar steam generation. The key considerations for such support materials are hydrophilicity and porosity for efficient transport of water from the bulk to the evaporative surface, low thermal conductivity to impede the flow of heat from the evaporative surface to the bulk water, lightweight to ensure that the materials remain afloat on water surface, and cost-efficiency and scalability for real-world application. A number of materials such as anodic aluminum oxide (AAO) membrane, gauze, paper have been employed as the supporting materials for steam generation.

The present disclosure minimizes heat losses and improves the efficiency of water desalination by using a bilayered structure for solar steam generation. In a typical bilayered structure, the top layer is comprised of a photothermal material that efficiently absorbs light and converts it into heat. The bottom layer, typically with low thermal conductivity, serves as a thermal insulation layer to minimize the heat loss to the bulk water, thus improving the overall efficiency of the solar steam generation.

Yet another promising photothermal material, graphene oxide (GO), exhibits a broadband light absorption from visible to NIR range, making it excellent for steam generation applications. The unique optical properties of GO have been investigated for various optoelectronic and biomedical applications.

Disclosed herein is that a number of the inherent physical and chemical properties of wood such as high porosity, lightweight, low thermal conductivity and hydrophilicity, make it an excellent material for a solar steam generation. A wood-graphene oxide (GO) composite for solar steam generation enables heat localization at the evaporative surface and provides efficient transport of water to the evaporative surface through the microchannels of the wood. The unique properties of wood, as well as GO, are well-suited for high optical absorption, photothermal conversion, heat localization, water transport and rapid evaporation resulting in a highly efficient solar steam generation system. The wide availability of wood combined with the simple coating process makes the wood-GO composite demonstrated highly attractive for steam generation and water distillation in resource-limited settings with ample sunlight.

Additionally, a bilayered hybrid biofoam composed of bacterial nanocellulose (BNC) and reduced graphene oxide (RGO) for solar steam generation through heat localization at the evaporation surface is disclosed. BNC is composed of highly pure cellulose nanofibrils, produced from dextrose through a series of biochemical steps followed by the self-assembly of the secreted cellulose fibrils from bacteria in the culture medium. BNC is a highly attractive material for the fabrication of functional foams due to its large specific surface area, open microporous structure, excellent mechanical properties, and facile and scalable synthesis. So far, most of the functional foams based on BNC rely on either in situ growth or adsorption of functional nanostructures or infiltration of polymers in the porous cellulose network after harvesting the BNC from the culture. A novel approach for the fabrication of photothermally active biofoam involves the in situ incorporation of GO flakes into BNC during its growth. The bilayer structure of the functional foam is tailored for high optical absorption, photothermal conversion, heat localization, and water transport to the evaporation surface resulting in a highly efficient solar steam generation. The bilayer structure exhibits excellent stability even under vigorous mechanical agitation and harsh chemical conditions, which is quite surprising considering the simplicity of the manner of fabrication.

Graphene oxide (GO) exhibits a broad optical absorption over the visible and near infrared (NIR) parts of the electromagnetic spectrum and excellent photothermal transduction. Unlike graphene flakes, which tend to stack and aggregate in aqueous solutions, GO exhibits excellent water solubility. GO is essentially sheets of graphene with carboxylic functional groups at the edges and phenol hydroxyl and epoxide groups on the basal planes. Thus, the hydrophilicity of GO is attributed to the hydroxyl and epoxide groups on the basal planes and carboxyl functionalities at the edges. Crumpled graphene oxide and crumpled reduced graphene oxide produced by aerosol synthesis methods also exhibit excellent stability and hydrophilicity. Graphene-based materials have been extensively investigated for various optoelectronic applications, including transparent electrodes, photodetectors, and as electron- and hole-transport layers in photovoltaic devices. While being electrically conductive, a single layer of graphene exhibits only a small optical absorbance ($\approx 3\%$), making it an excellent candidate for transparent electrodes. However, the cumulative optical absorbance of a few graphene monolayers in tandem can quickly add up, making graphene materials an excellent choice for applications demanding high optical absorption.

In accordance with some embodiments of the disclosure, a composition comprising cellulose and a nanomaterial is disclosed. In some embodiments, the cellulose is a gel that comprises nanocellulose, and the nanomaterial is graphene oxide, reduced graphene oxide or a combination thereof. This composition has numerous uses, including, but not limited to, localizing heat at the surface of water to efficiently generate steam using solar radiation. The water may or may not be suitable for human consumption prior to steam generation. In some embodiments, steam is condensed and collected thereby generating water that is suitable for human consumption.

In some embodiments, the composition comprises cellulose and graphene oxide, reduced graphene oxide or both. In some embodiments, the cellulose is wood. This composition has numerous uses including, but not limited to, localizing heat at the surface of water to efficiently generate steam using solar radiation. The water may or may not be suitable for human consumption prior to steam generation. In some embodiments, steam is condensed and collected thereby generating water that is suitable for human consumption.

Definitions

The term "aerogel" as used herein refers to the resulting composition when all of the liquid in a gel is replaced with a gas or mixture of gases (e.g., air). They are extremely low density solids having very low thermal conductivity.

The term "gel" as used herein is a group of polymeric materials whose structure renders them capable of holding large amounts of a liquid in their three-dimensional networks. By weight, gels are mostly liquid, yet they behave like solids due to a three-dimensional cross-linked network within the liquid. "Hydrogels" are gels in which the liquid is water.

The term "nanocellulose" as used herein refers to nanostructure cellulose composed of thixotropic nanosized cellulose fibrils with a high length to width ratio. They are prepared by different methods, including, but not limited to, bacterial growth and acid hydrolysis of native cellulose fibers.

The term "biodegradable" as used herein means capable of being broken down (decomposed) by the action of bacteria, microorganisms or other living organisms. In most instances, a substance is biodegradable if it is broken down into substances that are not harmful to the environment. It is recognized that the harm caused by decomposition products may not be recognized for many years after the break down occurs or additional research is performed. "Not harmful to the environment" as used herein refers to the state of the art as is known upon the submission of this application.

The term "steam" as used herein refers to water in the vapor phase. It is not limited to water at or above 100° C. at standard atmospheric pressure.

The terms "efficiency of steam generation" or "steam-generation efficiency" as used herein are interchangeable and is quantified by measuring the weight loss of water (due to water evaporation) as a function of irradiation time.

The term "evaporation efficiency" (η) as used herein is determined from the following equation:

$$\eta = \frac{mh_{LV}}{l}$$

where m is the evaporation rate, $h_{LV}$ is the total enthalpy of sensible heat (294 J/g, from 30 to 100° C. with a specific heat of 4.2 J·g/K and phase change of liquid to water (2256 J/g)), and l is the incident laser power density. It measures the photothermal efficiency in a system (i.e., light to heat conversion).

In some aspects of this disclosure, the cellulose is in the form of nanocellulose. In some embodiments, the nanocellulose is in the form of cellulose nanofibers, microfibrillated cellulose, nanocrystalline cellulose, bacterial nanocellulose and combinations thereof.

In some aspects, bacterial nanocellulose (BNC) is used. BNC is composed of highly pure cellulose nanofibrils. One method of production of BNC is from dextrose through a series of biochemical steps followed by the self-assembly of the secreted cellulose fibrils from bacteria in the culture medium. BNC is a highly attractive material for the fabrication of functional foams due to its large specific surface area, open microporous structure, excellent mechanical properties, and facile and scalable synthesis. Most of the functional foams based on BNC rely on either in situ growth or adsorption of functional nanomaterials or infiltration of polymers in the porous cellulose network after harvesting the BNC from the culture.

In some embodiments, the BNC is formed in the presence of at least one nanomaterial. The term "nanomaterial" as used herein refers to a solid material having one, two or three of its dimensions less than about 1000 nanometers, preferably about 500 nanometers, most preferably about 100 nanometers. Said materials can either occur naturally in nature or be manufactured. They comprise a variety of shapes, sizes and properties. Examples include, but are not limited to, fullerenes, carbon nanotubes, quantum dots, graphene oxide flakes, ceramics, clays, and metal nanoparticles (e.g., gold and silver). They are often divided into four categories: carbon-based, metal-based, dendrimers, and composites.

In some embodiments, BNC is formed in the presence of a nanomaterial thereby forming a nanocomposite material. As used herein, the term "nanocomposite material" means a composition comprising at least two phases, wherein at least one of the phases is a nanomaterial. For example, in some embodiments, the nanocomposite material comprises cellulose or nanocellulose and a nanomaterial such as molybdenum disulfide nanoparticles, functionalized carbon nanotubes, polydopamine nanoparticles, graphene, graphene oxide, reduced graphene oxide or a combination thereof. In some embodiments, the nanomaterial is polydopamine, graphene oxide, reduced graphene oxide or a combination of both. In some embodiments, the composition is an aerogel, a hydrogel, a colloid, a porous media, a polymer, a copolymer or combinations thereof. In some embodiments, the nanomaterial is preferably polydopamine. In yet another embodiment, the nanomaterial is preferably graphene oxide, reduced graphene oxide or a combination thereof.

When the BNC is formed in the presence of the nanomaterial, it provides a more robust nanocomposite material such that the nanomaterial is not easily removed from the BNC gel matrix. The BNC gel matrix comprising the nanomaterial is stable to sonication for at least about 10 minutes, at least about 20 minutes, at least about 30 minutes, at least about 45 minutes, at least about one hour, at least about two hours, or at least about five hours.

In some embodiments, the BNC is formed in the presence of graphene oxide (GO) flakes, reduced graphene oxide flakes or a combination thereof. Graphene oxide flakes can be commercially obtained or prepared by methods known in the art. In some embodiments, the graphene oxide flakes are reduced forming reduced graphene oxide (RGO). Formation of RGO from GO is prior to, coinciding with, or subsequent to incorporation into the BNC. The graphene oxide is partially or completely reduced. In some embodiments, none of the graphene oxide is reduced. In some embodiments, over about 10% of the graphene oxide is reduced, over about 15% of the graphene oxide is reduced, over about 20% of the graphene oxide is reduced, over about 25% of the graphene oxide is reduced, over about 30% of the graphene oxide is reduced, over about 35% of the graphene oxide is reduced, over about 40% of the graphene oxide is reduced, over about 45% of the graphene oxide is reduced, over about 50% of the graphene oxide is reduced, over about 55% of the graphene oxide is reduced, over about 60% of the graphene oxide is reduced, over about 65% of the graphene oxide is reduced, over about 70% of the graphene oxide is reduced, over about 75% of the graphene oxide is reduced, over about 80% of the graphene oxide is reduced, over about 85% of the graphene oxide is reduced, over about 90% of the graphene oxide is reduced, over about 95% of the graphene oxide is reduced, or about 100% of the graphene oxide is reduced.

The concentration of graphene oxide or reduced graphene oxide in the cellulose matrix is determined by the amount of graphene oxide added during formation of the gel. In some embodiments, the GO or RGO concentration, as measured by thermogravimetric analysis, is from about 2 wt. % to about 50 wt. %, about 3 wt. % to about 48 wt. %, about 4 wt. % to about 45 wt. %, about 7 wt. % to about 40 wt. %, about 10 wt. % to about 38 wt. %, about 13 wt. % to about 35 wt. %, about 15 wt. % to about 32 wt. %, about 20 wt. % to about 30 wt. %, about 25 wt. % to about 30 wt. %. In some embodiments the GO or RGO concentration is about 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. %, 31 wt. %, 32 wt. %, 33 wt. %, 34 wt. %, 35 wt. %, 36 wt. %, 37 wt. %, 38 wt. %, 39 wt. %, 40 wt. %.

In some embodiments, the BNC is formed in the presence of polydopamine nanoparticles. Polydopamine (PDA), formed by the oxidation of dopamine, is an important eumelanin-like biopolymer known for its versatile adhesion properties and universal surface modification. PDA particles can be obtained by methods known in the art. In some embodiments, the size of the PDA particles is controlled during the polymerization reaction by altering the concentration of ammonia in the reaction. In some embodiments, the PDA particles are about 0.05 µm in diameter, 0.1 µm in diameter, 0.2 µm in diameter, 0.3 µm in diameter, 0.4 µm in diameter, 0.5 µm in diameter, 0.75 µm in diameter, 1.0 µm in diameter, 1.25 µm in diameter, 1.5 µm in diameter, 1.75 µm in diameter, 2 µm in diameter, 3 µm in diameter, 4 µm in diameter, 5 µm in diameter, 7.5 µm in diameter, 10 µm in diameter, 15 µm in diameter, 20 µm in diameter.

The concentration of PDA in the cellulose matrix is determined by the amount of PDA added during formation of the gel. In some embodiments, the PDA concentration, as measured by thermogravimetric analysis, is from about 2 wt. % to about 60 wt. %, about 3 wt. % to about 58 wt. %, about 4 wt. % to about 55 wt. %, about 7 wt. % to about 50 wt. %, about 10 wt. % to about 48 wt. %, about 13 wt. % to about 45 wt. %, about 15 wt. % to about 42 wt. %, about 20 wt. % to about 40 wt. %, about 25 wt. % to about 40 wt. %. In some embodiments the PDA concentration is about 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. %, 31 wt. %, 32 wt. %, 33 wt. %, 34 wt. %, 35 wt. %, 36 wt. %, 37 wt. %, 38 wt. %, 39 wt. %, 40 wt. %, 41 wt. %, 42 wt. %, 43 wt. %, 44 wt. %, 45 wt. %, 46 wt. %, 47 wt. %, 48 wt. %, 49 wt. %, 50 wt. %, 51 wt. %, 52 wt. %, 53 wt. %, 54 wt. %, 55 wt. %, 56 wt. %, 57 wt. %, 58 wt. %, 59 wt. %, 60 wt. %.

In yet another aspect, the BNC and nanocomposite material is biodegradeable or comprises mostly biodegradable materials. Mostly in this instances means that at least 75% of the composition comprises biodegradable materials. In still yet another aspect, the BNC and nanocomposite material is comprises only biodegradable materials. PDA is a biodegradable polymer. In some embodiments, the biodegradable composition comprises or consists essentially of BNC and PDA.

Bacteria capable of producing cellulose or nanocellulose include, but are not limited to *Gluconacetobacter hansenii* (ATCC 23769 or ATCC 53582), *Gluconacetobacter xylinus* (formerly named *Acetobacter xylinum*), *Escherichia coli*, *Agrobacterium tumefaciens*, *Acetobacter pasteurianus*, *Asaia bogorensis*, *Rhizobium* spp., *Sarcina ventriculli*, and *Gluconacetobacter sacchari*. In some embodiments, the bacteria for producing nanocellulose is *Gluconacetobacter hansenii*, *Acetobacter pasteurianus*, or *Gluconacetobacter xylinus*. In some embodiments, the bacteria is *Gluconacetobacter hansenii*. The fabrication of a bilayer structure involves growing *Gluconacetobacter hansenii* bacteria in the presence of GO, RGO or a combination thereof.

In some embodiments, the bacterial culture is grown in the presence of GO or RGO flakes until a bacterial film of nanocellulose is formed that incorporates the GO or RGO flakes (BNC/GO or BNC/RGO). In another embodiment, the bacterial culture is grown in the presence of PDA particles until a bacterial film of nanocellulose is formed that incorporates the PDA particles (PDA/BNC). In some embodiments, only one layer is formed while in yet another aspect, more than one layer is formed. Additional layers of the nanocellulose may be formed by adding additional bacterial growth media that comprises the bacterial culture on the surface of the previously formed nanocellulose layer. The additional grown media may or may not comprise the nanomaterial. Each individual layer may or may not comprise the nanomaterial, and the nanomaterial may be the same or different between different layers. This process may be repeated until a plurality of layers is formed. In some embodiments, the final composition will comprise from one to fifty layers, from two to forty layers, from two to thirty layers, from two to twenty layers, from two to ten layers, from two to five layers. Each individual layer may or may not comprise a nanomaterial. In one embodiment, the final composition has two layers wherein one layer comprises the nanomaterial and one layer does not comprise a nanomaterial. In another embodiment, the final composition comprises two layers wherein one layer comprises BNC without any nanomaterial, and the second layer comprises BNC and graphene oxide, reduced graphene oxide, polydopamine or any combination thereof. In some embodiments of the bilayered composition, the first layer formed comprises the nanomaterial and the second formed layer does not comprise a nanomaterial. In yet another embodiment, this is reversed. The first layer formed does not comprise the nanomaterial while the second formed layer does comprise the nanomaterial. In some aspects, the composition comprises only one nanomaterial. In yet another aspect, the composition comprises more than one nanomaterial.

In some embodiments, the nanomaterial is selected from the group consisting of graphene oxide, reduced graphene oxide, molybdenum disulfide ($MoS_2$), polydopamine (PDA, melanin), functionalized multiwalled carbon nanotubes (e.g., —OH, —COOH modified) and combinations thereof.

In some embodiments, each layer of the nanocellulose biofilm has a thickness of from about 0.1 to about 50 mm, from about 0.2 to about 45 mm, from about 0.5 to about 40 mm, from about 0.8 to about 35 mm, from about 1.0 to about 30 mm, from about 1.2 to about 25 mm, from about 1.5 to about 20 mm, from about 1.7 to about 15 mm, or from about 2.0 to about 10 mm.

In another aspect of this disclosure, a method of making steam is presented utilizing the cellulose and nanomaterial composition as disclosed elsewhere herein. By placing the composition on water and exposing said composition to radiation, heat is generated via photothermal conversion of the radiation into heat. The heat is localized within or near the composition thereby heating the water. The amount of steam generated is a function of the amount of heat generated and may be measured as a function of time. In some embodiments, the water is condensed. The condensation of the water may be into a separate physical location as the source water thereby affecting a distillation or purification of the source water. If the source water is not suitable for human consumption, this method may be utilized to prepare potable water.

The steady state evaporation rate of water comprising the cellulose and nanomaterial composition is a function of its structure and manner in which the exposure to radiation is done. A nonlimiting list of factors that affect the steady state evaporation rate of water include cellulose type, nanomaterial identity, nanomaterial concentration, number of layers of the composition, thickness of the composition, and strength and nature of the radiation used. The steady state evaporation rate is determined as described in the Examples herein. In some embodiments, the steady state evaporation rate under simulated solar irradiation (e.g., 10 kW/m$^2$) is greater than greater than about 6 kg/m$^2$·h, greater than about 7 kg/m$^2$·h, greater than about 8 kg/m$^2$·h, greater than about 9 kg/m$^2$·h, greater than about 10 kg/m$^2$·h, greater than about 11 kg/m$^2$·h, greater than about 12 kg/m$^2$·h, greater than about 13 kg/m$^2$·h, greater than about 15 kg/m$^2$·h, greater than about 20 kg/m$^2$·h, or greater than about 25 kg/m$^2$·h.

In some embodiments, the steady state evaporation rate under a simulated solar beam irradiation (e.g., 10 kW/m$^2$) is 1.5 times greater than that compared to an equivalent sample under identical conditions without the cellulose and nanomaterial composition present. In some embodiments, the steady state evaporation rate is about 1.6 times greater, about 1.7 times greater, about 1.8 times greater, about 1.9 times greater, about 2.0 times greater, about 2.1 times greater, about 2.2 times greater, about 2.3 times greater, about 2.4 times greater, about 2.5 times greater, about 2.75 times greater, about 3.0 times greater, about 5 times greater, about 10 times greater, or about 15 times greater.

The evaporation efficiency of water comprising a BNC/RGO composition is a function of layered structure. In some embodiments the evaporation efficiency is greater than about 30%, greater than about 40%, greater than about 50%, greater than about 60%, greater than about 70%, greater than about 80%, greater than about 90%, or greater than about 95%.

The evaporation efficiency of water comprising a PDA/BNC composition is a function of layered structure. In some embodiments the evaporation efficiency is greater than about 30%, greater than about 40%, greater than about 50%, greater than about 60%, greater than about 70%, greater than about 80%, greater than about 90%, or greater than about 95%.

Aerogels have very low thermal conductivity due to their high degree of porosity. This acts as an insulating layer and reduces heat transfer from the surface of the liquid where the aerogel floats into the bulk liquid below thereby increasing heat localization at the surface of the liquid. In some embodiments, the porosity of at least one of the layers in the cellulose and nanomaterial composition is greater than about 60%, greater than about 65%, greater than about 70%, greater than about 75%, greater than about 80%, greater than about 85%, greater than about 90%, greater than about 95%, greater than about 96%, greater than about 97%, or greater than about 98%.

Figure 3A:
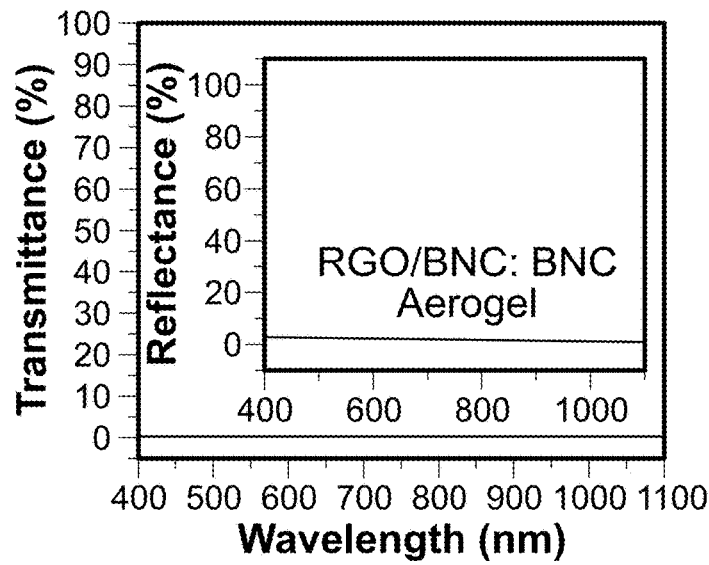
FIG. 3A is an exemplary embodiment of the transmittance and reflectance spectra of an RGO/BNC:BNC aerogel in accordance with the present disclosure.
Figure 3B:
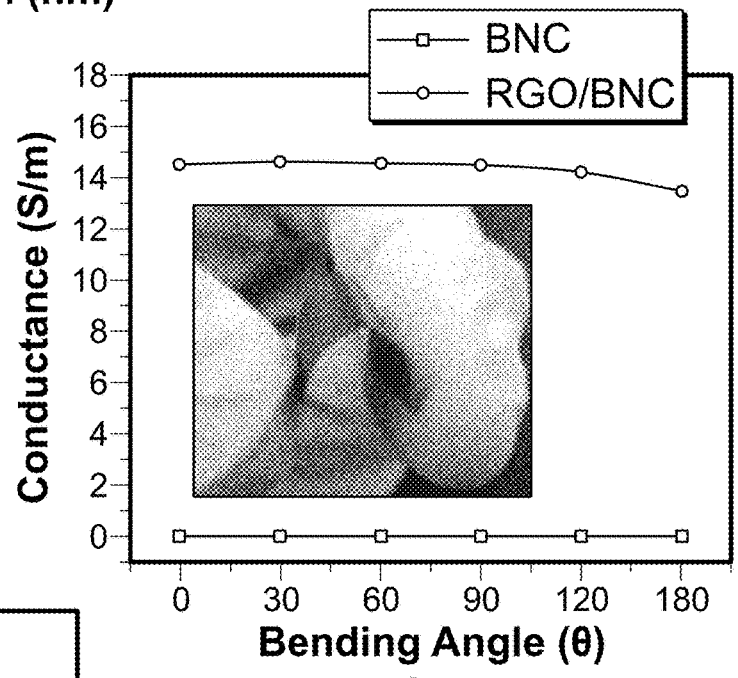
FIG. 3B is an exemplary embodiment of the conductance of an air-dried RGO/BNC:BNC film under various degrees of bending in accordance with the present disclosure.

In some embodiments, the composition is in the form of a bilayer comprising one layer of nanocellulose without a nanomaterial and one layer comprising nanocellulose and a nanomaterial. It (with a thickness of 2.1 mm) exhibits an extremely small optical transmittance (~1.5%) and reflectance (~2.5%) in the visible and near infrared regions, indicating the large optical extinction (~96%) of the bilayer (FIG. 3A). The large extinction of the composition owes to the optical absorption of the RGO flakes and the light scattering from the nanoscale cellulose fibers that increase the optical path length within the bilayer. Such large optical extinction of the bilayer structures combined with the excellent photothermal activity of RGO makes RGO/BNC:BNC excellent for solar steam generation. Natural drying of the RGO/BNC hydrogel (as opposed to freeze drying) resulted in the collapse of the 3D BNC structure into a flexible thin film. This bilayered thin film appeared light gray in color and exhibited a metallic luster, indicating the partial reduction of GO. The electrical conductivity of the thin film was measured on both sides (i.e., RGO/BNC and pristine BNC) under different bending angles (FIG. 3B). The pristine BNC exhibited extremely small electrical conductivity (~2.4× 10$^{-6}$ S/m) while the RGO/BNC exhibited significantly higher electrical conductivity (~14.5 S/m), which was found to be insensitive to the bending angle of the flexible film (inset of FIG. 3B). The electrical conductivity of the RGO/BNC film without any special reduction procedure was higher compared to a BNC/silk/multiwalled carbon nanotube (MWCNT) composite membrane (0.2 S/m) and a BNC/polyaniline (PANI) nanocomposite membrane (5 S/m), and was comparable to that of a previous BNC/RGO nanocomposite (23.8 S/m). The naturally dried composition exhibits a decreased steam generation efficiency compared to the freeze dried compositions; however the steam generation efficiency of the naturally dried composition is still greatly improved when compared to water with no cellulose/nanomaterial composition present. The naturally dried composition is still useful if freeze drying is not possible during production.

In some embodiments, bacteria are cultured in a bacterial growth media in the presence of a nanomaterial. In some embodiments, the nanomaterial is PDA, graphene oxide, reduced graphene oxide or a combination thereof. The amount of the nanomaterial is as described elsewhere herein. The bacterial growth media is selected based factors that promote optimal growth of the bacteria and the bacterial film. Those factors are known in the art. The bacteria is grown, for example, in an incubator or other suitable location in order to control temperature, humidity and other factors known in the art to affect bacterial growth. The composition is prepared by providing a bacterial culture in a media suitable for bacterial growth, dispersing a nanomaterial solution into said media, and incubating the bacteria for a predetermined time period or until the bacterial film achieves reaches a specific thickness. In some embodiments, the bacterial film is bacterial nanocellulose.

In some embodiments, the method of preparing the composition comprises forming a plurality of layers where each individual layer may or may not comprise a nanomaterial. When there are a plurality of layers, the nanomaterials may be the same or different than that in the adjacent layer or layers. In some embodiments, there are two layers where one layer comprises a nanomaterial and one layer does not comprise a nanomaterial.

In some embodiments, the bacterium is selected from the group consisting of *Gluconacetobacter hansenii* (ATCC 23769 or ATCC 53582), *Gluconacetobacter xylinus* (formerly named *Acetobacter xylinum*), *Escherichia coli, Agrobacterium tumefaciens, Acetobacter pasteurianus, Asaia bogorensis, Rhizobium* spp., *Sarcina ventriculli*, and *Gluconacetobacter sacchari*. Other bacteria that produce bacterial nanocellulose may be used also.

In some embodiments, the bacteria is grown under conditions suitable for bacterial grown for at least about one hour, at least about 1 day, at least about 2 days, at least about 3 days, at least about 4 days, at least about 5 days, at least about 6 days, at least about 7 days, at least about 10 days, at least about 14 days, at least about 21 days. Optionally, after a predetermined number of days, an additional aliquot of bacterial growth solution is added on top of the first biofilm layer. This is optionally repeated after a predetermined time period to create a film having a plurality of layers. The additional aliquots of bacterial growth solution may or may not have a nanomaterial at the same or different concentrations as the previous aliquots. The time period between the addition of additional aliquots may be the same or different as previous time periods and are selected independently from each other based on the desired characteristics of the biofilm.

In some embodiments, after bacterial growth and film formation, the film is harvested. In some embodiments the film is washed with a solvent. The solvent is at room temperature or any temperature up to, and including, the boiling temperature of the solvent. For example, the film may be washed with room temperature or boiling water. The solvent for washing may be pure water, or it may be acidic or basic. In some embodiments, the film is washed with a hot sodium hydroxide solution. One or more washings may be performed, and each wash solvent may be the same or different than other wash solvents, and the temperature may be the same or different than other washings.

In some embodiments, the harvested film is in the form of a hydrogel. The hydrogel may be washed with water that is neutral, acidic or basic one or more times. The washing may be at any temperature where the water remains a liquid up to, and including, boiling temperature. One or more washings may be performed, and each wash solvent may be the same or different than other wash solvents, and the temperature may be the same or different than other washings.

Harvesting of the bacterial film is done when a predetermined thickness is reached. In some embodiments the thickness is from about 0.1 to about 50 mm, from about 0.2 to about 45 mm, from about 0.5 to about 40 mm, from about 0.8 to about 35 mm, from about 1.0 to about 30 mm, from about 1.2 to about 25 mm, from about 1.5 to about 20 mm, from about 1.7 to about 15 mm, or from about 2.0 to about 10 mm.

In some embodiments, the harvested film is freeze dried. The freeze drying may be performed on the washed film or hydrogel or before the film or hydrogel is washed. Freeze drying is performed using standard techniques as are known in the art. The film or hydrogel may be cut into different sizes or shapes before or after freeze drying. Freeze drying may be before or after washing.

In some embodiments, the harvested film is naturally dried—as in placed in a location where the solvent present is permitted to naturally drain and/or evaporate. The temperature may be at any temperature up to, and including the boiling temperature of the solvent. In some embodiments, the solvent is water and the film is dried at ambient temperature. Drying may be before or after washing.

The harvested biofilm comprising nanocellulose and nanomaterial may also be dialyzed to remove residual growth media or other undesired components that may remain after washing. In some embodiments, the composition is dialyzed one or more times in water. The water may be deionized water, distilled water, double distilled water or nanopure water. The composition may be dialyzed one or more times, and the same or different water purity may be used each time. Each time the composition is dialyzed, the dialysis may last for from 30 minutes to five days with any increment of time in between. The time period and number of times for dialysis will be selected based on the degree of purity desired for the composition. A greater number of dialysis steps with a higher degree of water purity will result in a greater level of purity of the composition.

In some embodiments, the cellulose and nanomaterial composition disclosed herein is used to purify water. The water may be pure or impure, or the purity may not be known. "Impure" as used herein refers to water that is not suitable for human and/or animal consumption without purification. Examples of impure water include, but are not limited to, salt water (e.g., from the ocean), septic or sewage waste water, storm water runoff, or any other water that is not suitable for consumption by a human without purification or treatment. Examples of pure water include, but are not limited to, water from a faucet, a tap or a well that is suitable for human consumption without additional purification or treatment.

Because the density of a hydrogel or an aerogel is much less than most liquids, the composition will often float on the surface of the liquid. However the composition may have a higher or lower density than the liquid, or it may have neutral buoyancy. In some embodiments, the composition has a lower density than the liquid and floats.

In some embodiments, a method of heating water may be used to purify water in, for example, a desalinization process. Other uses for this method of heating water include the preparation of potable water that is suitable for human consumption wherein the liquid is an impure water source, including, but not limited to, salt water, brackish water, waste water, storm drain runoff, sewage treatment waste, river or lake water, contaminated water due to improper purification, contaminated water due to improper handling and/or transport. The preparation of potable water can be used after a natural occurrence when traditional safe water supplies have been compromised. In another embodiment, the preparation of potable water is used in rural or developing communities where access to safe drinking water supplies is limited.

Wood-Graphene Oxide Composite

Figure 11:
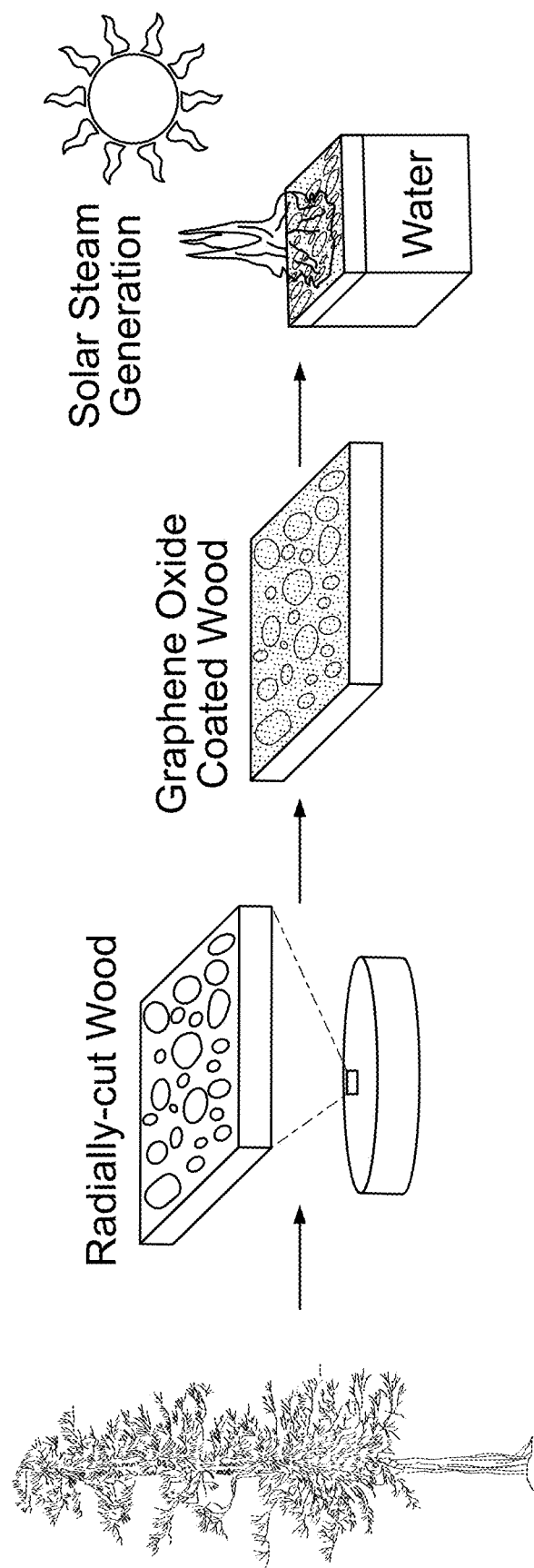
FIG. 11 is an exemplary embodiment of a schematic illustration depicting the fabrication of a wood-GO composite and set-up for solar steam generation in accordance with the present disclosure.
Figure 12A:
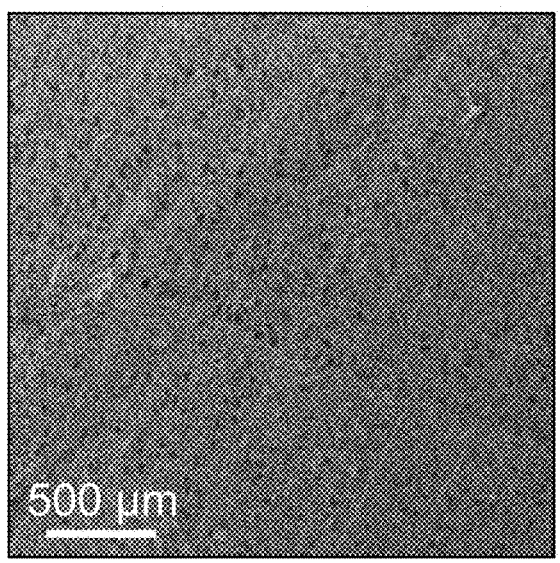
FIG. 12A is an exemplary embodiment of a low-magnification SEM image of a wood cross-section of the microchannel structures of wood in accordance with the present disclosure.
Figure 12B:
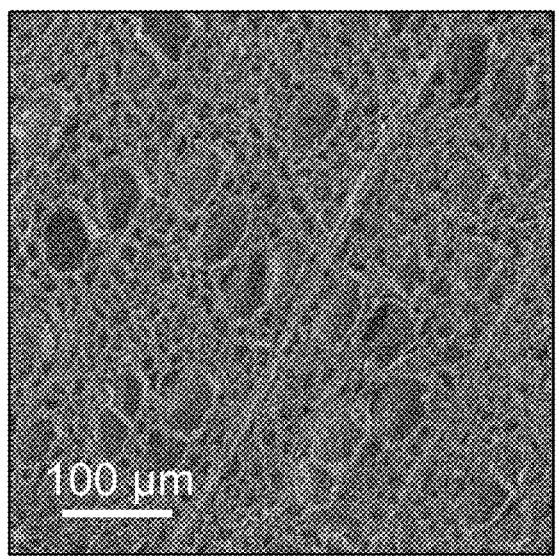
FIG. 12B is an exemplary embodiment of a high-magnification SEM image of a wood cross-section of the microchannel structures of wood in accordance with the present disclosure.
Figure 12C:
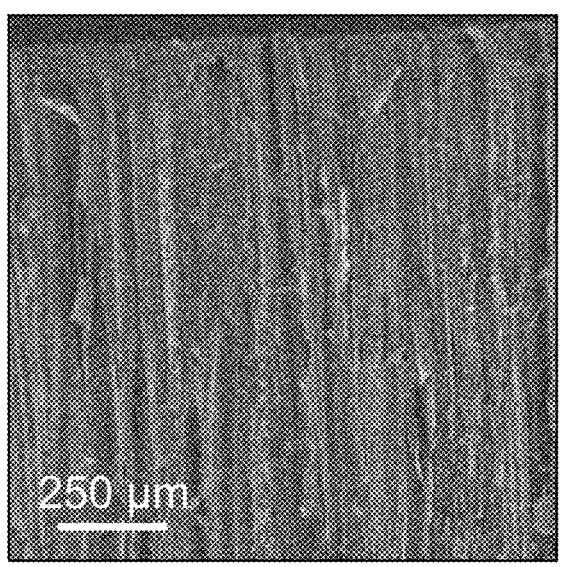
FIG. 12C is an exemplary embodiment of an SEM image of microchannels in wood in accordance with the present disclosure.
Figure 12D:
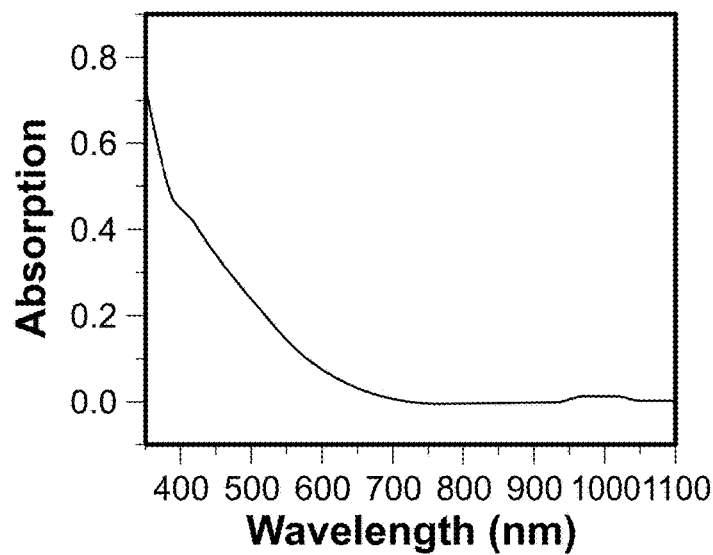
FIG. 12D is an exemplary embodiment of an absorption spectrum of radially-cut wood in accordance with the present disclosure.

Owing to its abundance, biocompatibility, and natural vessel structure, wood has attracted significant attention in various advanced applications including green electronics, biological devices, bioenergy and energy storage. The fabrication of wood-GO composite involves the deposition of GO flakes on the surface of a radially cut piece of wood (FIG. 11). SEM image of the top surface of the wood depicts the highly porous microstructure of wood (FIGS. 12A, 12B). Cross-sectional SEM image reveals long cylindrical microchannels with a diameter of a few tens of microns (FIG. 12C). It is known that wood cells (axial tracheids) exhibit cylindrical structure with a high aspect ratio and primarily run parallel to the trunk of the tree. These high aspect ratio microchannels combined with ray cells that run radially from the heartwood to the bark, form a continuous porous network that enables the transport of water and nutrients. This disclosure exploits the microchannel network in the wood to transport water from the bulk to the photothermally active layer at the evaporative surface. The extinction spectrum of the wood depicts the broad optical absorption in the visible part of the electromagnetic spectrum (FIG. 12D). The broad optical absorption of wood has an appreciable overlap with the solar spectrum causing a significant temperature under solar illumination.

Figure 12E:
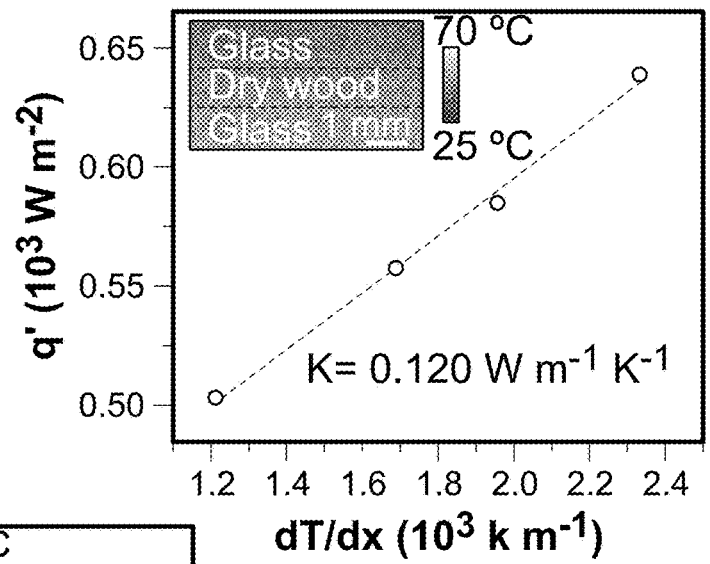
FIG. 12E is an exemplary embodiment of the thermal conductivity of wood in a dry-state.

A low thermal conductivity of the support layer is important to ensure confinement of the photothermally generated heat to the evaporative surface. To investigate the ability of wood to confine heat at the evaporative surface, the thermal conductivity of wood in both wet and dry states was determined. It was obtained using infrared images of wood sandwiched between two glass slides held at two different temperatures. The IR images of the wood show a gradient in the temperature along the thickness of the sample (inset of FIG. 12E). The thermal conductivity of wood in the dry state was found to be 0.120 W/m·K, which is higher than that of air (0.024 W/m·K at room temperature) and significantly lower than that of water (0.600 W/m·K) (FIG. 12E).

Figure 12F:
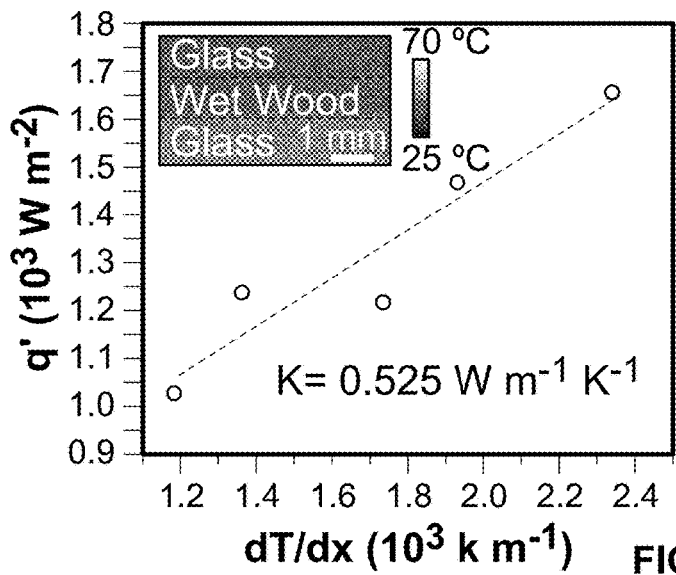
FIG. 12F is an exemplary embodiment of the thermal conductivity of wood in a wet-state. The insets in FIGS. 12E and 12F depict the temperature gradient along the thickness of wood in accordance with the present disclosure.

Wood as a support material with a low thermal conductivity, efficiently suppressed photothermal heat transfer to the bulk water and improve the solar steam generation efficiency. Since the wood is in a hydrated state during solar steam generation, the thermal conductivity in the wet state was determined. For the wet wood, the thermal conductivity was found to be 0.525 W/m·K (FIG. 12F), which is larger than that in the dry state but is still lower than the thermal conductivity of water and seawater. The thermal conductivity of wood in the wet state is comparable to the heat-insulating materials reported in recent literature for solar steam generation. This value is lower than an exfoliated graphite layer with water (0.959 W/m·K), which has been employed for solar steam generation.

Figures 13A, 13B:
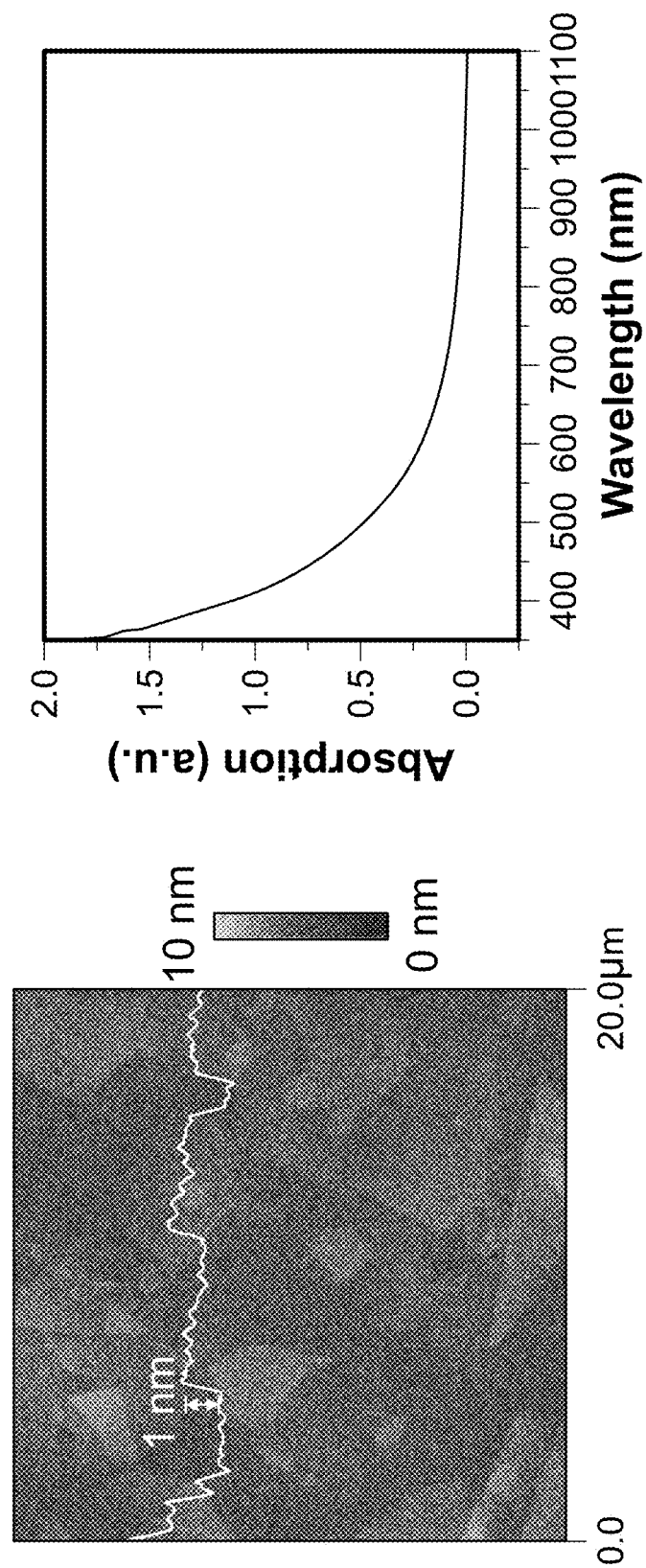
FIG. 13A is an exemplary embodiment of an AFM image of GO flakes deposited on a silicon substrate in accordance with the present disclosure.
FIG. 13B is an exemplary embodiment of an absorption spectrum of GO flakes dispersed in water in accordance with the present disclosure.

GO flakes were synthesized using a method reported by Tour and co-workers. Atomic force microscopy (AFM) image revealed the thickness of GO flakes deposited on a silicon substrate to be ~1.0 nm (FIG. 13A). The thickness of GO flakes corresponds to monolayer and bilayers of GO. The Raman spectrum of GO flakes revealed the characteristic graphite band (G-band) at ~1580-1600 $cm^{-1}$ and defect band (D-band) at ~1330-1350 $cm^{-1}$. GO flakes dispersed in water exhibited a broad optical absorption in the visible and NIR parts of the electromagnetic spectrum (FIG. 13B).

Figure 14A:
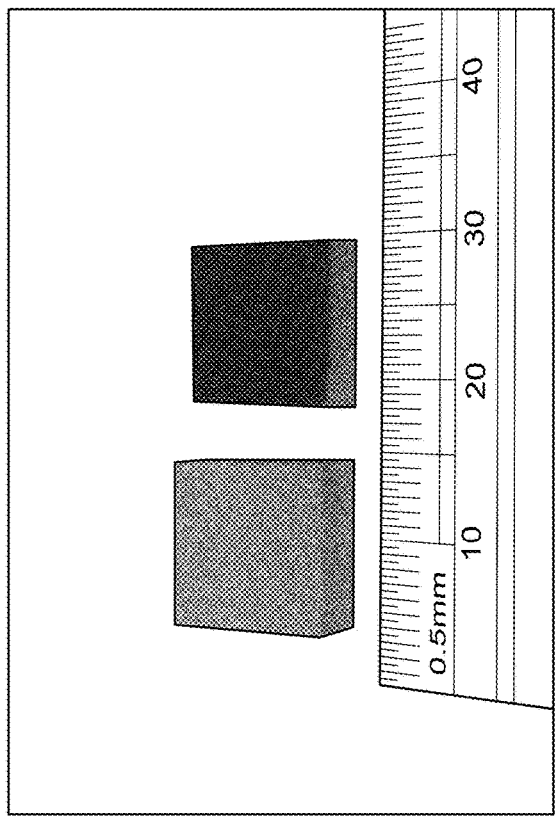
FIG. 14A is an exemplary embodiment of an optical image of wood with and without GO flakes in accordance with the present disclosure.
Figure 14C:
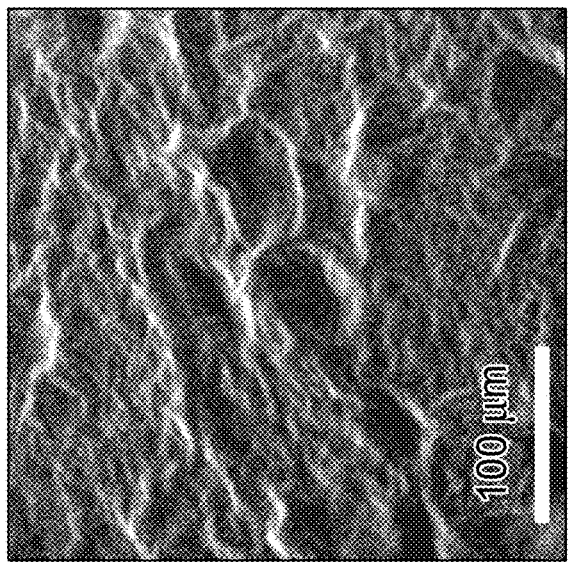
FIG. 14C is an exemplary embodiment of an SEM image of a wood cross-section with GO on the surface of the microporous structure in accordance with the present disclosure.
Figure 14B:
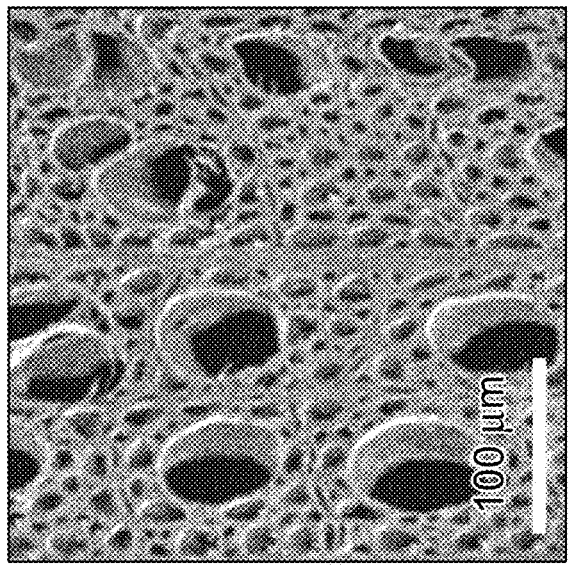
FIG. 14B is an exemplary embodiment of an SEM image of a wood cross-section without GO on the surface of the microporous structure in accordance with the present disclosure.
Figure 14E:
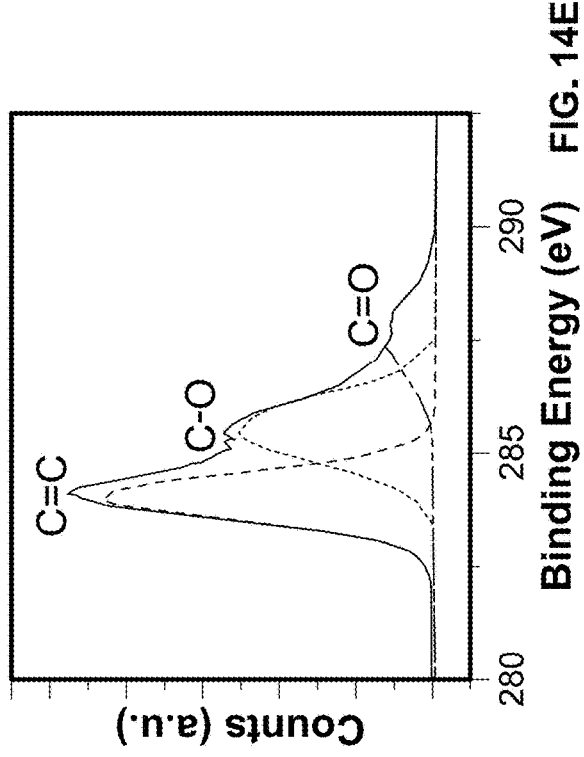
FIG. 14E is an exemplary embodiment of an XPS spectrum of wood in accordance with the present disclosure.
Figure 14D:
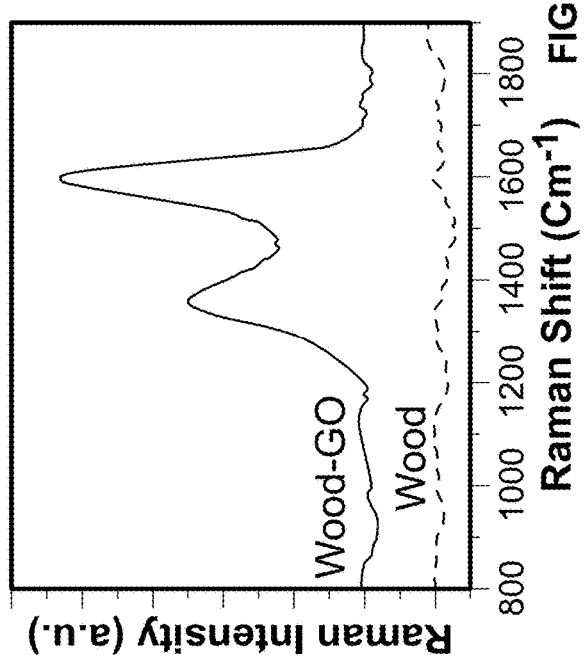
FIG. 14D is an exemplary embodiment of a Raman spectrum of wood with and without GO flakes coating on the surface in accordance with the present disclosure.
Figure 14F:
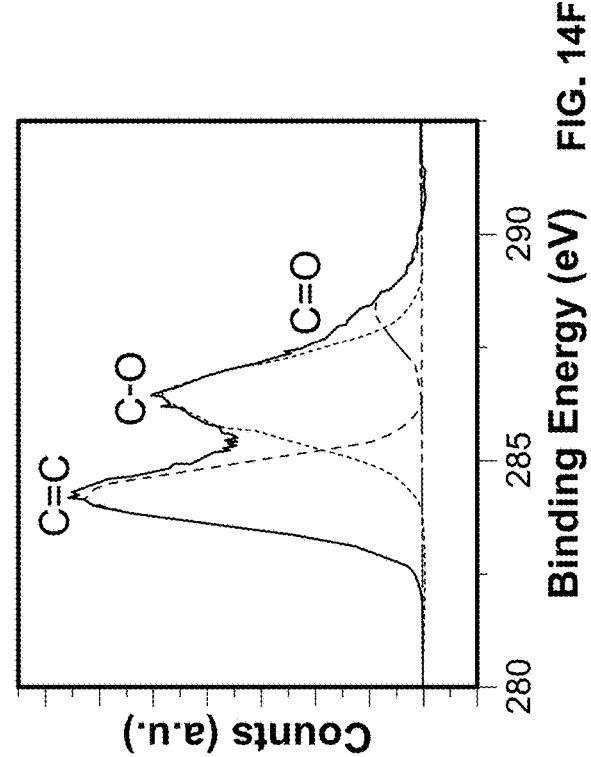
FIG. 14F is an exemplary embodiment of an XPS spectrum of a wood-GO composite in accordance with the present disclosure.

Wood-GO composites were prepared by depositing an aqueous GO solution on the surface of the wood followed by natural drying. Following deposition on the wood surface, the bilayered structure is evident from dark layer on the light colored wood (FIG. 14A). SEM images revealed the complete and conformal coverage of the microporous structure of wood with the GO layer (FIGS. 14B, 14C). The thickness of the GO layer was around 1.1 μm. It has been recently demonstrated that even for thick GO layers, an unimpeded permeation of water occurs through nanoscale pores, which has been employed for water filtration. This large permeation of the water is highly advantageous for solar steam generation when the GO layers are suspended on porous and thermally insulating support layers such as wood. Raman spectra of wood-GO composite revealed the characteristic G-band (~1580-1600 $cm^{-1}$) and D-band (~1330-1350 $cm^{-1}$) corresponding to GO (FIG. 14D). X-ray photoelectron spectroscopy (XPS) was employed to investigate the surface chemical composition of wood and wood-GO composite (FIGS. 14E, 14F). The is spectra of carbon was deconvoluted into three peaks corresponding to the $sp^2$ domains (C=C with a binding energy of 284.5-285 eV and the $sp^3$ domains (C—O with a binding energy of 286 eV and C=O with a binding energy of 288 eV). The C/O ratio obtained from the area under the peaks corresponding to $sp^2$ domains and oxidized $sp^3$ domains, show a decrease in the C/O ratio from wood sample (C/O=1.96) to wood-GO sample (C/O=1.90). The increase in the oxygen bearing groups at the surface confirmed the successful deposition of GO on the surface of the wood.

Figure 15A:
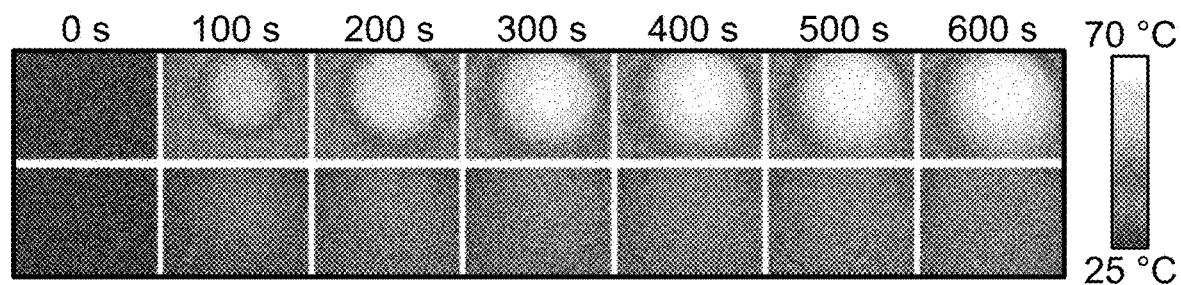
FIG. 15A is an exemplary embodiment of IR images showing the temperature of a wood-GO (top panel) and wood (bottom panel) under laser illumination in accordance with the present disclosure.
Figure 15B:
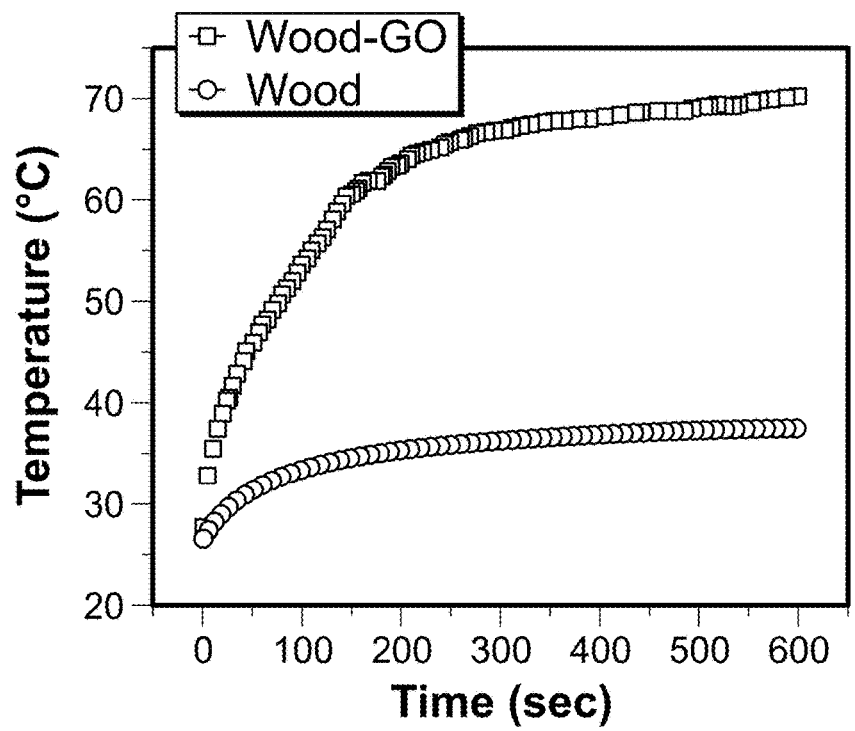
FIG. 15B is an exemplary embodiment of a plot showing the surface temperature of a wood-GO composite and wood under laser illumination in accordance with the present disclosure.

The photothermally induced temperature rise associated with wood and wood-GO under near-infrared (NIR) laser illumination (808 nm, power density of 5 $kW/m^2$) in a dry state (FIG. 15A) was investigated. Upon laser irradiation, the temperature of wood-GO rapidly increased from room temperature (27° C.) to around 70° C., while the temperature of wood reached around 37° C. under identical irradiation conditions (FIG. 15B). The large temperature rise of wood-GO ($\Delta T$=43° C.) compared to the relatively small increase in the temperature of wood ($\Delta T$=12° C.) upon laser irradiation demonstrates the high optical absorption and effective photothermal conversion efficiency of GO under NIR illumination.

Figure 15C:
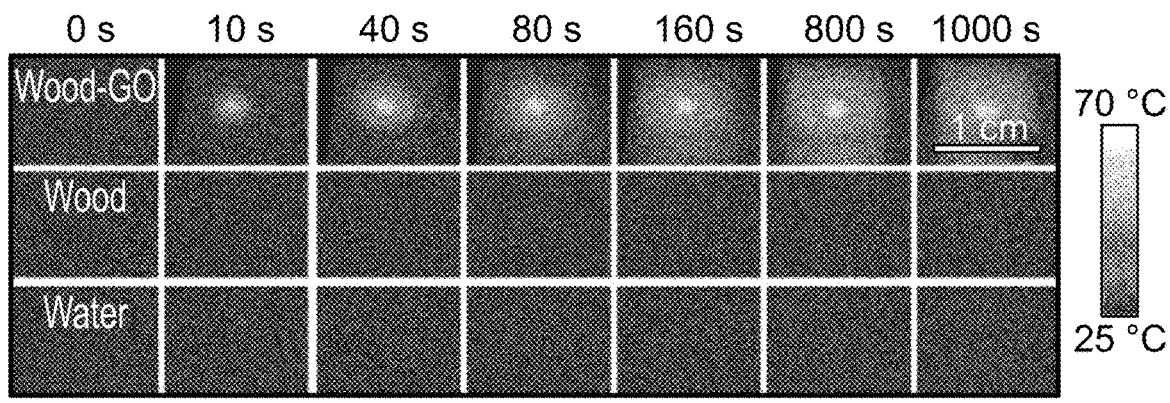
FIG. 15C is an exemplary embodiment of IR images of a wood-GO composite (top panel), wood (middle panel) and water under laser illumination in accordance with the present disclosure.
Figure 15D:
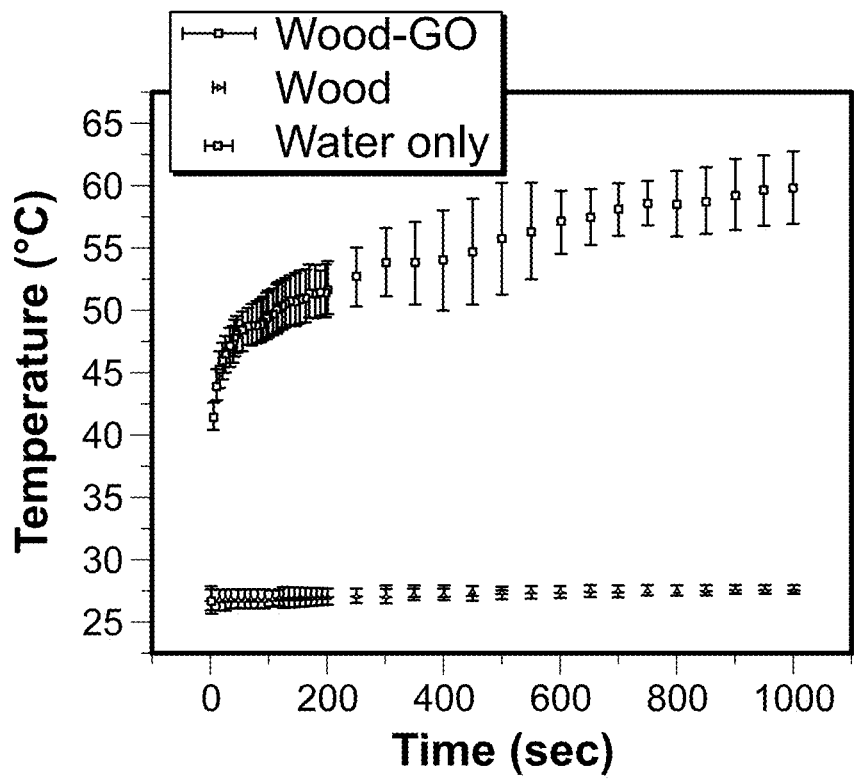
FIG. 15D is an exemplary embodiment of a plot showing the surface temperature of a wood-GO composite, wood and water under laser illumination in accordance with the present disclosure.
Figure 15E:
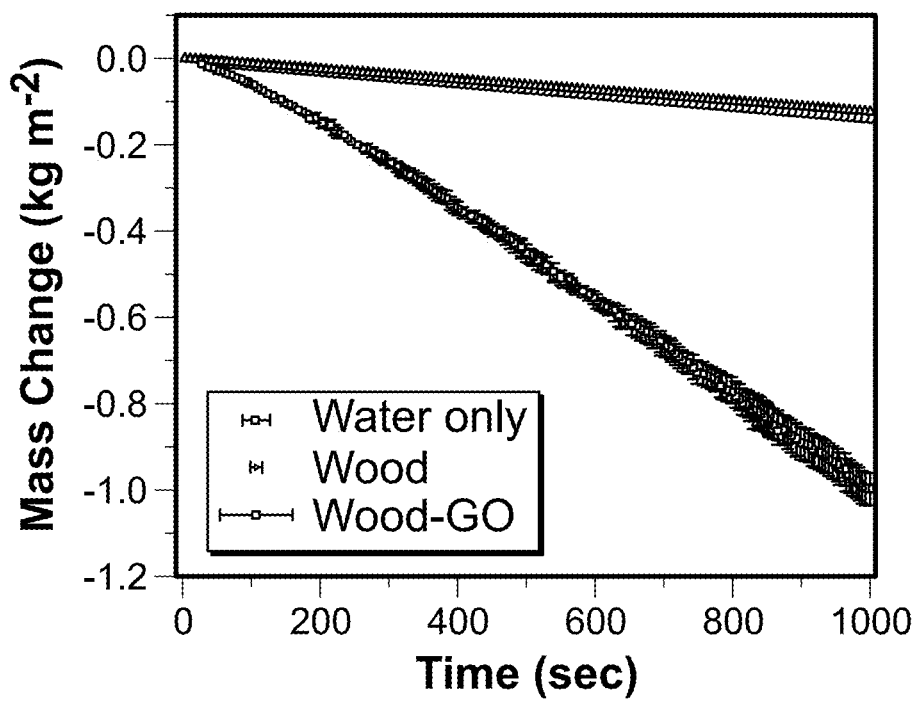
FIG. 15E is an exemplary embodiment of a plot showing cumulative mass change through water evaporation for a wood-GO composite, wood and water under laser illumination in accordance with the present disclosure.

Additionally, the photothermal activity of wood-GO in the wet state was investigated because the wood-GO composite is in a hydrated state during solar steam generation. IR images reveal the temperature of the wood and wood-GO floated on the surface of water under 808 nm laser illumination (power density of 5 $kW/m^2$) at various time points (FIG. 15C). Upon laser irradiation, the temperature of wood-GO floating on water rapidly increased from room temperature (27° C.) to around 60° C. (FIG. 15D). In comparison, the temperature of wood and water did not exhibit a significant increase within an irradiation time of 1000 sec (FIG. 15D). The mass change of water as a function of irradiation time was employed to quantify the steam generation efficiency of the wood-GO composite and wood. Over 1000 sec laser irradiation, the mass change of water from wood-GO floated on water was found to be around 1 $kg/m^2$, which is nearly seven times higher compared to that observed for wood on water (0.14 $kg/m^2$) and water (0.12 $kg/m^2$) (FIG. 15E). This was significantly higher steam generation efficiency of wood-GO composite compared to wood stems from the higher NIR light absorption of GO compared to wood, with the latter predominantly absorbing in the visible part of the electromagnetic spectrum (as shown in FIG. 13B).

Figure 16A:
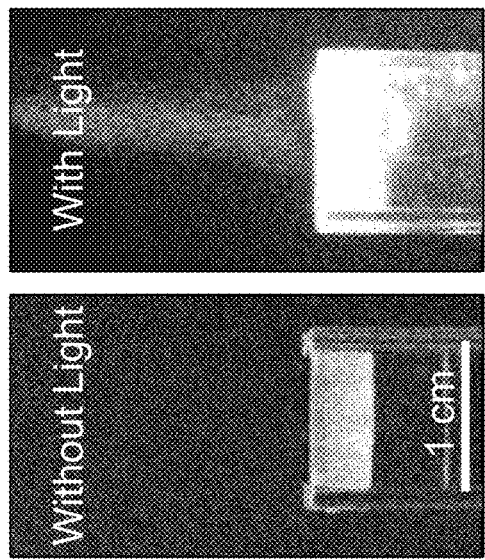
FIG. 16A is an exemplary embodiment of IR images showing the temperature of a wood-GO composite floated at an air/saline interface under solar illumination in accordance with the present disclosure.
Figure 16B:
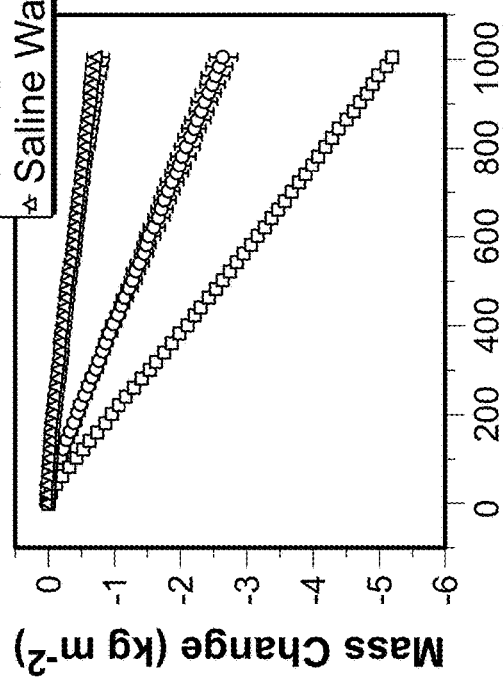
FIG. 16B is an exemplary embodiment of optical images of a wood-GO composite floated at an air/saline water interface and steam generation under solar illumination in accordance with the present disclosure.

To evaluate the steam-generation efficiency and the desalination ability of wood-GO composite under simulated solar illumination (power density of 12 $kW/m^2$), the weight loss of saline water due to the water evaporation (3% salinity) was measured (FIGS. 16A-16D). GO flakes exhibit a broad optical absorption over visible and NIR parts of the electromagnetic spectrum. Combined with the absorption of wood in the visible region, the large temperature rise of the wood-GO composite under simulated solar illumination resulted in the appearance of steam above the cuvette, which signifies the rapid evaporation of water (FIGS. 16A, 16B).

Figure 16C:
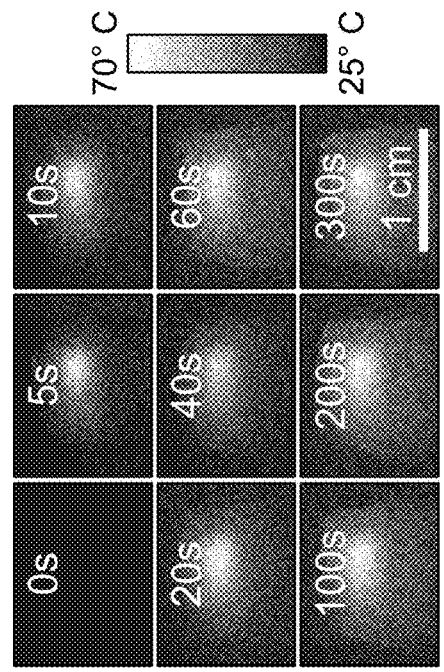
FIG. 16C is an exemplary embodiment of a plot showing the surface temperature of a wood-GO composite, wood and saline water under solar illumination in accordance with the present disclosure.

The temperature of the wood-GO composite rapidly increased from room temperature to around 67° C. within tens of seconds after the onset of simulated solar irradiation and remained constant over the remaining irradiation time (FIG. 16C). In the case of pristine wood (i.e. in the absence of GO layer), the temperature raised from 27° C. to 54° C. Compared to 808 nm laser, the larger temperature rise for pristine wood under simulated solar illumination may be attributed to the higher optical absorption of wood in the visible part of the electromagnetic spectrum that exhibits a large significant overlap with the solar spectrum. On the other hand, the temperature rise of saline water itself was found to be significantly smaller ($\Delta T=\sim10°$ C.).

Figure 16D:
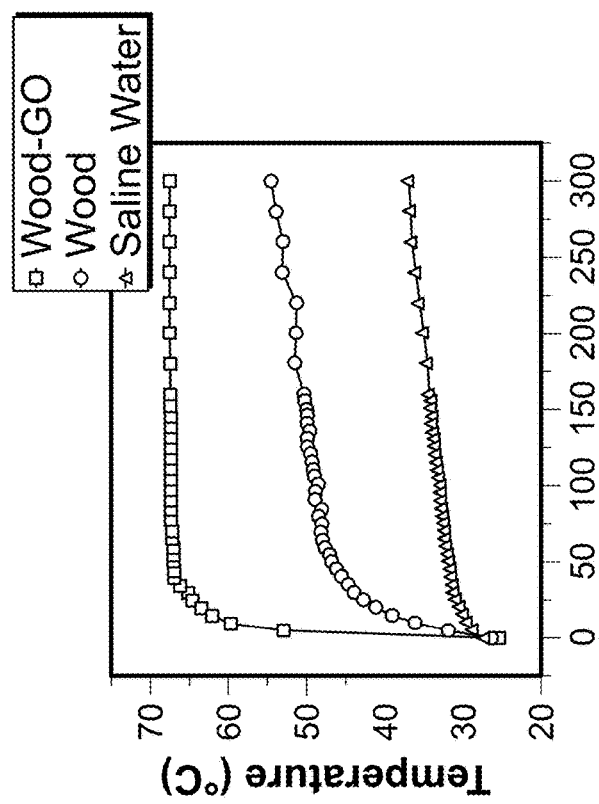
FIG. 16D is an exemplary embodiment of a plot showing cumulative mass change through water evaporation of a wood-GO composite, wood and saline water under solar illumination in accordance with the present disclosure.

Under solar illumination, the cumulative weight loss was found to increase linearly with the irradiation time (FIG. 16D). The weight loss over a duration of 1000 s was found to be 5.2 kg/m$^2$ for wood-GO composite. Over 200 s of solar irradiation, the steady-state evaporation rate was calculated to be 14.02 kg/m$^2$·h for wood-GO composite. In the case of pristine wood, the steady-state evaporation rate was calculated to be 10.08 kg/m$^2$·h. Without considering the optical concentration losses in the analysis, such as surface radiation and reflection, the evaporation efficiency of the wood-GO composite was calculated to be 82.8% at a power density of 12 kW/m$^2$. In the case of pristine wood, the evaporation efficiency was found to be around 59.5%. These results demonstrate the excellent photothermal capabilities of wood-GO composite and its application in solar steam generation.

Figure 17A:
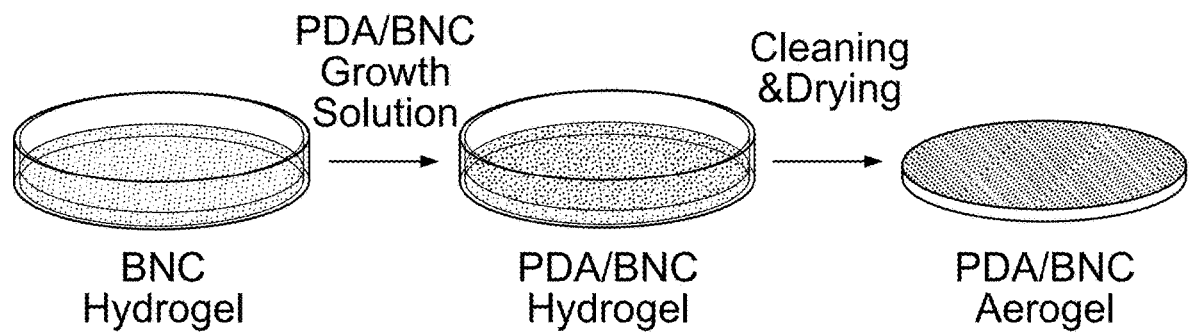
FIG. 17A illustrates the fabrication of a PDA/BNC hydrogel.
Figure 17B:
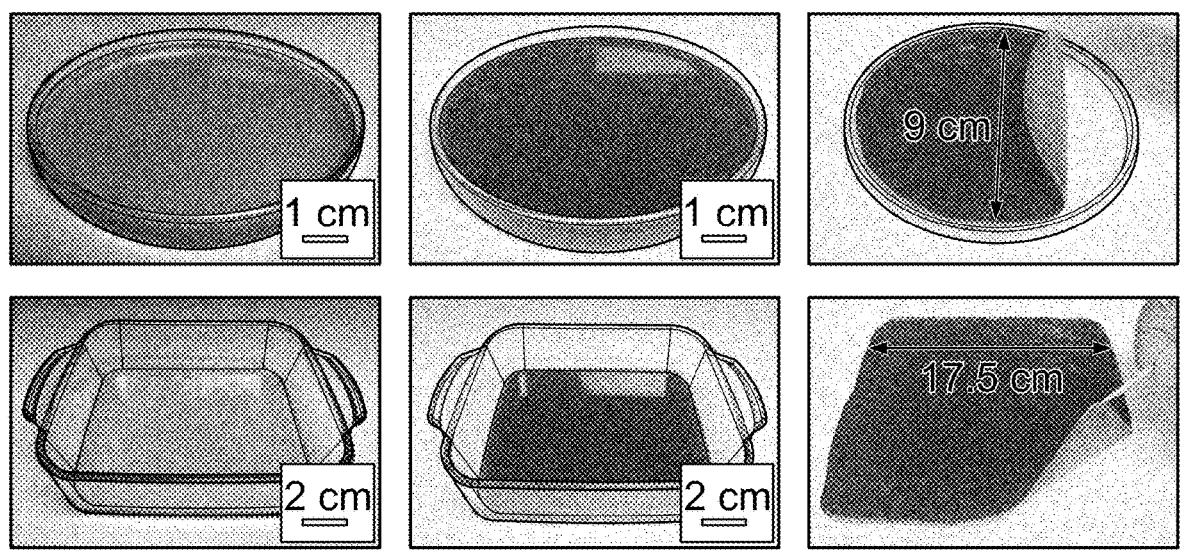
FIG. 17B illustrates the PDA/BNC hydrogel with tunable sizes and shapes.
Figure 18A:
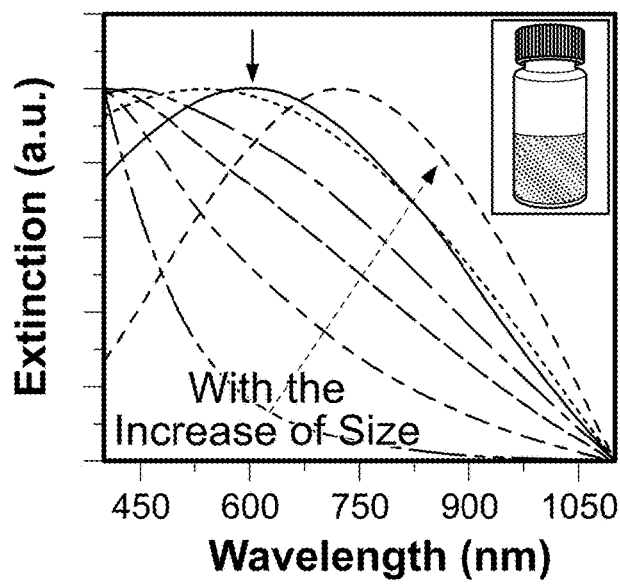
FIG. 18A is the Vis-NIR extinction spectra of PDA particles with varying sizes (inset is the photograph of PDA particles solution.
Figure 18B:
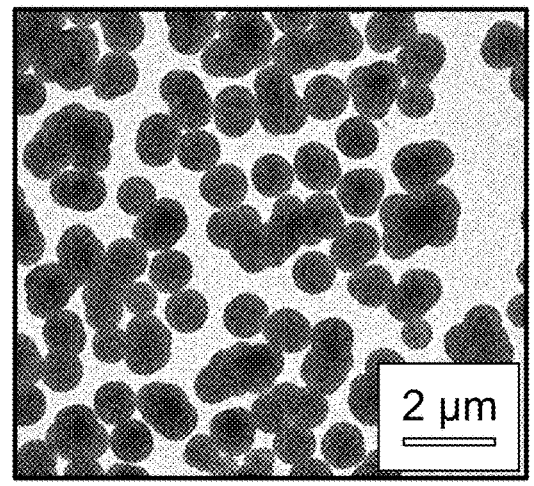
FIG. 18B is the TEM image of PDA particles.
Figure 18C:
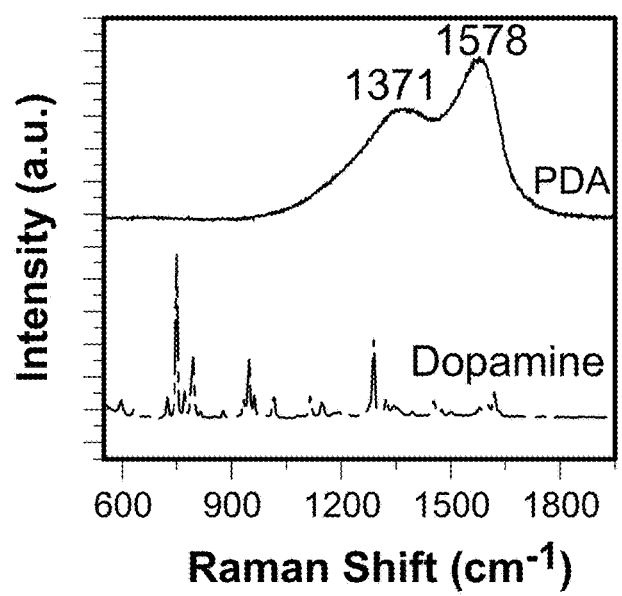
FIG. 18C is the Raman spectra of Dopamine and PDA.
Figure 18D:
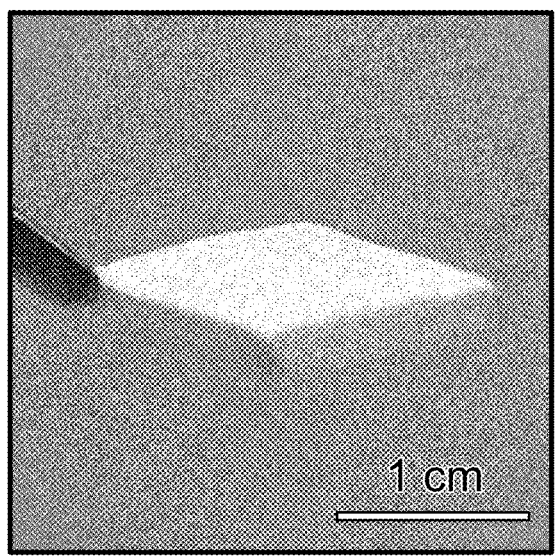
FIGS. 18D and 18E are optical and SEM images of the surface (inset is the image of higher resolution) and cross-section (FIG. 18F) of a pristine BNC foam.

In yet another aspect, the fabrication of and interfacial solar steam generator with desired size and shape involves a two-step BNC growth under aerobic and static growth conditions (FIG. 17 and Example 8). PDA particles were obtained using a method reported by Lu and co-workers, infra, through oxidation and self-polymerization of dopamine monomers in a mixture of water, ethanol and ammonia at room temperature. The size of PDA particles, which alters the optical properties, was tuned by varying the ratio of ammonia to dopamine monomers. The size of the PDA particles was optimized to efficiently trap PDA particles within the BNC fiber matrix and to ensure significant overlap between the optical absorption of the PDA particles and the solar spectrum in the visible and near infrared region (FIG. 18A). Transmission electron microscopy (TEM) and scanning electron microscopy (SEM) images revealed that the PDA particles were spherical in shape with a diameter of $\sim 1$ μm (FIG. 18B). Dynamic light scattering (DLS) also revealed the hydrodynamic size of the PDA particles to be $\sim 1$ μm. Raman spectrum of dopamine monomers showed characteristic bands of C—C stretching (724, 948, 1324, and 1422 cm-1), C—O stretching (1290 cm-1), and C—N stretching (795 cm-1). The Raman spectrum of PDA particles exhibited two broad bands (1371 and 1578 cm-1), suggesting catechol deformation. This provides an additional confirmation of successful PDA particles synthesis (FIG. 18C).

Figure 18E:
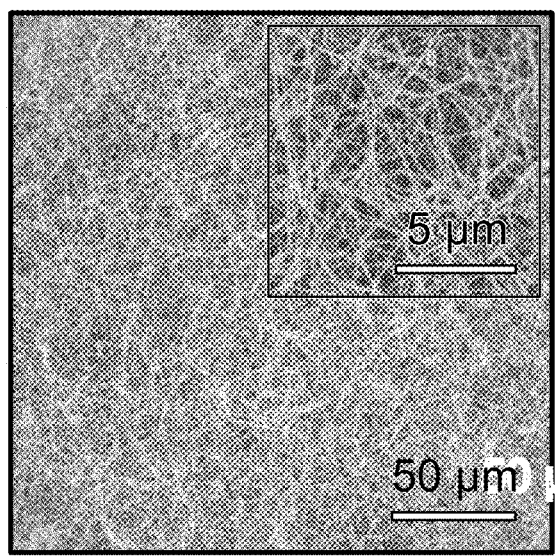
Figure 18F:
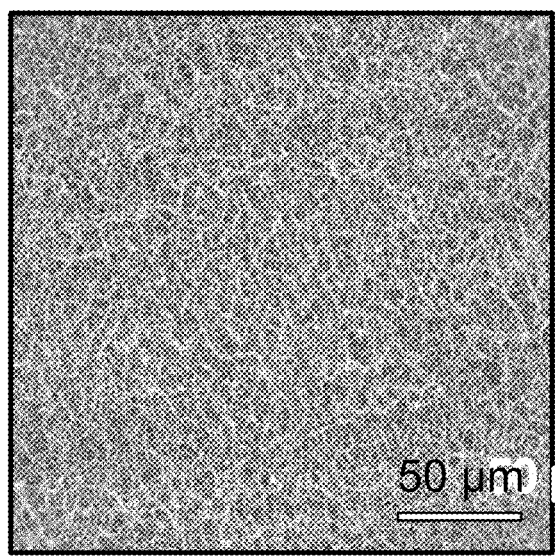
FIGS. 18G and 18H are optical and SEM images of the surface (inset is the image of higher magnification) and cross-section (FIG. 18I) of a PDA/BNC foam.
Figure 18G:
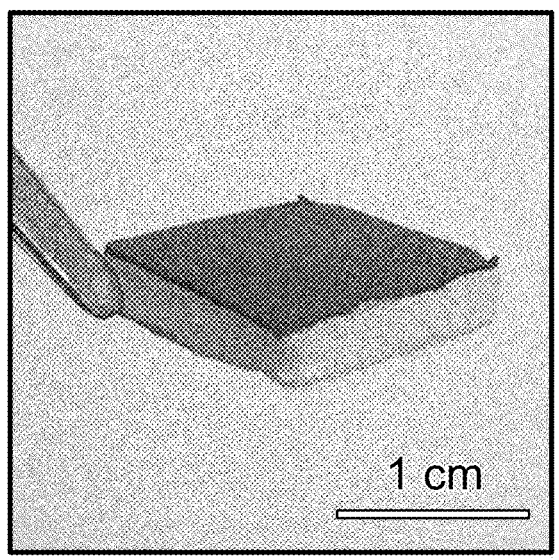
Figure 18H:
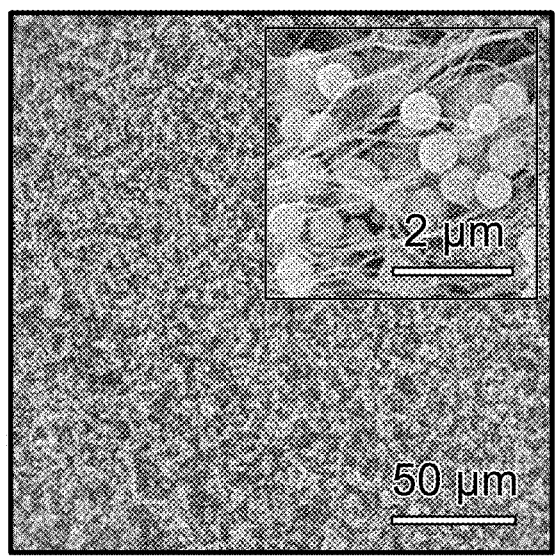
Figure 18I:
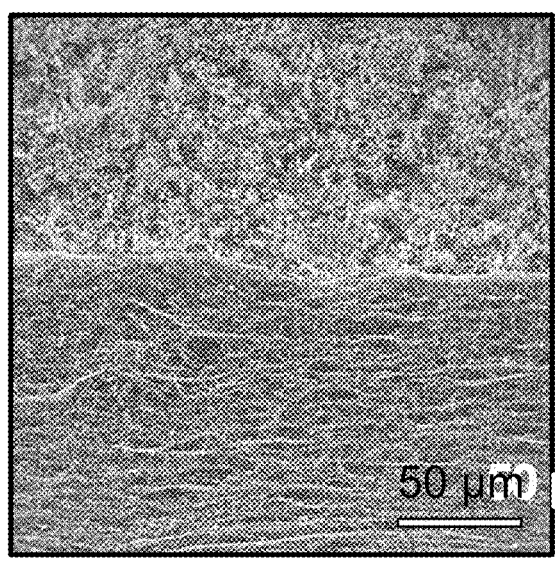
Figure 19A:
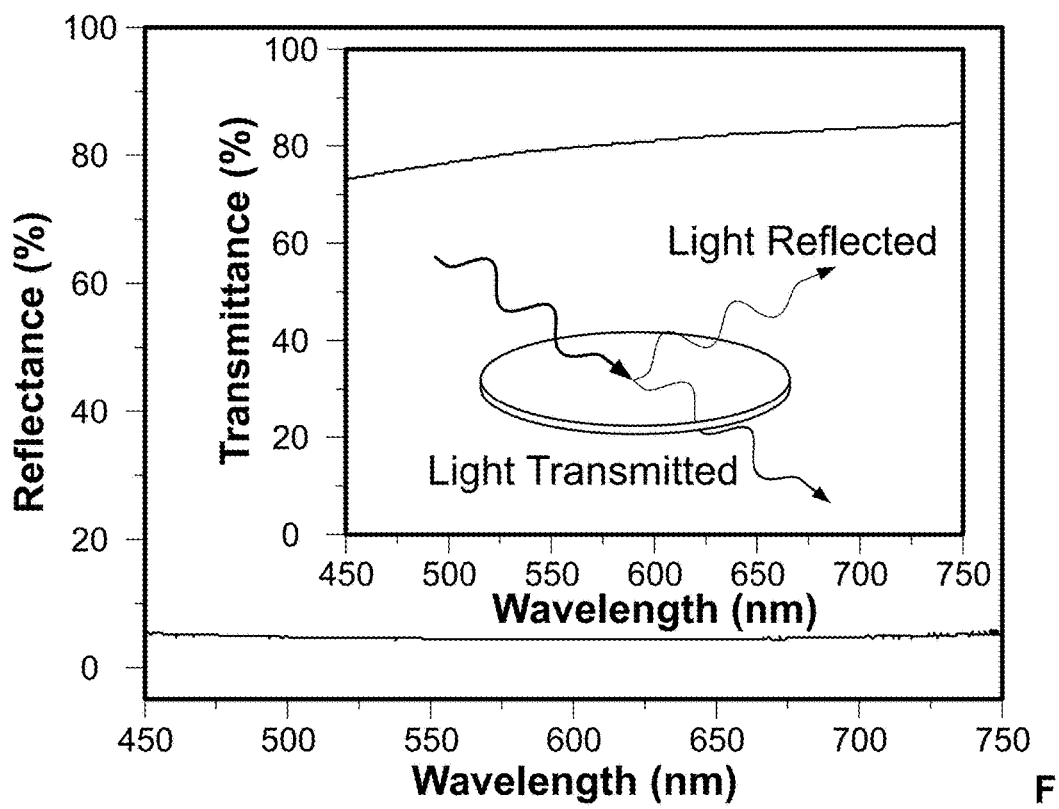
FIG. 19A is an exemplary embodiment of the transmittance and reflectance spectra of a BNC hydrogel.
Figure 19B:
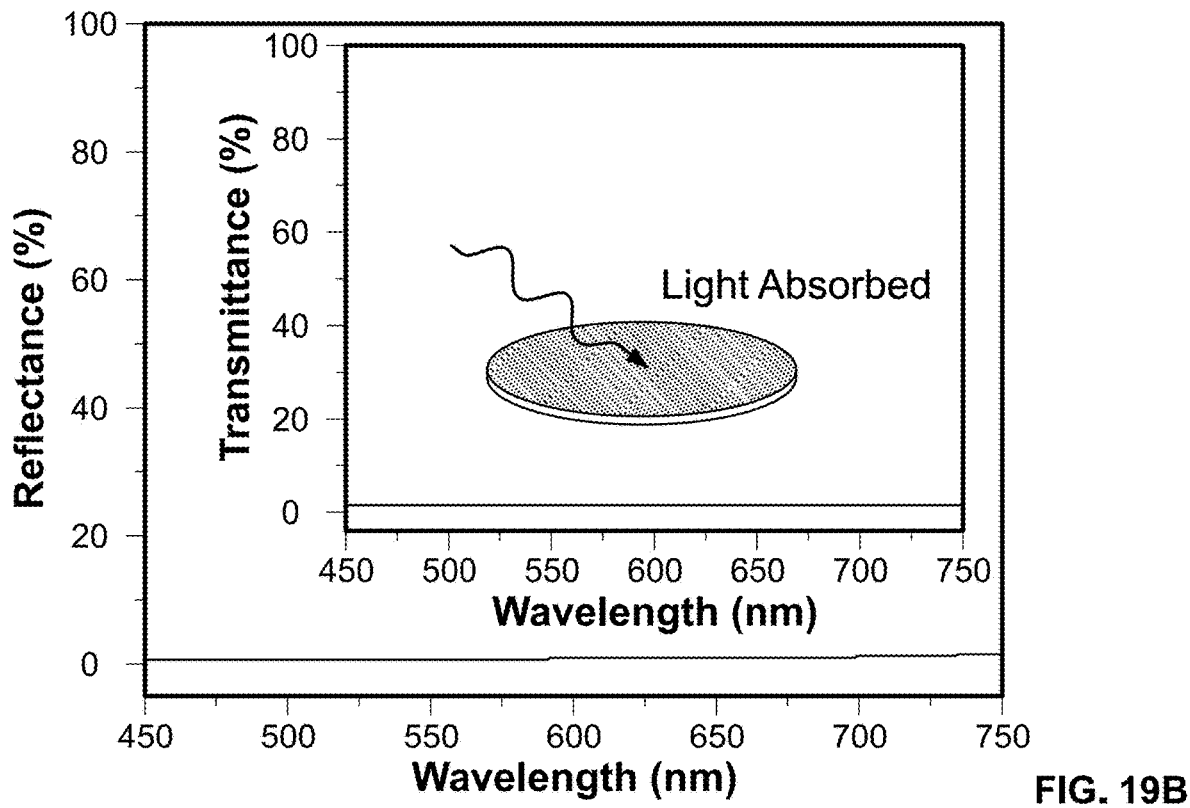
FIG. 19B is the transmittance and reflectance spectra of a PDA/BNC hydrogel.
Figure 19C:
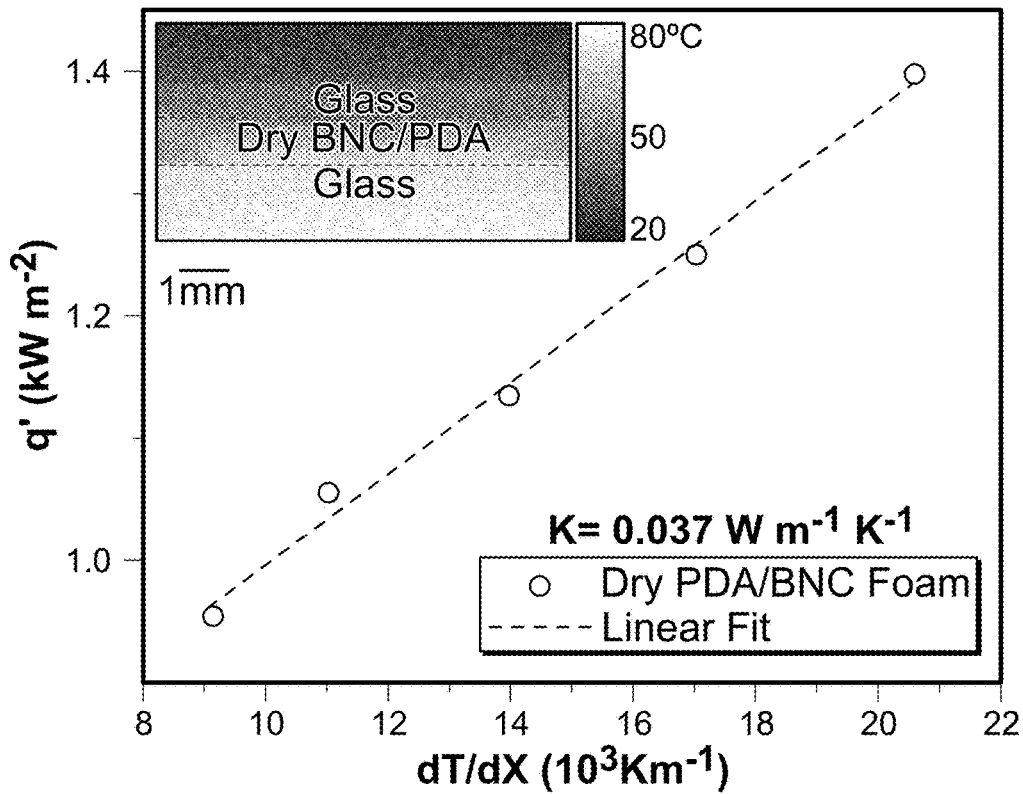
FIGS. 19C and 19D are the thermal conductivities of dry PDA/BNC foam and wet PDA/BNC hydrogel. Insets in FIGS. 19C and 19D are representative IR images showing the temperature gradient along the thickness of the samples.
Figure 19D:
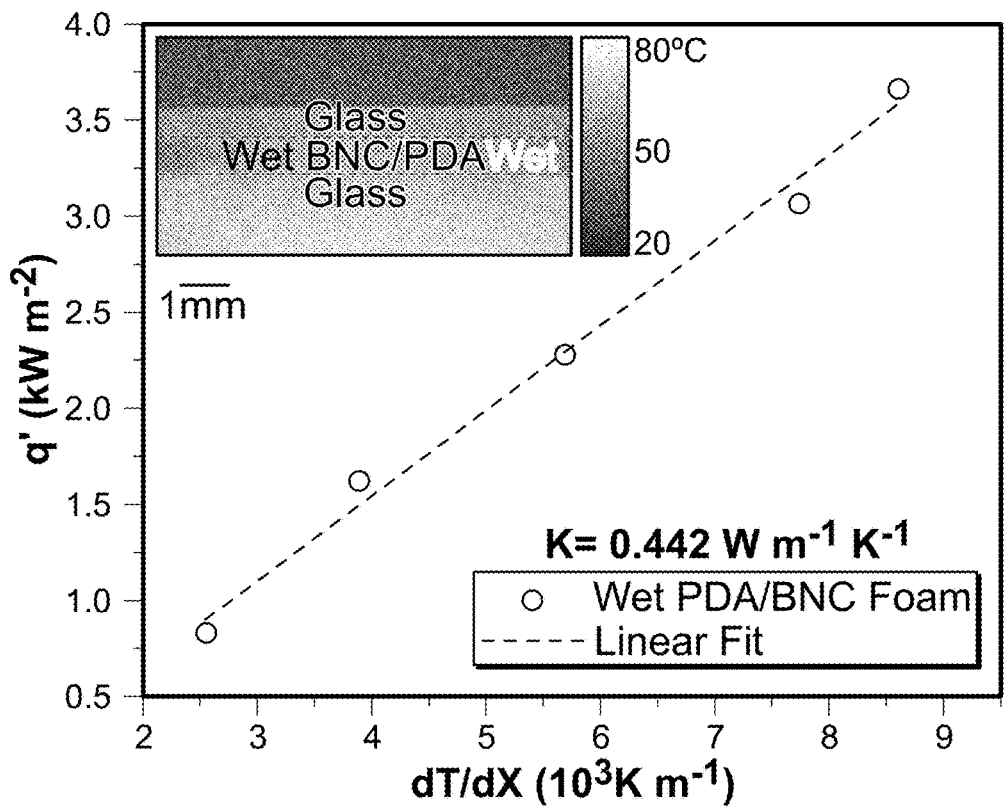
Figure 23:
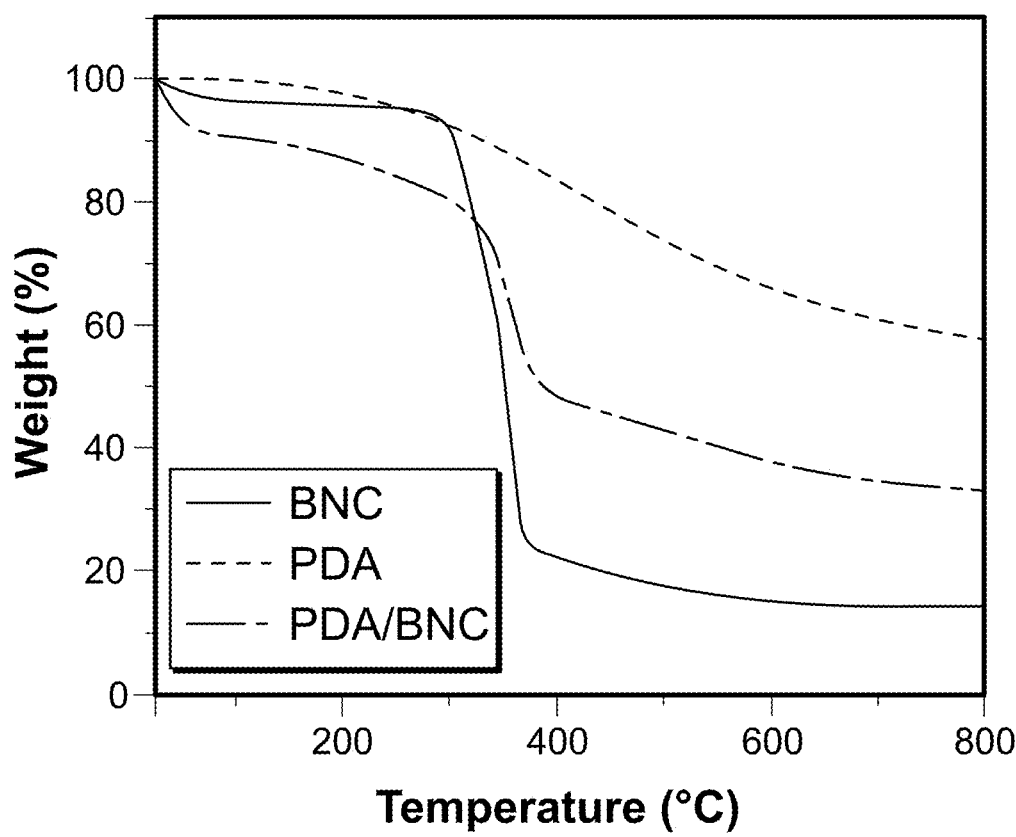
FIG. 23 is the thermogravimetric analysis of pristine BNC, pristine PDA, and PDA/BNC.
Figure 24A:
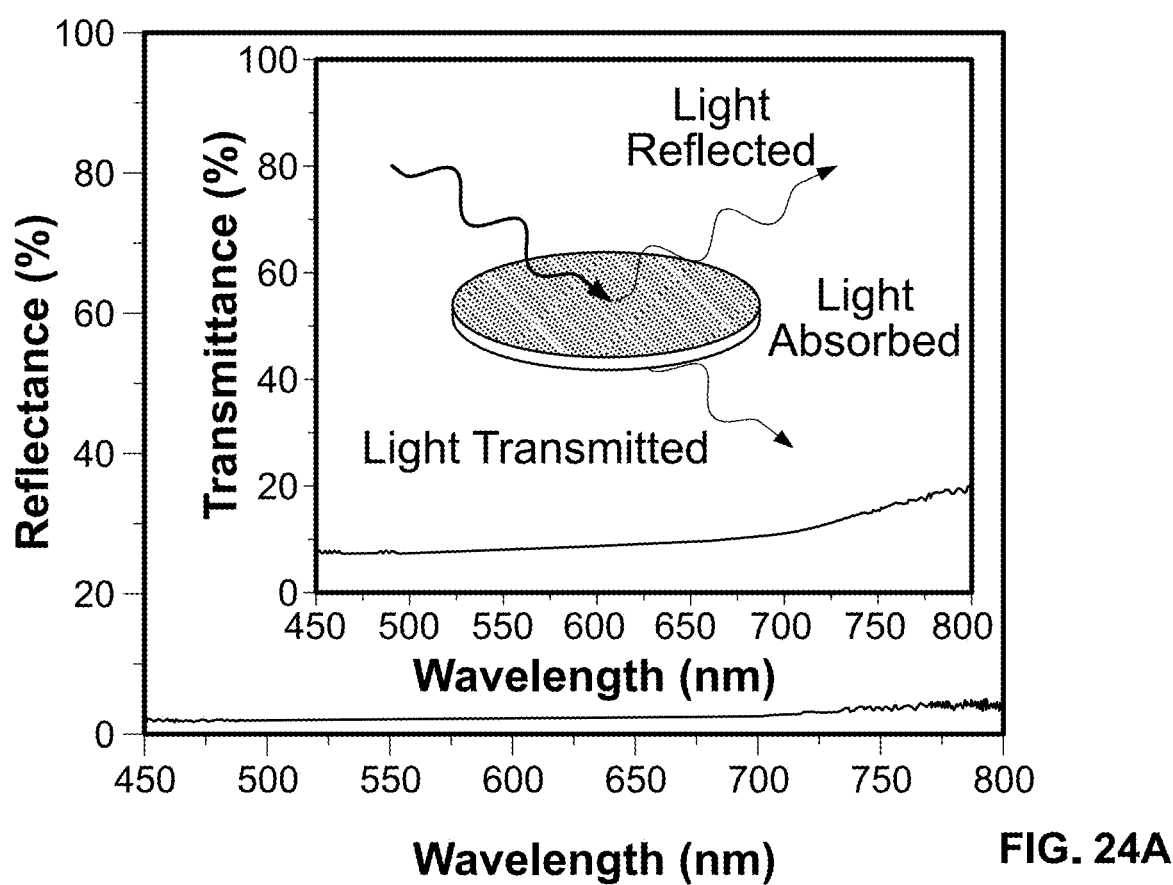
FIG. 24A is the transmittance and reflectance spectra of PDA coated BNC hydrogel.
Figure 24B:
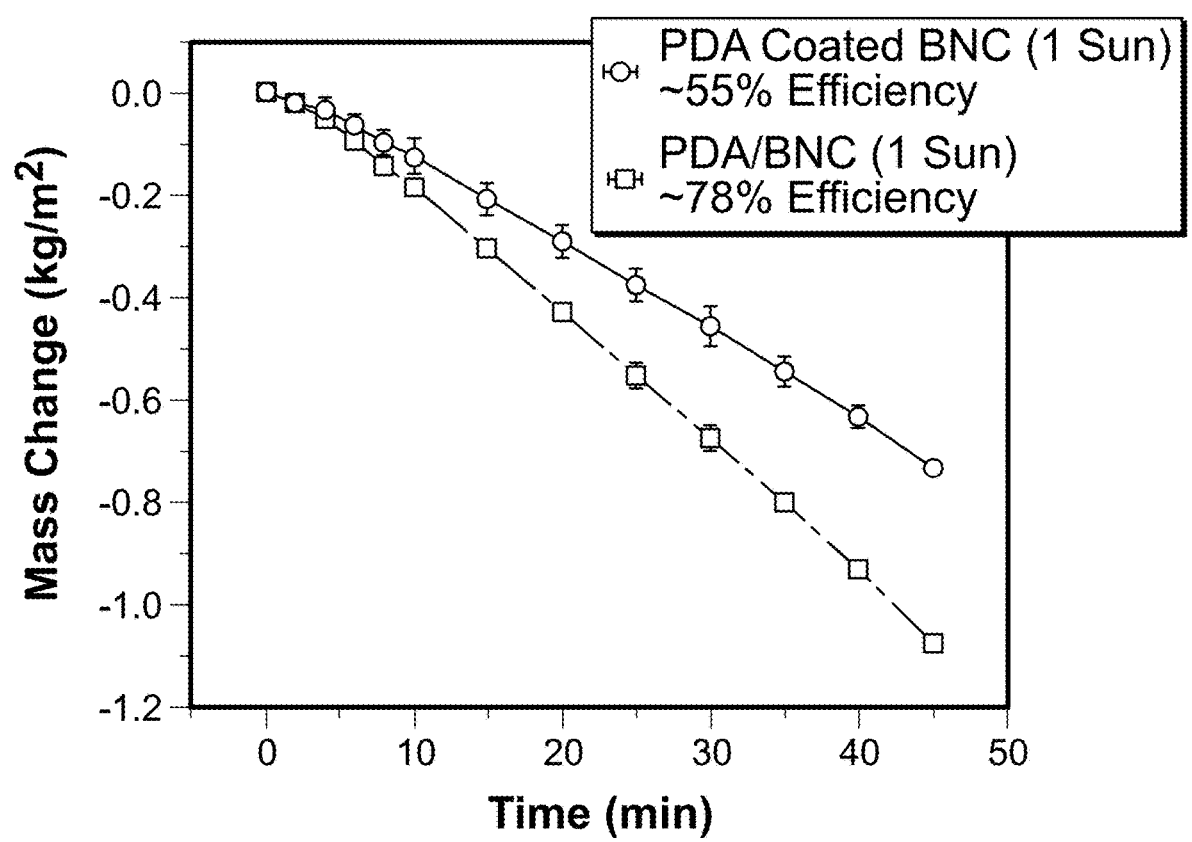
FIG. 24B is a graph of the solar steam generation performance of PDA-coated BNC compared with PDA/BNC via in situ growth method.
Figure 25:
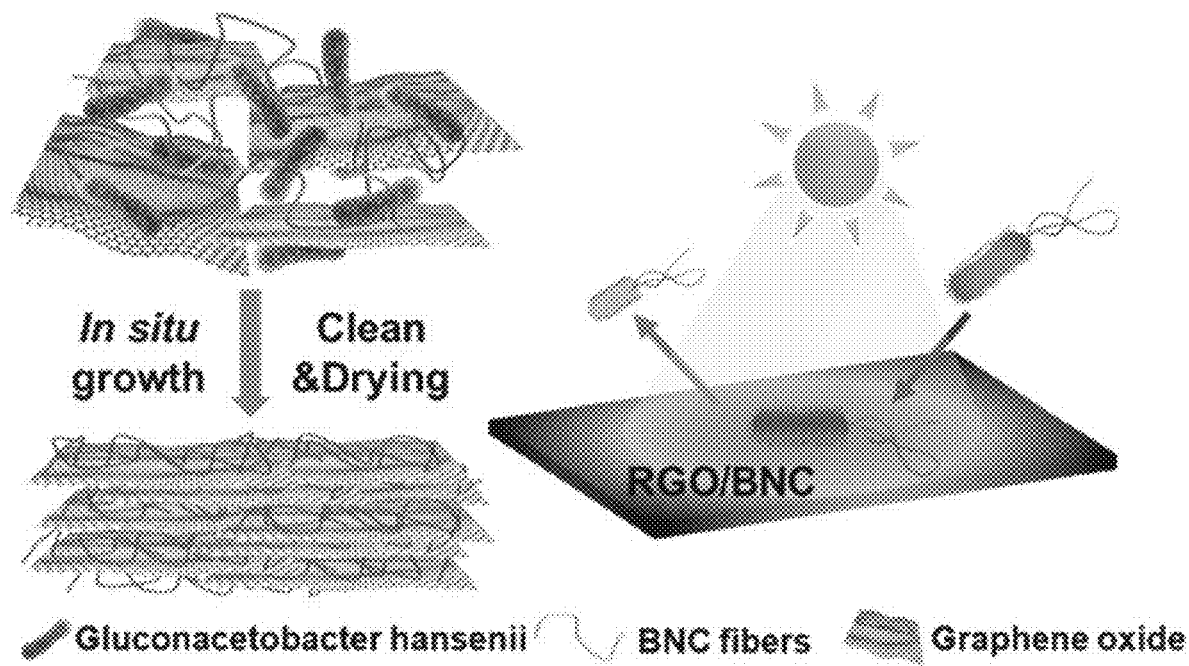
FIG. 25 is an exemplary embodiment of an RGO/BNC membrane in accordance with the present disclosure.

Pristine BNC aerogel exhibited $\sim 98\%$ porosity, ultralow density ($\sim 20$ kg/m$^3$) and extremely large specific surface area (FIG. 19D). Furthermore, BNC aerogel forms a highly open microporous non-woven 3D network of cellulose nanofibrils (diameter of 20-100 nm) with highly abundant hydroxyl groups, promoting high hydrophilicity (FIG. 18E, FIG. 18F). Thus, the nature of the BNC aerogel facilitates the transport of water to the evaporative surface, making it as an ideal supporting material for an interfacial solar steam generator. The bilayered structure of PDA/BNC was achieved by growing a thin BNC layer ($\sim 100$ μm) with PDA particles on top of a thick pristine BNC hydrogel ($\sim 4$ mm, as a heat insulation and water transport layer) (FIG. 18G). As the bacteria produces a dense entangled layer of cellulose fiber network at the air/bacteria-growth medium interface, the high density of PDA particles may be loaded within the top layer, as shown in the surface and cross-sectional SEM images (FIG. 18H, FIG. 18I). A cross-sectional SEM image also shows the sharp interface between the PDA-loaded and pristine BNC layers. Thermogravimetric analysis determined that the loading of PDA particles to be around 43% (FIG. 23).

To evaluate the light absorption properties of PDA/BNC, the optical transmittance and reflectance of BNC and PDA/BNC was measured. Pristine BNC hydrogel ($\sim 4$ mm) showed high transmittance ($\sim 80\%$) and reflectance ($\sim 4.8\%$) in the visible region, which translates to relatively small light extinction ($\sim 15.2\%$) (FIG. 19A). On the other hand, the PDA/BNC hydrogel (with thickness of $\sim 4.1$ mm) exhibited extremely small optical transmittance ($\sim 1.2\%$) and reflectance ($\sim 0.96\%$) in the visible region, indicating a large optical extinction ($\sim 98\%$) of the bilayer (FIG. 19B). The large light extinction of the PDA/BNC results from the light absorption corresponding to the densely loaded PDA particles and the light scattering from the nanoscale cellulose fibers, which increases the optical path length within the bilayer.

PDA adheres to a broad range of materials with widely different surface chemistries. It is possible to coat PDA on BNC via self-polymerization under oxidative condition in order to prepare a PDA/BNC interfacial solar evaporator. After five polymerization cycles (each for over 12 hours), the PDA/BNC hydrogel exhibited a light extinction of $\sim 87\%$ (FIG. 23). The coating process via polymerization results in a thin layer of PDA on the nanofibers of the highly porous BNC. The lower amount of PDA in the PDA-coated BNC compared to that in PDA particle-filled BNC results in a lower light extinction of the former compared to the latter.

Figure 20A:
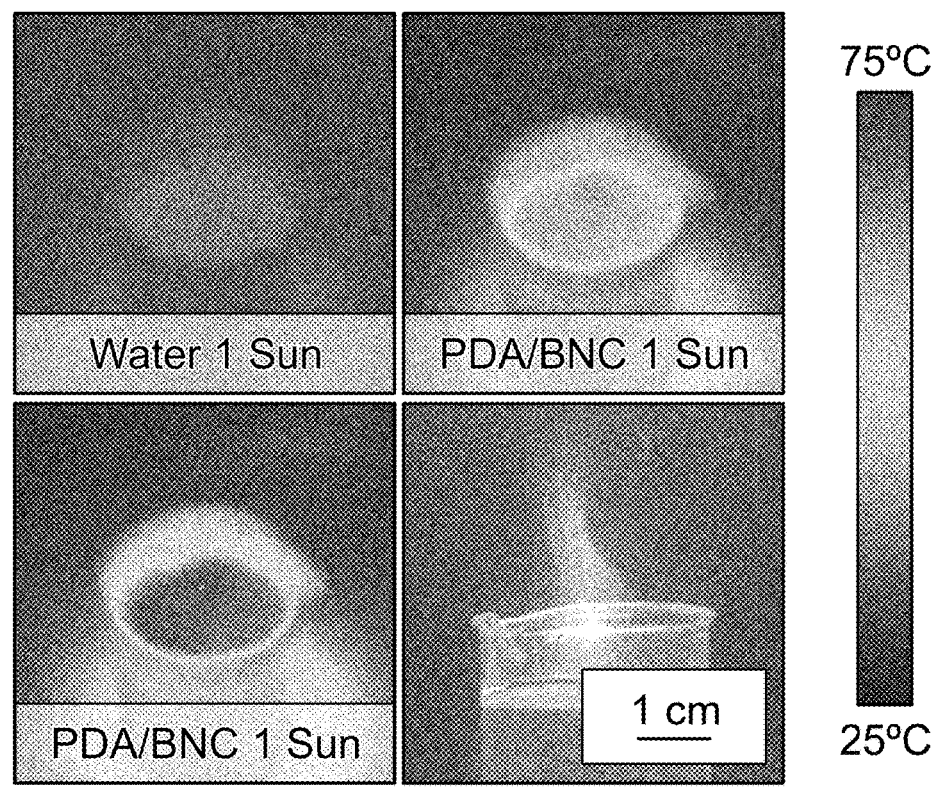
FIG. 20A illustrates IR images of water under 1 kW/m$^2$ solar irradiation, PDA/BNC under 1 kW/m$^2$ and 3 kW/m$^2$ solar irradiation and optical image, showing visible steam generation under 3 kW/m$^2$.
Figure 20B:
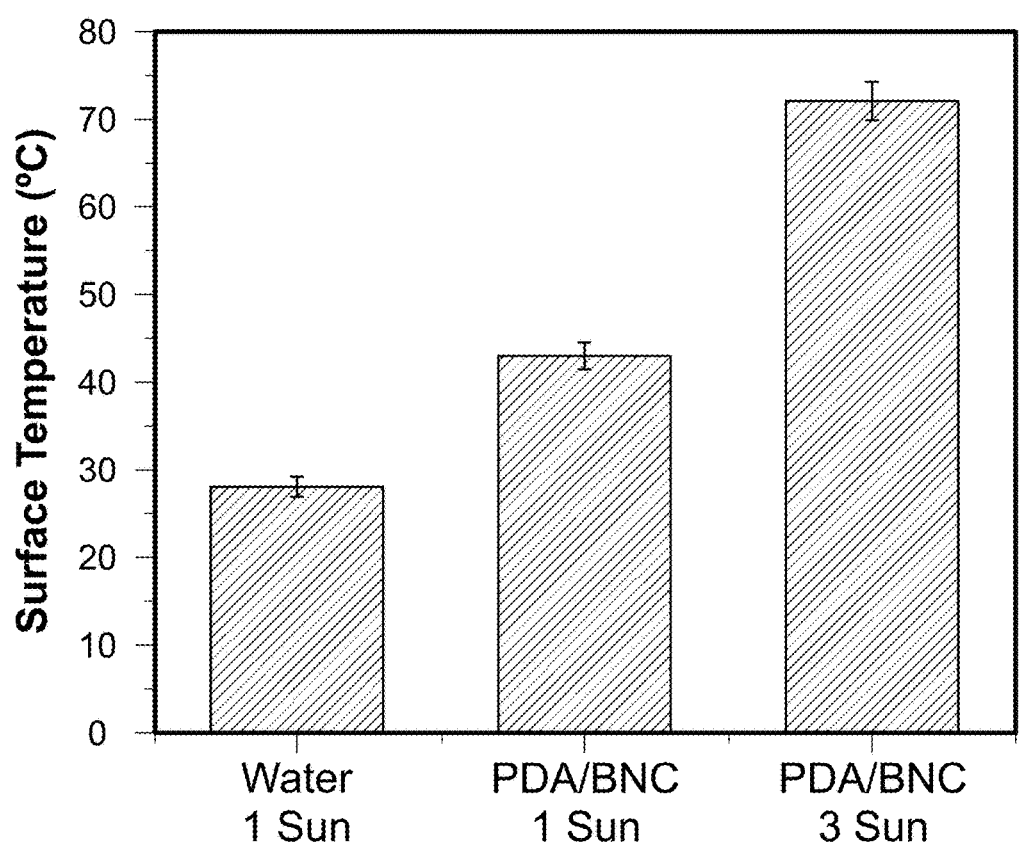
FIG. 20B is a graph of the surface temperatures of water and PDA/BNC foam under 1 and 3 kW/m$^2$ irradiations.

The solar steam generation performance of the PDA/BNC under 1 kW/m$^2$ (approximately one sun) and kW/m$^2$ (approximately three sun) was evaluated. IR imaging was employed to monitor the temperature rise in the PDA/BNC floated at air/water interface upon irradiation with a simulated solar beam (power density of 1 kW/m$^2$ or 3 kW/m$^2$). Upon irradiation, the temperature of the PDA/BNC rapidly increased from room temperature (25° C.) to $\sim 4°$ C. (3 kW/m$^2$) and to $\sim 72°$ C. (kW/m$^2$) (FIGS. 20A,20 B). The temperature rise of water in the absence of PDA/BNC layer was only 2-4° C. The large rise in temperature of PDA/BNC film under 3 kW/m$^2$ illumination resulted in the appearance of steam above the 100-mL beaker, evidencing the rapid evaporation of water (FIG. 20A).

Figure 20C:
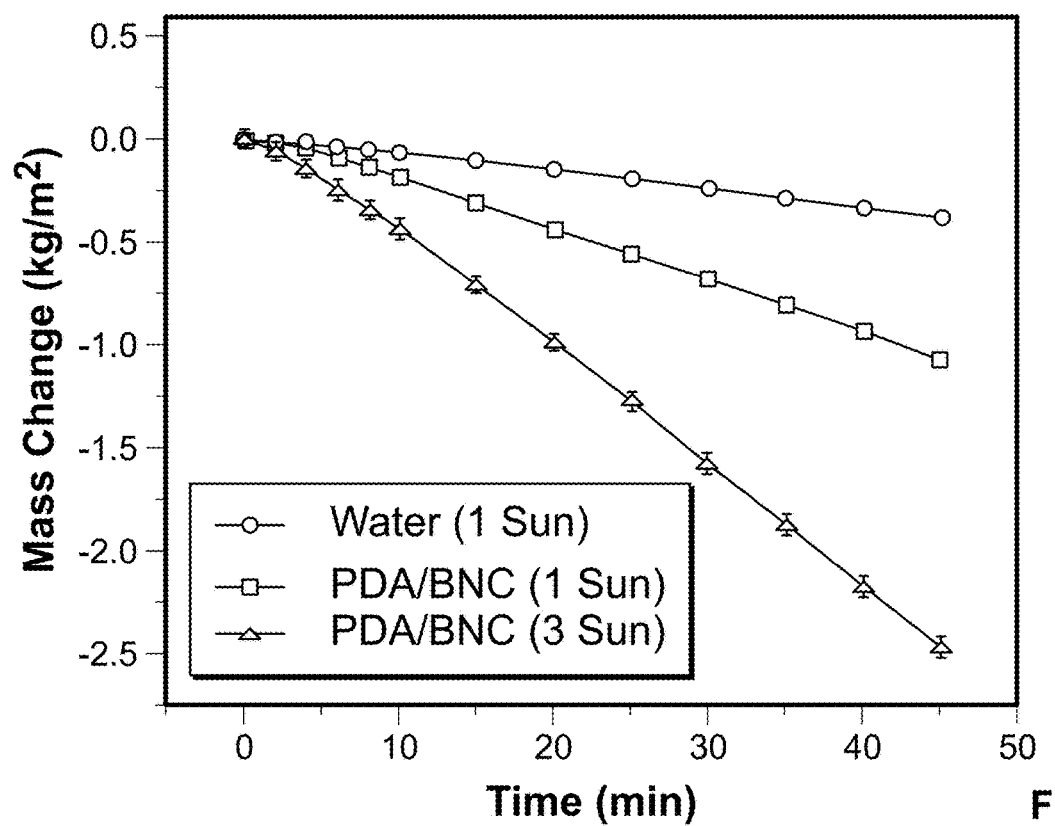
FIG. 20C is a plot showing the cumulative weight losses through water evaporation of water and PDA/BNC foam under different solar irradiations.
Figure 20D:
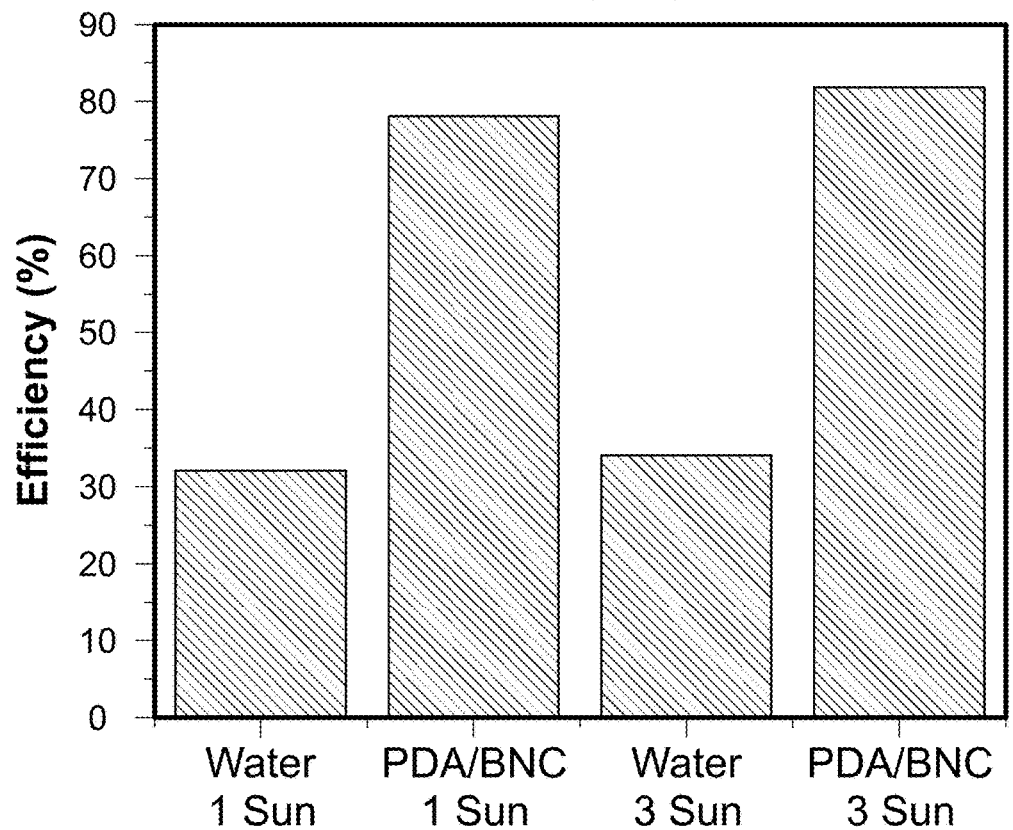
FIG. 20D compares the steam generation efficiencies of water and PDA/BNC foam under different solar irradiations.

The efficiency of the PDA/BNC interfacial evaporator was quantified by measuring the weight loss (due to water evaporation) as a function of irradiation time (all tests were performed for 45 min). The cumulative weight loss increased linearly with irradiation time (FIG. 20C). Under one sun irradiation, the evaporation rate was 1.13 kg/m$^2$·h. In the absence of the PDA/BNC steam generator, the evaporation rate of water under identical irradiation was 0.46 kg/m$^2$·h. The steady state evaporation rate under 3 kW/m$^2$ with PDA/BNC is 3 kg/m$^2$·h. In the tested embodiment, the evaporation efficiency of PDA/BNC was calculated to be 78% under one sun. The evaporation efficiency of unaided water is only 32% due to the poor photothermal conversion and the large energy loss associated with bulk water heating. With increasing solar power density, the evaporation efficiency increased to 82% under 3 kW/m$^2$ (FIG. 20D).

Figure 21A:
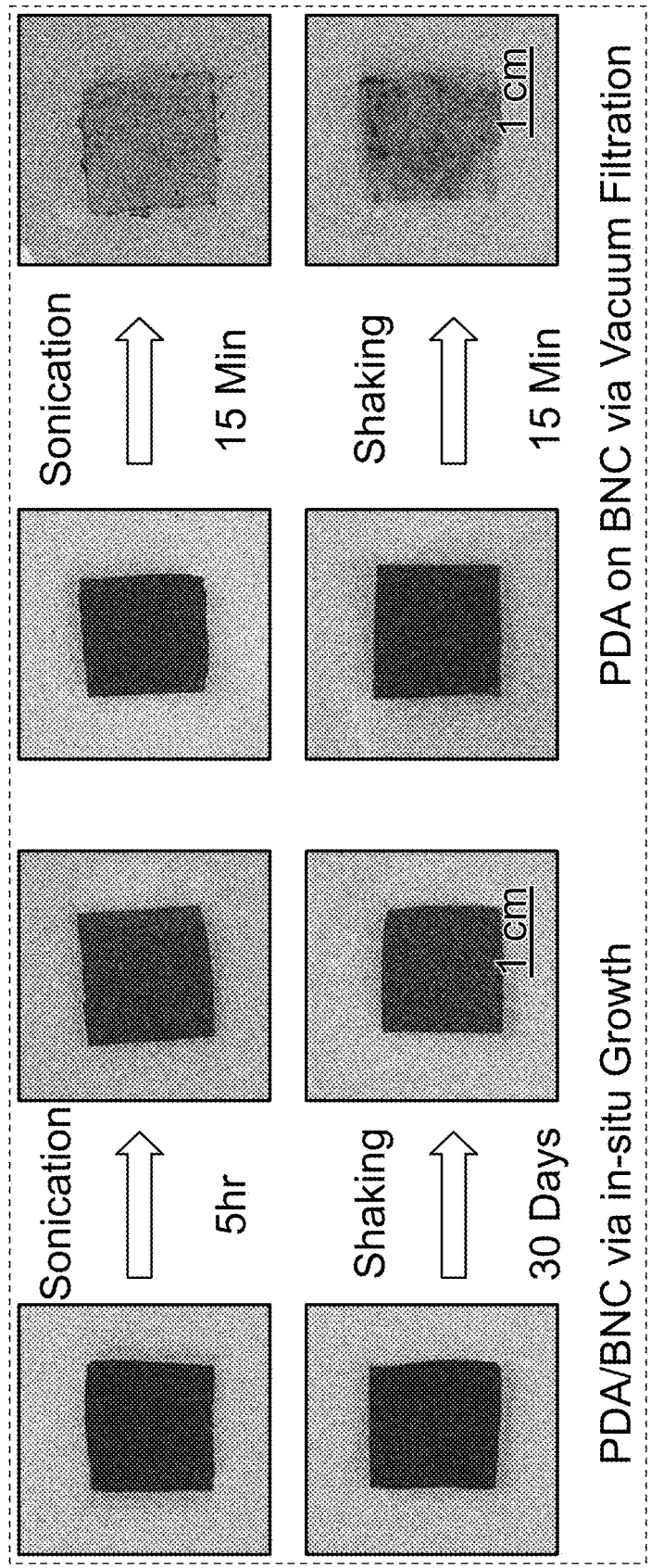
FIG. 21A is optical images of PDA/BNC foam achieved via in situ growth and vacuum filtration that have been subjected to sonication and shaking for extended duration.
Figure 22A:
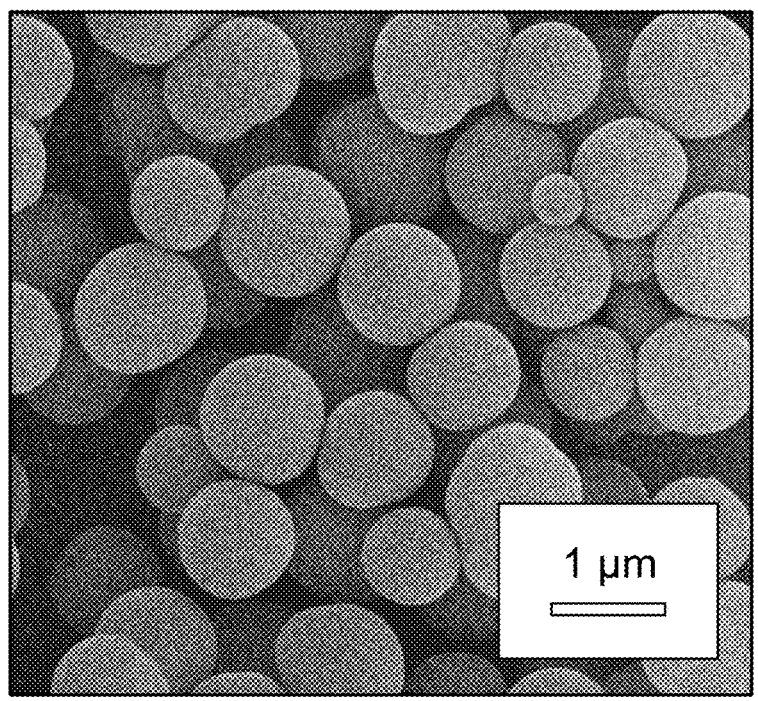
FIG. 22A is an SEM image of PDA particles.
Figure 22B:
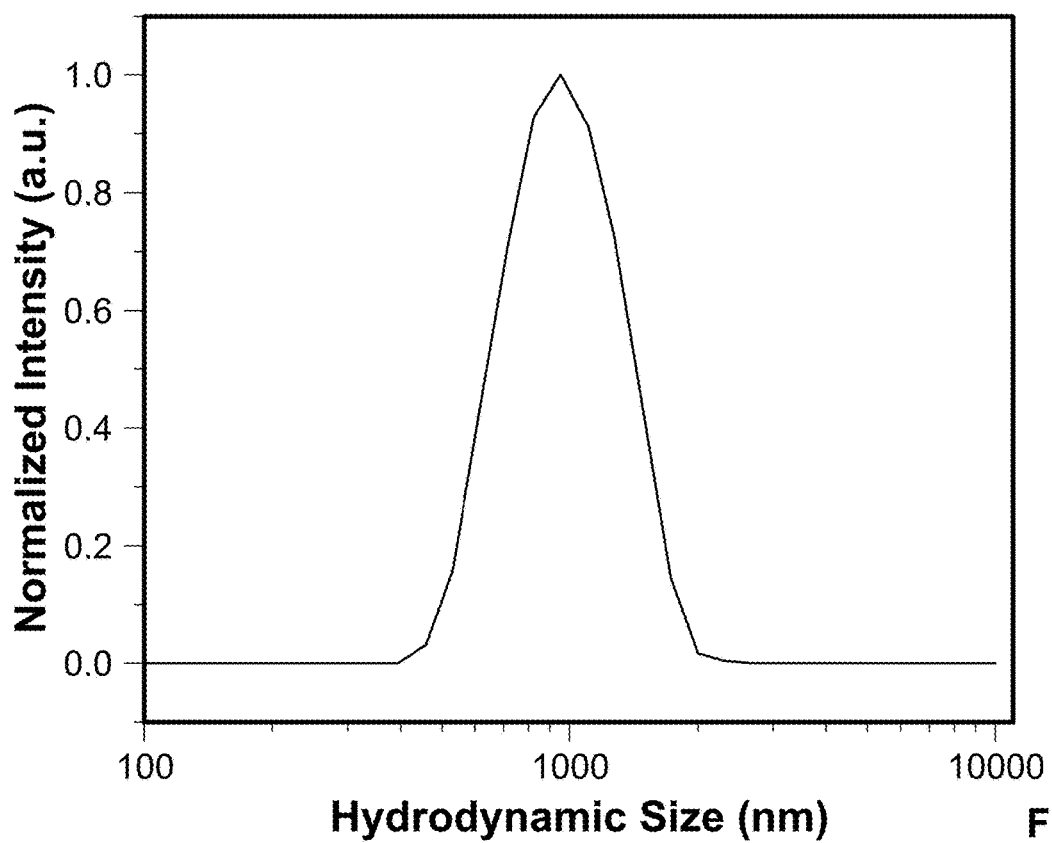
FIG. 22B is a graph of the hydrodynamic size of PDA particles measured by DLS.

To test the robustness of the PDA/BNC foam, it was subjected to rigorous mechanical agitation and boiling for 2 hours during a cleaning procedure to remove the bacteria and culture medium residue. Despite the strong mechanical agitation, the tested embodiment did not exhibit any signs of disintegration or loss of PDA particles. To further test its stability, the PDA/BNC was subjected to ultrasonic agitation (483 W) for 5 hours with vigorous shaking for 30 days. The membrane did not exhibit any signs of disintegration or loss of PDA particles (FIG. 21A, left part). The robustness of the PDA/BNC solar steam generator allows for reuse multiple times without any noticeable degradation of the structure or steam generation ability. Over 20 cycles of reuse, the steady-state evaporation rate and cumulative weight loss over 15 min irradiations (even under a higher power density, 7 kW/m$^2$) was found to exhibit less than 6% variation (FIG. 21B). The structure of the PDA/BNC evaporator remained unaltered after cycling tests (involving around 5 h high temperature solar exposure), which is evident from SEM images of the PDA/BNC surface before and after cycling (FIG. 21C). TGA results also suggested the excellent thermal stability of BNC (up to 280° C.) and PDA (with 58% left up to 800° C.).

The thermal conductivity of interfacial solar evaporator plays a key role in confining the heat to the evaporative surface so the thermal conductivity of the PDA/BNC under both dry and wet conditions was tested. PDA/BNC samples were sandwiched between two glass slides maintained at different temperatures at both ends. The gradient in the temperature along the thickness of samples was observed using an IR camera (insets of FIG. 19C, 19D). The thermal conductivity of dry PDA/BNC (0.037 W/m·K) is just slightly higher than air (FIG. 19C). The low thermal conductivity of dry PDA/BNC owes to the large porosity (i.e., filled with air pockets with a thermal conductivity of 0.024 W/m·K at room temperature) of the structure. Wet PDA/BNC exhibited a thermal conductivity (0.442 W/m·K) lower than water (0.600 W/m·K at room temperature) (FIG. 19D).

Photothermally Active Reduced Graphene Oxide/Bacterial Nanocellulose Composites as Biofouling-Resistant Ultrafiltration Membranes The present disclosure is further directed to RGO/BNC membranes as ultrafiltration membranes.

Biofouling poses one of the most serious challenges to membrane technologies by severely decreasing water flux and driving up operational costs. The present disclosure is directed to a novel anti-biofouling ultrafiltration membrane based on reduced graphene oxide (RGO) and bacterial nanocellulose (BNC), which incorporates GO flakes into BNC in situ during its growth. In contrast to previously reported GO-based membranes for water treatment, the RGO/BNC membrane exhibited excellent aqueous stability under environmentally relevant pH conditions, vigorous mechanical agitation/sonication, and even high pressure.

Importantly, due to its excellent photothermal property, under light illumination, the membranes exhibited effective bactericidal activity, obviating the need for any treatment of the feedwater or external energy. The novel design and in situ incorporation of the membranes developed in this disclosure provide for new, highly efficient, and environmentally-friendly anti-biofouling membranes for water purification.

Water scarcity is recognized as one of the most critical global challenges in the 21st century. In response to this dire need, various membrane technologies are being actively investigated for water purification and reclamation. However, fouling and consequent degradation of membranes during performance still remain a ubiquitous problem. The three major fouling mechanisms: mineral scaling, organic fouling, and biofouling, all lead to a decline in water flux. Among them, biofouling, which accounts for more than 45% of all membrane fouling, is the Achilles heel of the membrane technologies, due to the difficulty of completely removing microorganisms.

To inhibit the formation of biofilms, various biofouling controlling strategies, such as adjusting pH, adding disinfectants and biocides, and introducing quorum quenching molecules, have been suggested. However, most of these strategies cause considerable operational costs and/or potential hazardous contaminants. Researchers have also investigated the incorporation of nanomaterials (e.g., silver nanoparticles, $TiO_2$ nanoparticles, and graphene oxide nanosheets), polymers (e.g., polyethylene glycol, poly(vinyl alcohol), polyvinylpyrrolidone, and zwitterionic polymers), and other materials (e.g., small organic molecules and biomacromolecules) to engineer fouling-resistant membrane surfaces that can reduce biofilm growth and inactivate bacteria. However, most of these methods involve additional thermal or chemical treatment steps. Furthermore, most techniques are effective for only a short period of time, because biofilm can gradually adapt to the imposed harsh environments. Even if 99.9% of biofilm is removed, the residual cells are sufficient to grow back and form a new biofilm. Highly efficient and cost-effective methods that overcome biofouling on water purification membranes over a long period of time would immediately help meet the grand challenge of providing access to clean water.

The photothermal effect of materials offers a unique solution to biofouling, obviating the need for harsh chemical treatments to achieve bacterial lysis. Photothermally active materials effectively absorb light and then convert it into heat. Previously, gold nanostars grown on graphene oxide (GO) flakes coating a commercial membrane were utilized as nanoheaters. In this approach, with laser irradiation, the photothermal properties of the gold nanostars and GO were utilized to quickly kill adjacent *Escherichia coli* bacteria, inhibiting the formation of biofilm on reverse osmosis membranes. While this study provided a promising example of utilizing the photothermal effect to minimize biofouling on membranes, it would be even more beneficial if the membrane itself were comprised of photothermal materials.

GO has been recognized as an efficient photothermal material because the closely spaced energy levels from loosely bonded π electrons absorb the broad electromagnetic spectrum. The absorbed light energy excites electrons which then relax to the ground states through non-radiative decay, releasing the energy by heat. In addition to the photothermal property, GO has frequently been employed as a membrane component owing to its excellent mechanical strength and facile synthesis. In contrast to graphene flakes, which have a strong tendency to stack and aggregate in aqueous solutions, GO flakes are easily dispersed, making the membrane preparation process easier in aqueous media. This dispersibility comes from rich oxygen-containing functional groups (carboxyl, epoxy, hydroxyl, and carbonyl groups). However, the stability of current GO-based membranes is compromised by vigorous agitation, and pH and ionic strength variations that are within the typical range of feed waters. Thus, there remains a need to develop new scalable approaches to fabricate stable GO-based membranes.

The present disclosure is directed to an ultrafiltration membrane using solar illumination to prevent biofouling.

The ultrafiltration membrane possesses water purification abilities and is both environmentally friendly and highly scalable.

In particular, the present disclosure is directed to a novel way to make scalable and inexpensive bacterial nanocellulose/graphene oxide water ultrafiltration membranes which have excellent antibiofouling ability enabled by sunlight. In some embodiments, the membranes have graphene oxide flakes embedded within a bacterial nanocellulose network and sunlight irradiating on the membrane is converted to heat, which effectively kills the microorganisms coming in contact with the membrane to prevent the formation of a biofilm.

In some embodiments, bacterial nanocellulose and graphene make the ultrafiltration membranes highly scalable and inexpensive. The processes developed are also scalable and cost-effective. The membranes in accordance with the present disclosure serve as highly stable ultrafiltration membranes. Further, simply using solar illumination on these membranes efficiently prevents biofouling.

Accordingly, in one embodiment of the present disclosure, a composition comprising nanocellulose and a nanomaterial is disclosed. In some embodiments, the nanocellulose is selected from the group consisting of cellulose nanofibers, microfibrillated cellulose, nanocrystalline cellulose, bacterial nanocellulose and combinations thereof. In some embodiments, the nanocellulose is bacterial nanocellulose.

In some embodiments, the bacterial nanocellulose is made by a bacterial culture selected from the group consisting of *Acetobacter xylinum, Acetobacter hansenii, Acetobacter pasteurianus, Gluconacetobacter hansenii* (ATCC 23769 or ATCC 53582), *Gluconacetobacter xylinus* (formerly named *Acetobacter xylinum*), *Escherichia coli, Agrobacterium tumefaciens, Asaia bogorensis, Rhizobium* spp., *Sarcina ventriculli, Gluconacetobacter sacchari* and combinations thereof. In some embodiments, the bacteria for producing nanocellulose is *Gluconacetobacter hansenii, Acetobacter pasteurianus,* or *Gluconacetobacter xylinus*.

In some embodiments, the nanomaterial is selected from the group consisting of graphene oxide, reduced graphene oxide, molybdenum disulfide ($MoS_2$), polydopamine (PDA, melanin), functionalized multiwalled carbon nanotubes (e.g., —OH, —COOH modified) and combinations thereof.

In one embodiment of the present disclosure, a method for purifying water is disclosed. The method comprises passing water through a membrane, wherein the membrane comprises nanocellulose and a nanomaterial. In some embodiments, the method further comprises exposing the membrane to solar radiation. In some embodiments, a temperature on a surface of the membrane increases to at least about 20° C., at least about 30° C., at least about 40° C., or at least about 50° C. In some embodiments, the temperature increases on the surface of the membrane to at least about 20° C., at least about 30° C., at least about 40° C., or at least about 50° C. in about 60 seconds or less, about 40 seconds or less, about 30 seconds or less, about 20 seconds or less, or about 10 seconds or less.

In some embodiments of the present disclosure, at least about 50%/a, at least about 60%, at least about 70%, at least about 80%, at least about 90% or at least about 99% of any bacteria present on and/or in the membrane is killed.

In some embodiments of the present disclosure, the membrane has a thickness of from about 1 μm to about 10 μm, from about 2 μm to about 7 μm, from about 3 μm to about 5 μm, or about 4 μm.

In some embodiments, the membrane has a pore size of from about 5 nm to about 100 nm, from about 20 nm to about 80 nm, from about 40 nm to about 60 nm, or about 50 nm. In some embodiments, the membrane has a pore size of less than about 50 nm, less than about 40 nm, less than about 30 nm, less than about 20 nm, less than about 10 nm, or less than about 5 nm.

Disclosed herein is a novel and facile approach for the fabrication of an anti-biofouling ultrafiltration membrane, involving in situ incorporation of GO flakes into bacterial nanocellulose (BNC) during its growth. The reduced graphene oxide/bacterial nanocellulose (RGO/BNC) membrane exhibits excellent aqueous stability under vigorous mechanical agitation and harsh chemical conditions and stable water flux. Importantly, the membrane exhibits bactericidal capability enabled by abundant, renewable energy source—solar illumination—due to its excellent photothermal effect properties, obviating the need for any treatment of the feed water and external energy. The novel designs and methods represent an important step forward to the realization of highly efficient, environmental-friendly and anti-biofouling membranes for water purification BNC is a highly pure form of cellulose produced from dextrose through a series of biochemical steps followed by the self-assembly of secreted cellulose fibrils from bacteria in the culture medium. Similar to other cellulose nanomaterials such as cellulose nanofibers, cellulose nanocrystals (CNC), BNC is highly attractive for membrane technologies for water treatment due to their excellent mechanical properties, tunable porosity, chemical functionalizability, ease of synthesis, high scalability, and more importantly, low environmental impact. For all the above mentioned reasons, BNC is also a highly promising material for the fabrication of functional composites through in situ growth or adsorption of pre-synthesized nanostructures on the nanoscale cellulose fibers.

In some embodiments, the fabrication of the RGO/BNC membrane is achieved by culturing *Gluconacetobacter hansenii* bacteria in the presence of GO flakes under aerobic and static growth conditions. GO flakes were synthesized using a previously reported method. It is known that the thickness of a monolayer of GO is about 0.72 nm and the higher thickness of GO compared to a monolayer of graphene (0.34 nm) is ascribed to the presence of epoxy and hydroxyl groups on the basal plane. Atomic force microscope (AFM) images revealed the average thickness of GO flakes deposited on a silicon substrate to be about 1±0.2 nm, which corresponds to a bilayer of GO. To form a GO/BNC layer, in some embodiments, GO flakes were washed and then dispersed in the broth solution with bacteria at a predetermined concentration to achieve a desired BNC growth rate. The mixture was homogenized and left under the static condition to obtain BNC hydrogel of a desired thickness with uniformly embedded GO flakes. To remove bacteria and residual growth medium, the GO/BNC hydrogel was washed using NaOH solution (0.1 M) at high temperature (boiling condition) which can partially reduce GO flakes. The cleaned RGO/BNC hydrogel was air-dried to obtain the RGO/BNC membrane with thickness of about 4 μm.

In some embodiments of the present disclosure, the bacteria that produce cellulose or nanocellulose include, but are not limited to *Gluconacetobacter hansenii* (ATCC 23769 or ATCC 53582), *Gluconacetobacter xylinus* (formerly named *Acetobacter xylinum*), *Escherichia coli, Agrobacterium tumefaciens, Acetobacter pasteurianus, Asaia bogorensis, Rhizobium* spp., *Sarcina ventriculli,* and *Gluconacetobacter sacchari*. In some embodiments, the bacteria for producing nanocellulose is *Gluconacetobacter hansenii, Acetobacter pasteurianus*, or *Gluconacetobacter xylinus*.

In some embodiments, the bacteria is *Gluconacetobacter hansenii*. The fabrication of a bilayer structure involves growing *Gluconacetobacter hansenii* bacteria in the presence of GO, RGO or a combination thereof.

To understand the chemical reduction of GO during the cleaning process, the effect of the high-temperature base wash (conditions employed in BNC cleaning process) on the GO flakes was investigated. The BNC/GO structure turned from clear brown suspension to a black aggregate, indicating the partial reduction and restacking of the RGO. To confirm the chemical modification (e.g., reduction of GO) of GO upon base wash, X-ray photoelectron spectroscopy (XPS) was utilized. The is spectra of carbon was deconvoluted into three peaks corresponding to $sp^2$ domains (C=C with a binding energy of 284 eV) and oxidized $sp^3$ domains (C—O with a binding energy of 286 eV and C=O with a binding energy of 288 eV). For as synthesized GO, the C/O ratio (1.7) obtained from the ratio of the area under the peaks suggested that about 58% of the surface of GO was oxidized. After extensive base washing, the C/O ratio increased to 4.6 indicating that only about 21% of the surface of GO was oxidized.

A pristine BNC membrane (produced in the absence of GO flakes in the broth) was white and translucent and shows excellent flexibility and mechanical strength. The cellulose fibers which are of about 20-100 nm in diameter were first formed by the bacteria at the air/medium interface and fibers entangle to form a "layer" at the surface. As the oxygen diffused deeper into the medium, the first layer guides the formation of the subsequent BNC layers, which stack together to form a 3D BNC network. Considering this "layer-by-layer" formation, the cellulose nanofibrils were preferentially oriented parallel to the surface (i.e. normal to the thickness) of the membrane, which resulted in denser physical entanglements of the cellulose nanofibrils parallel to the surface compared to that along the thickness. As noted above, the addition of GO flakes to the bacterial broth and base wash led to the formation of RGO/BNC membrane. The surface of the RGO/BNC membrane was smoother and less fibrillar compared to the pristine BNC membrane due to the incorporation of GO flakes. The "layered" formation of BNC starting from the liquid/air interface facilitated the layered arrangement of RGO flakes between each BNC layers as evidenced by the cross-sectional SEM images of the RGO/BNC membrane.

The RGO/BNC membrane was subjected to rigorous mechanical agitation and strong basic solution during cleaning procedure to remove the bacteria and culture medium residue. Despite the strong mechanical agitation, the membrane did not exhibit any signs of disintegration or loss of GO flakes. To further test the stability of the membrane, the membrane was subjected to ultrasonic agitation (42 kHz) for 5 hours in pH 4, pH 7, and pH 9 solutions. Even after this vigorous mechanical and chemical treatment, the membrane did not exhibit any signs of disintegration of RGO flakes. This was also evident from the SEM images of the membrane surface, which show no discernable change in the morphology after sonication. Thermogravimetric analysis (TGA) was used to evaluate the thermal stability of RGO/BNC membrane. The RGO/BNC membrane showed first mass loss (~2%) at ~100° C. was due to the loss of absorbed water. The second mass loss (~3%) at ~200° C. was due to the decomposition of functional groups of GO. The third mass loss (~46%) onsets at 280° C. was due to the degradation of cellulose. The fourth mass loss (~49%) at 390° C. was due to the continued decomposition of cellulose residual and sublimation or burning of the damaged graphitic regions. Based on mass loss profile of RGO/BNC membrane, RGO and pristine BNC membrane, the mass loading of RGO in RGO/BNC was calculated to be ~45 wt. %. The RGO/BNC membrane after ultrasonic treatment also showed an identical mass loss profile, meaning that the embedded RGO within BNC matrix remained intact. TGA also demonstrated the excellent thermal stability of RGO/BNC membrane up to 200° C.

As mentioned above, GO-based membranes have been investigated in the past few years. Most of these membranes involve vacuum filtration of GO flakes onto a supporting membrane and the long-term aqueous stability is questionable. For comparison, a RGO/BNC composite membrane was prepared by depositing an RGO layer (base-washed) on top of a BNC membrane using vacuum filtration. After 5 h ultrasonic agitation in solutions at pH 4, 7, and 9, the RGO layer disintegrated completely. The aqueous solution exhibited broad absorbance corresponding to the detached RGO flakes in the UV-vis absorption spectrum. After rinsing, almost no RGO flakes remained on the BNC surface. The membrane after sonication only showed an initial mass loss (~5%) at 100° C. which was attributed to absorbed water, a mass loss (~63%) at ~280° C. due to the degradation of cellulose and a mass loss (~32%) at ~340° C. due to the decomposition of cellulose residual, indicating the absence of RGO flakes. Conventional GO-based membranes rely on hydrogen bonding or metal ions to provide mechanical stability to the membranes. However, mechanical agitation during water filtration or cleaning procedure and pH variations in the feed water compromises the mechanical stability of these membranes. On the other hand, an RGO/BNC membrane produced as described herein offers a unique advantage. During the BNC growth, plate-like GO sheets are incorporated and physically locked into layered BNC matrix, which leads to the excellent mechanical, chemical and thermal stability.

To determine pore sizes and particle rejection capability of these novel membranes, the particle rejection performance was determined using size-controlled gold nanoparticles and flux of a RGO/BNC membrane. Gold nanoparticles (AuNPs) with diameters of about 10.3±0.7 nm, 20.4±1.1 nm, 30±0.9 nm, and 49.7±1.8 nm were synthesized using a seed-mediated method. The synthesized AuNPs showed very narrow size distribution (RSD <6.7%), which was critical for a particle rejection study. By measuring the UV-VIS extinction spectrum of filtrate/permeate solutions of the AuNPs before/after filtration through the RGO/BNC membrane, the particle rejection rate was calculated (see Examples). The particle rejection fraction showed a linear increase with increase in the diameter of the particle and reached ~100% rejection for particle with a diameter of about 50 nm. This indicates that the pore size of the RGO/BNC membrane has finite distribution below about 50 nm, which is similar to a commercial ultrafiltration (UF) membrane.

To check their flux as a membrane material, flux tests were performed using a benchtop cross-flow system on both commercial ultrafiltration membranes (YMGESP3001, GE) and RGO/BNC membranes. RGO/BNC membranes showed comparable performance to the commercial ultrafiltration under same operation conditions (250 psi), as the fluxes of RGO/BNC membrane is around 60 $L/m^2 \cdot h$ and for the commercial ultrafiltration membrane, 48 $L/m^2 \cdot h$ and during 6 hours-long operation, the RGO/BNC showed very stable fluxes. The above results indicated that RGO/BNC membrane can be used as an ultrafiltration membrane with pore size less than about 50 nm.

The photothermal and bactericidal ability of the new RGO/BNC membranes was determined under simulated solar irradiation. IR imaging was employed to monitor the temperature rise of the RGO/BNC membrane under water upon irradiation with a simulated solar illumination (power density of 2.9 KW/m$^2$). Upon illumination, the temperature of the RGO/BNC membrane rapidly increased from room temperature (26° C.) to ~60° C. The temperature rapidly increased within 20 secs after the irradiation and remained constant over the entire duration (120 sec). Conversely, the pristine BNC membranes showed only a small temperature increase (3° C.). Upon irradiation, RGO flakes in the membrane generated a large amount of heat that quickly dissipated to the surrounding water and BNC. The temperature profile obtained from an IR camera did not represent the actual local temperature, which was much higher, experienced by the biological species adsorbed on the surface of the RGO/BNC membrane. The large rise in temperature owed to the high optical absorption of RGO.

To test the bactericidal ability, the RGO/BNC membrane was covered with a layer of *E. coli* and subjected to simulated solar irradiation followed by a live/dead cell viability assay. Before irradiation, both RGO/BNC membrane and BNC membrane showed green florescence corresponding to live bacteria and absence of red stains (indicating the absence of dead bacteria). After irradiation for 180 secs, bacteria on RGO/BNC membrane were found to exhibit predominantly red fluorescence (dead bacteria) and complete absence of green fluorescence (live bacteria). On the other hand, a BNC membrane even after irradiation exhibited green fluorescence corresponding to live bacteria. The cell walls of *E. coli* deteriorated at temperatures near 70° C. causing lysis. Before irradiation, live *E. coli* on an RGO/BNC membrane showed a typical rod-like shape, while after irradiation they had significantly shrunk and wrinkled indicating cell leakage due to high temperatures disrupting the integrity of the cell walls and membranes. This indicates that upon solar irradiation, the surface of RGO/BNC membrane rapidly heated up to above 70° C. and kills bacteria within a very short of time (180 sec). The excellent bactericidal activity of RGO/BNC membrane purely by harvesting sunlight makes the novel membrane demonstrated highly attractive for energy-saving and environmental-friendly water purification applications.

Bacterial nanocellulose (BNC) is a highly pure cellulose produced by bacteria with a low-molecular weight sugar as a food source. Through a series of biochemical steps, the bacteria form exterior cellulose nanofibers in aqueous cultures, and these fibers become entangled to form a three-dimensional (3D) network hydrogel. Similar to other cellulose nanofibers and cellulose nanocrystals (CNC), BNC is highly attractive for membrane technologies in view of its excellent mechanical properties, tunable porosity, chemical functionalizability, easy synthesis, high scalability, and most importantly, low environmental impact. Therefore, BNC is used for fabricating functional composites through in situ growth or by adsorption of pre-synthesized nanomaterials on the nanoscale cellulose fibers.

The present disclosure is further directed to a novel and facile approach for fabricating an anti-biofouling ultrafiltration membrane, involving in situ incorporation of GO flakes into BNC during its growth. The reduced graphene oxide (RGO) incorporated BNC membrane not only exhibited outstanding mechanical and chemical stability under environmentally relevant pH conditions and vigorous mechanical agitation/sonication, but also showed stable water flux under high pressure. Particularly, owing to its photothermal properties, the membrane exhibited light-enabled bactericidal activity. The novel design and preparation method introduced here created highly efficient, environmentally friendly, and biofouling-resistant membranes for water purification.

The disclosure presented herein is directed to an innovative approach that uses the photothermal effect of RGO by embedding it in BNC structures. This new type of membrane enhances the stability and durability of a membrane and inhibits or delays microorganism growth on its surface. While the most contemporary approaches to resisting biofouling rely on temporary chemical treatments, combining the photothermal effect with a noble membrane design shows that antibiofouling is achieved with a sustainable and abundant resource, sunlight.

In order to fully utilize the photothermal property of RGO/BNC membranes, in some embodiments, modifying a spiral-wound module system (as shown in FIG. 30A) is used. The inner and outer surfaces of the membrane modules or feed channel spacers are equipped with low-energy light-emitting diodes (LEDs) for illumination, and are be powered by renewable energy sources, such as low-cost photovoltaic devices or triboelectric nanogenerators (TENGs). In TENGs, mechanical energy generated through fluid flow in the UF process is harnessed to produce light and to heat the membrane surface, reducing the overall operational expense. In addition to a spiral-wound module system, this system is also applied to plate sheet membrane modules by adding LED-equipped plates between the membrane modules.

The membranes used herein demonstrated the anti-biofouling properties of RGO/BNC membrane, which originated from localized surface heating by photothermal effect of RGO particles. In particular, the biofilm growth on membrane was inhibited by inactivating the bacteria.

The novel fabrication method of incorporating RGO during "layer-by-layer" growth of BNC yielded a well-stacked structure, with a pore size in the UF membrane range. In addition, BNC production is considered ecofriendly because it needs only a low-molecular weight sugar and oxygen as food sources. Until now, many researchers prepared GO membranes through vacuum filtration or spin coating without a polymer matrix, but these fabrication methods inevitably raised the mechanical stability concerns. However, the RGO/BNC membrane of the present disclosure exhibited stable water flux under 100 psi loading and maintained chemical stability at solution pH varying from 4 to 9. The water flux was higher than that of commercial UF membranes under identical pressure. The RGO/BNC membranes of the present disclosure not only provide a novel anti-biofouling approach powered by solar energy, but also provide a scalable, ecofriendly, and cost-effective way to fabricate UF membranes for water purification.

EXAMPLES

The following Examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Examples.

Example 1: Preparation of RGO/BNC Aerogel

*Gluconacetobacter hansenii* (ATCC53582) was cultured in test tubes containing 16 mL of #1765 medium at 30° C. under shaking at 250 µm. The #1765 medium was composed of 2% (w/v) glucose, 0.5% (w/v) yeast extract, 0.5% (w/v) peptone, 0.27% (w/v) disodium phosphate, and 0.5% (w/v) citric acid. Graphene oxide was synthesized using methods known in the art. Graphene oxide solution (28 mL of 0.1 wt. %) was centrifuged and redispersed in #1765 medium and then centrifuged again to leave a wet mixture of GO and medium after decanting supernatant. Bacterial culture solution (incubated 3 d) was added to the GO/medium wet mixture to make it to a total 7 mL (with GO concentration of 0.4 wt. %). The solution was subsequently transferred to a Petri dish and incubated at room temperature without disturbance. After 5 d, a thin film of GO/BNC was formed at the liquid/air interface. Subsequently, 7 mL of bacterial growth solution was added on top of the GO/BNC film. After another 5 d, a bilayer of BNC and GO/BNC film was formed. For purification, the film was harvested from the Petri dish and washed in a 500 mL of 0.1 M NaOH aqueous solution under boiling conditions for 2 h. The obtained RGO/BNC:BNC hydrogel was then dialyzed in nanopure water for 2 d. The purified RGO/BNC:BNC hydrogel was then cut into desired dimensions, typically 1 cm×1 cm with a thickness of 2.1 mm, and then freeze-dried for 12 h.

Microstructure Characterization and Properties Measurements

SEM images were obtained using a FEI Nova 2300 field-emission scanning electron microscope at an acceleration voltage of 10 kV. AFM images were obtained using Dimension 3000 (Bruker Inc.) in light tapping mode. A Shimadzu UV-1800 spectrophotometer was employed for collecting the UV-vis extinction spectra in transmission mode. The Raman spectra were obtained using a Renishaw inVia confocal Raman spectrometer mounted on a Leica microscope with a 20π objective and a 514 nm wavelength diode laser as an illumination source. The FTIR spectra were recorded using a Nicolette Nexus 470 spectrometer. XPS analysis was performed using a Physical Electronics 5000 VersaProbe II Scanning ESCA (XPS) Microprobe. The specific surface areas of the GO/BNC bilayer aerogel were measured by the Brunauer-Emmett-Teller method using an Autosorb-1C (AX1C-MP-LP) at 298 K.

Thermogravimetric Analysis (TGA) to Measure RGO Loading in RGO/BNC:BNC

TGA was used to measure the weight fraction of RGO in the RGO/BNC:BNC structure. TGA was performed for both BNC film and the air-dried RGO/BNC:BNC bilayer film. The BNC film showed an initial mass loss (2-3%) at 100° C., which was attributed to absorbed water, a mass loss (~70%) at ~280° C. due to the degradation of the cellulose and a mass loss (~25%) at ~390° C. due to the decomposition of the cellulose residual, which generated $CO_2$ and $H_2O$. In the case of RGO/BNC:BNC, the initial mass loss (~2%) at ~100° C. was due to the loss of absorbed water, the second mass loss (~3%) at ~200° C. was due to the decomposition of functional groups of GO, the third mass loss (~52%) at 280° C. was due to the degradation of cellulose, and the final mass loss (~40%) at 390° C. was due to the decomposition of the cellulose residual and sublimation or burning of the damaged graphitic regions. Based on the TGA results, the mass loading of RGO in RGO/BNC:BNC was calculated to be ~27 wt. %.

Example 2: Stability of RGO/BNC:BNC

As the RGO/BNC:BNC hydrogel was base-washed during cleaning, it proved its stability in strongly basic environments. For the stability in an acidic environment, one RGO/BNC:BNC hydrogel was put in a Petri dish filled with pH 1.5 solution and sonicated for 1 h and the hydrogel was still intact.

Example 3: Reduction of GO to RGO

Figure 3C:
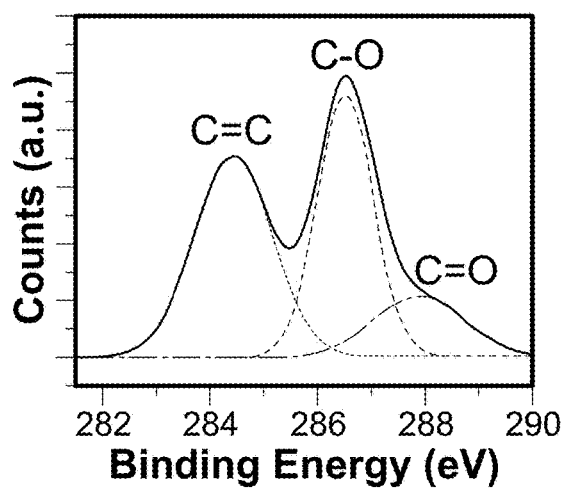
FIG. 3C is an exemplary embodiment of an XPS spectrum of pristine GO in accordance with the present disclosure.
Figure 3D:
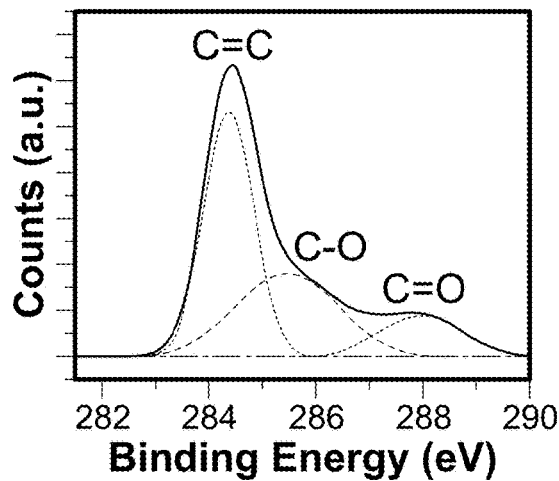
FIG. 3D is an exemplary embodiment of an XPS spectrum of base-washed RGO in accordance with the present disclosure.
Figure 3E:
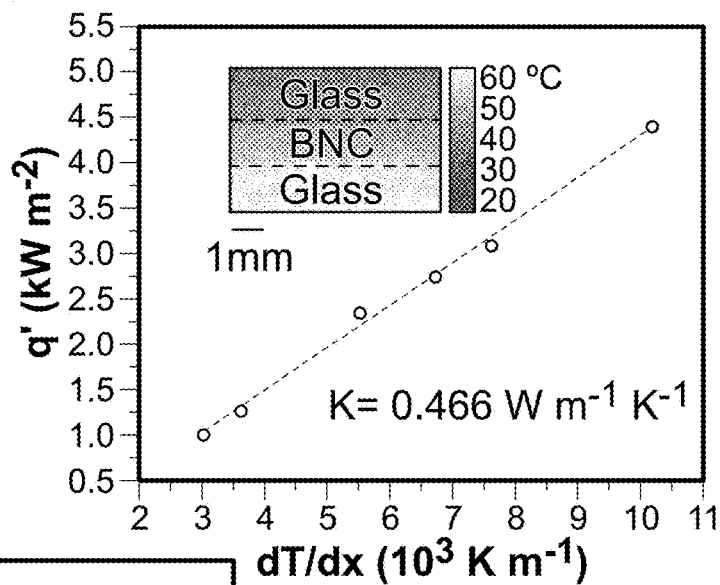
FIG. 3E is an exemplary embodiment of the thermal conductivity of a wet BNC aerogel in accordance with the present disclosure.
Figure 3F:
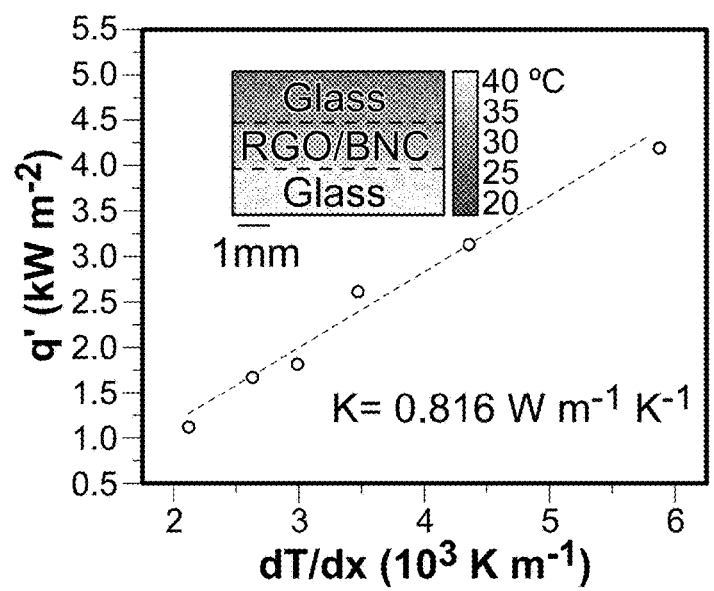
FIG. 3F is an exemplary embodiment of a wet RGO/BNC aerogel in accordance with the present disclosure. The insets in FIGS. 3E and 3F depict IR images showing the temperature gradient along the thickness of the hydrated BNC and RGO/BNC layers.
Figure 4A:
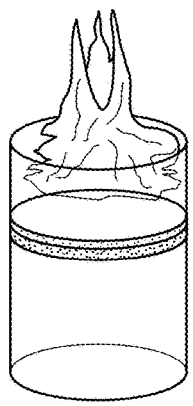
FIG. 4A is an exemplary embodiment of a schematic illustration of steam generation with an RGO/BNC:BNC biofoam in accordance with the present disclosure.
Figure 4B:
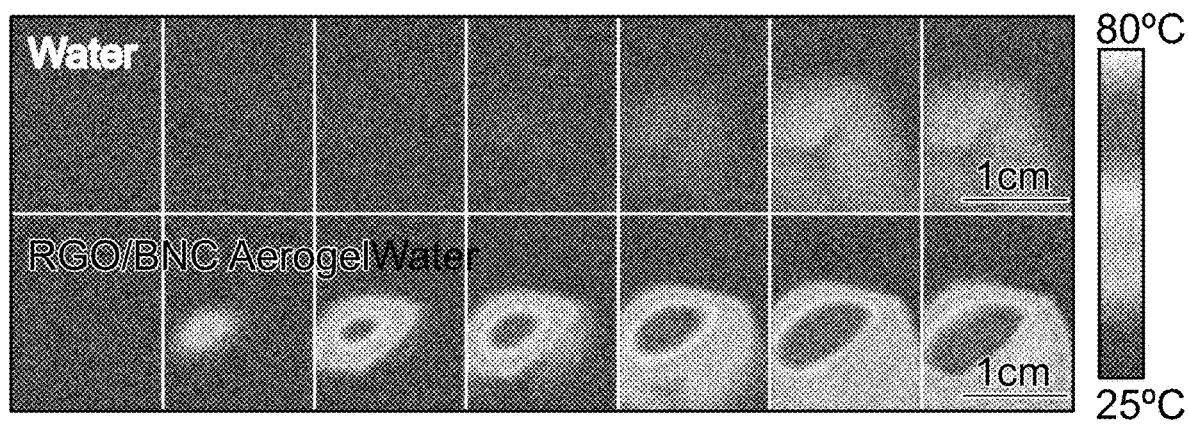
FIG. 4B is an exemplary embodiment of IR images showing the temperature of water and an RGO/BNC:BNC aerogel in accordance with the present disclosure.
Figure 4C:
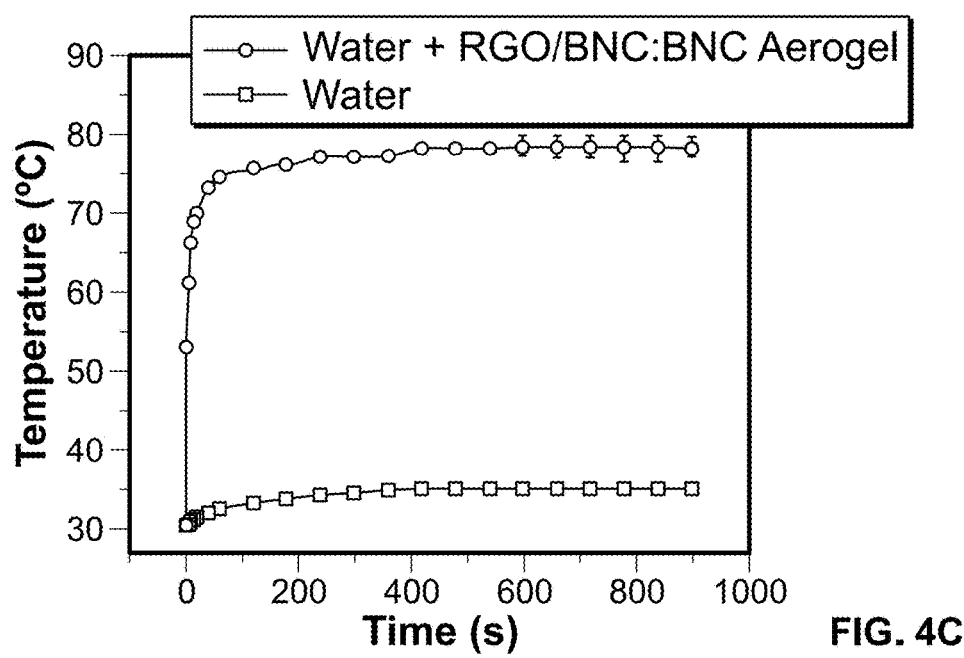
FIG. 4C is an exemplary embodiment of a plot showing the surface temperature of water and an RGO/BNC:BNC aerogel in accordance with the present disclosure.
Figure 4D:
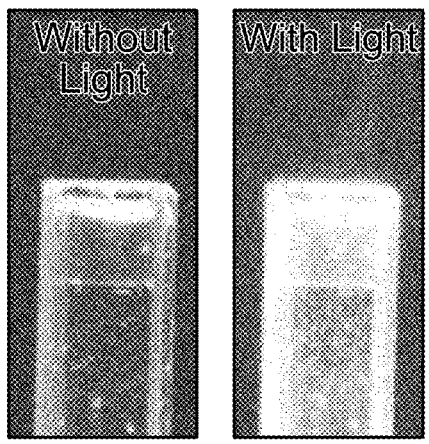
FIG. 4D is an exemplary embodiment of a photograph showing an RGO/BNC:BNC aerogel and steam generation under simulated solar illumination in accordance with the present disclosure.
Figure 4E:
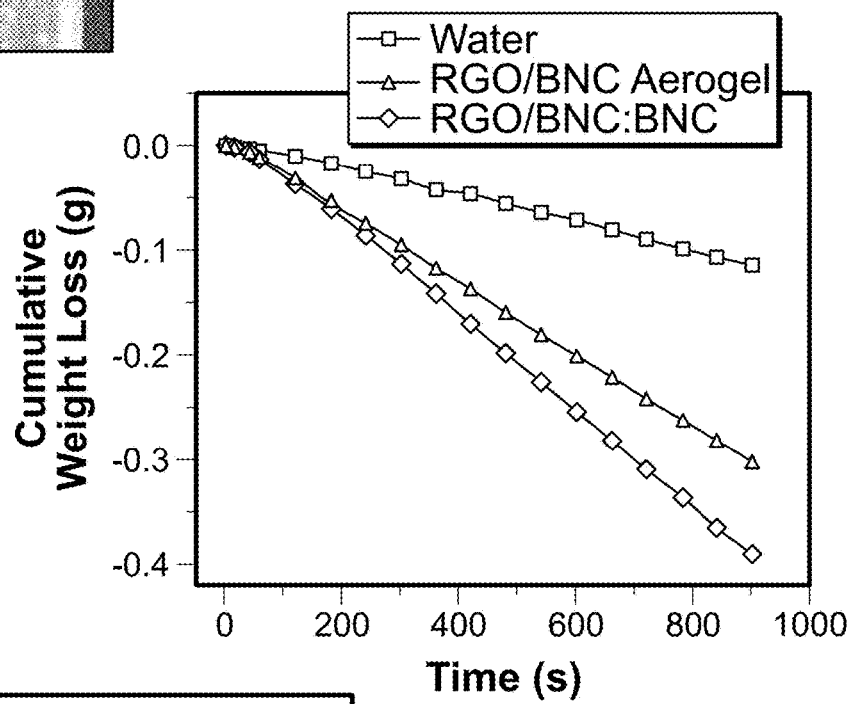
FIG. 4E is an exemplary embodiment of a plot showing the cumulative weight loss through water evaporation under solar illumination as a function of irradiation time in accordance with the present disclosure.
Figure 4F:
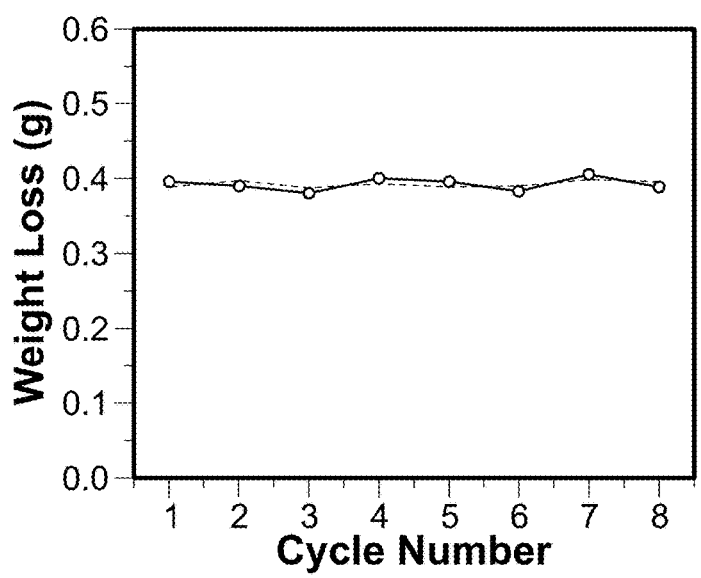
FIG. 4F is an exemplary embodiment of weight loss through water evaporation after irradiation of the RGO/BNC layer in accordance with the present disclosure.
Figure 5:
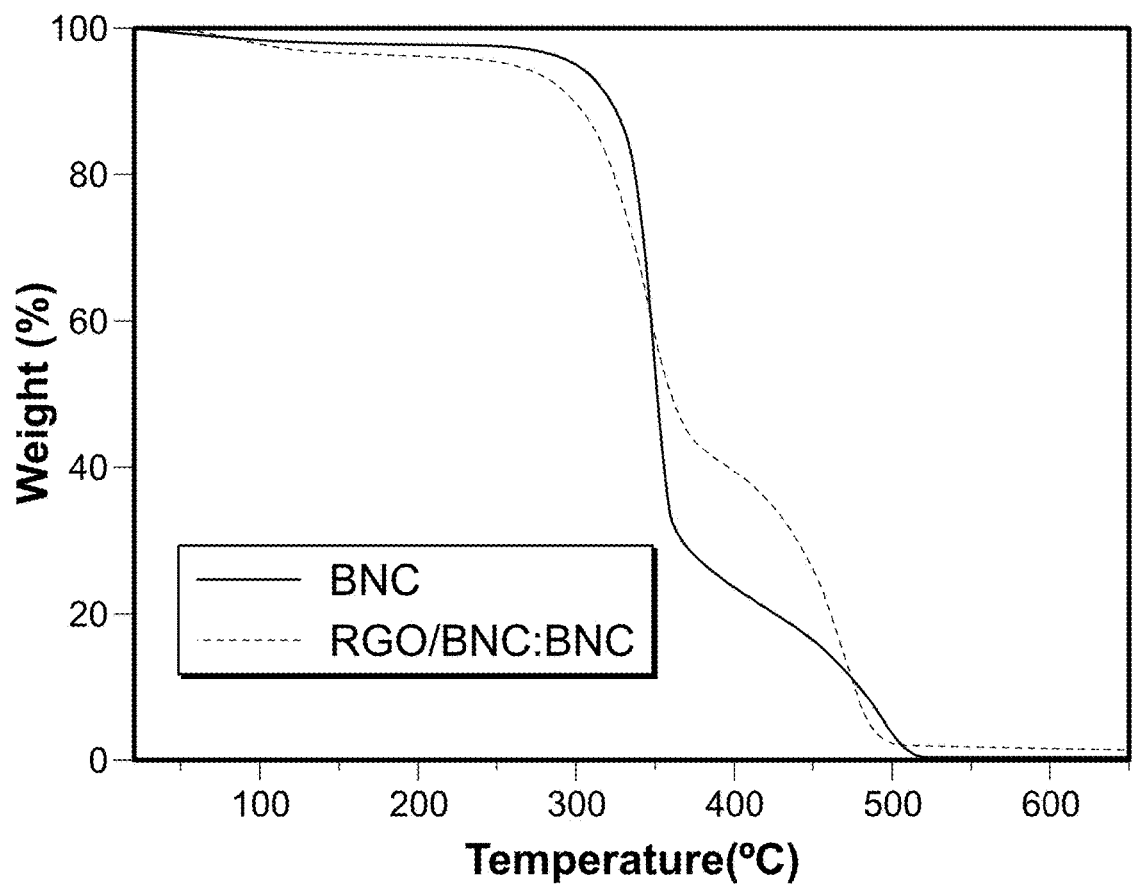
FIG. 5 is an exemplary embodiment of TGA curves for a BNC film and an air-dried RGO/BNC:BNC film in accordance with the present disclosure.
Figure 6A:
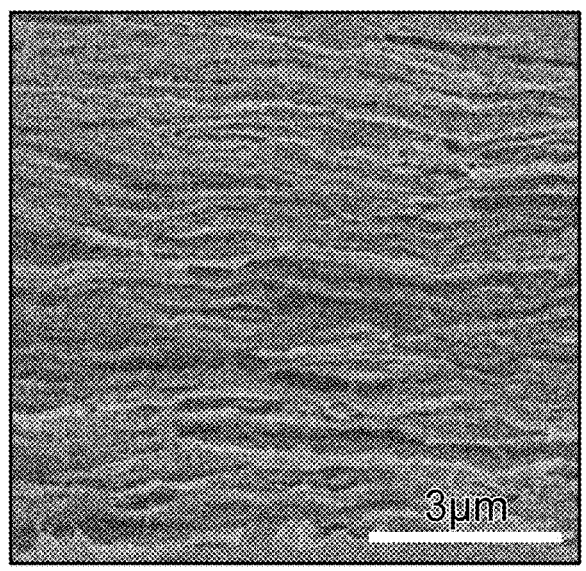
FIG. 6A is an exemplary embodiment of a cross-sectional SEM image of an air-dried RGO/BNC film in accordance with the present disclosure.
Figure 6B:
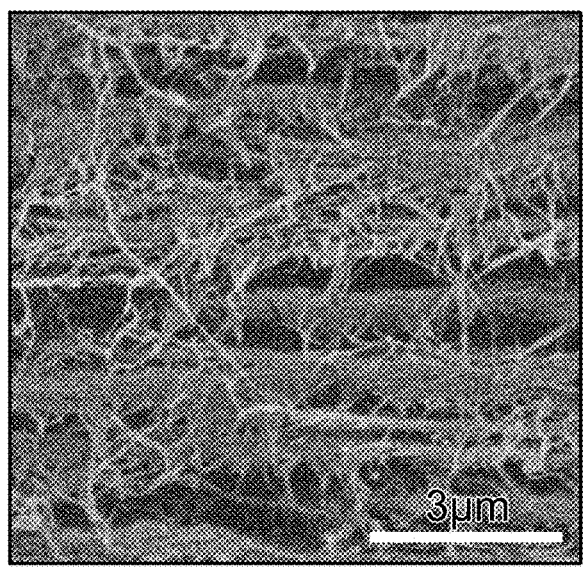
FIG. 6B is an exemplary embodiment of a cross-sectional SEM image of a BNC film in accordance with the present disclosure.
Figure 7:
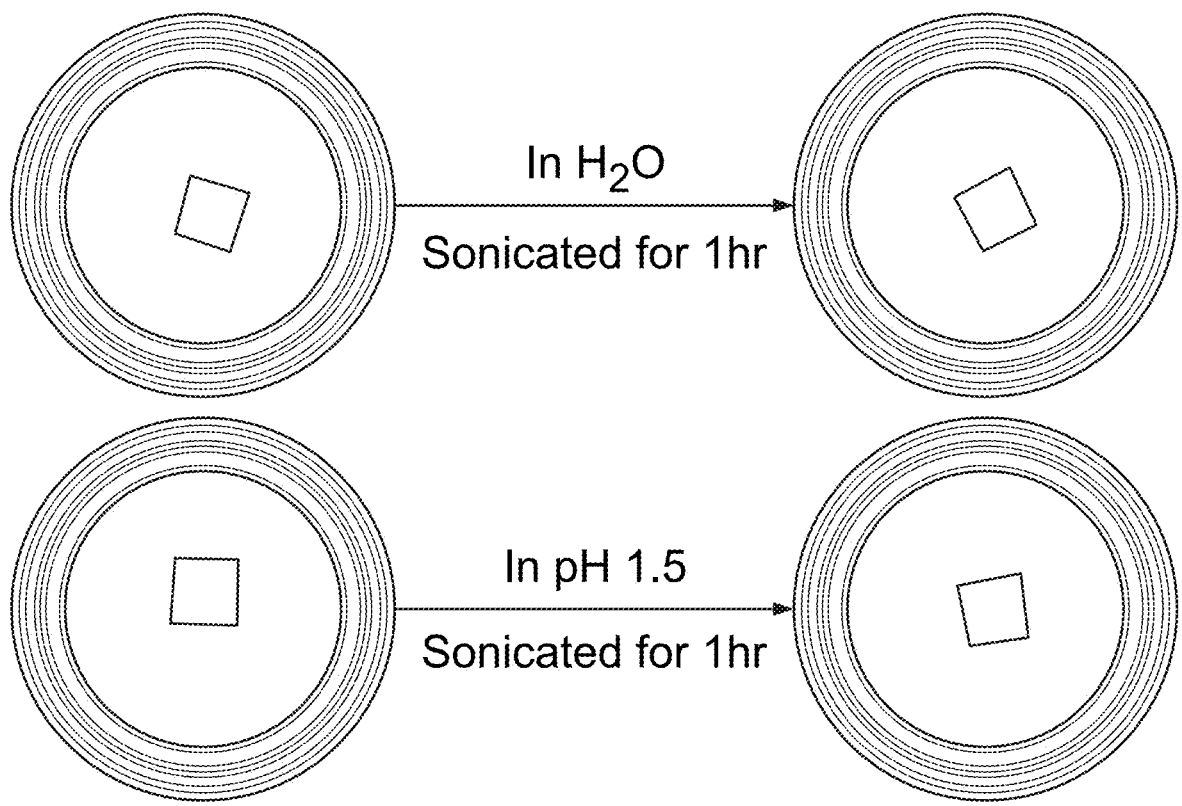
FIG. 7 is an exemplary embodiment of a photograph of the stability of an RGO/BNC:BNC film in accordance with the present disclosure.
Figure 8:
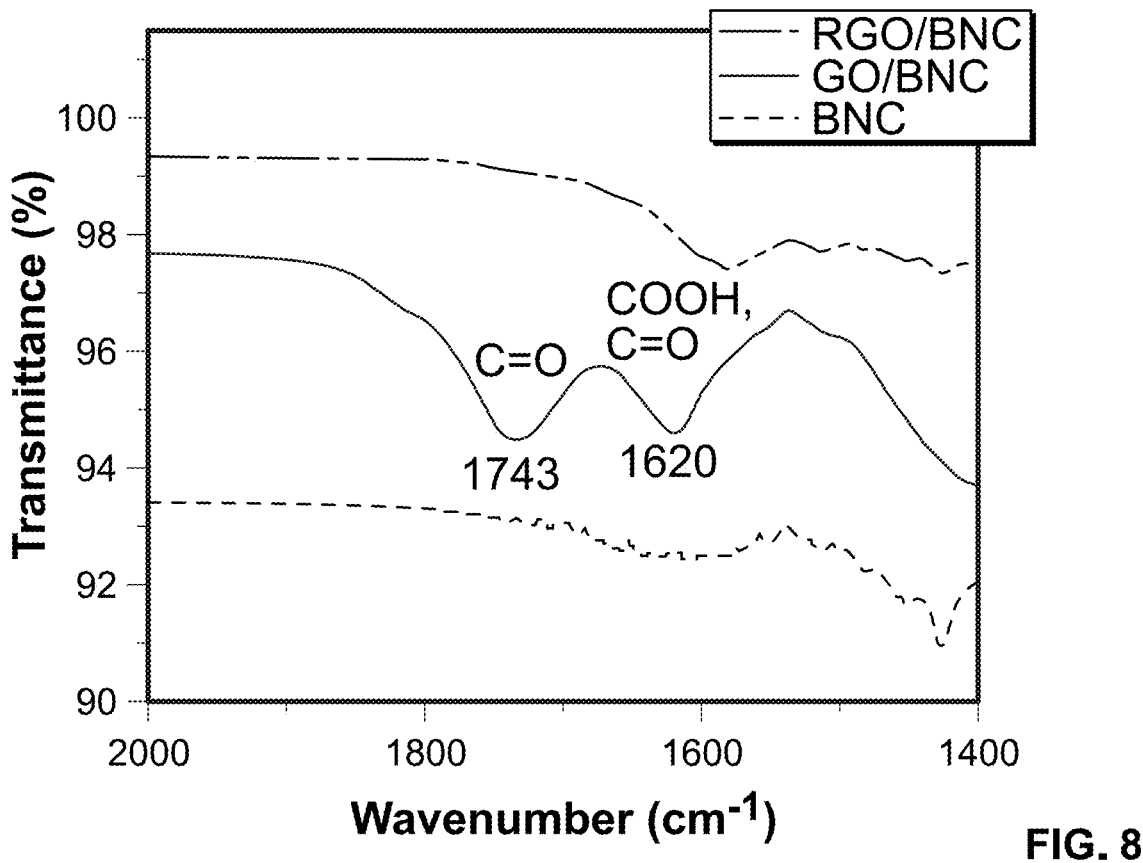
FIG. 8 is an exemplary embodiment of FTIR spectra of RGO/BNC, GO/BNC and BNC dry films in accordance with the present disclosure.
Figure 9A:
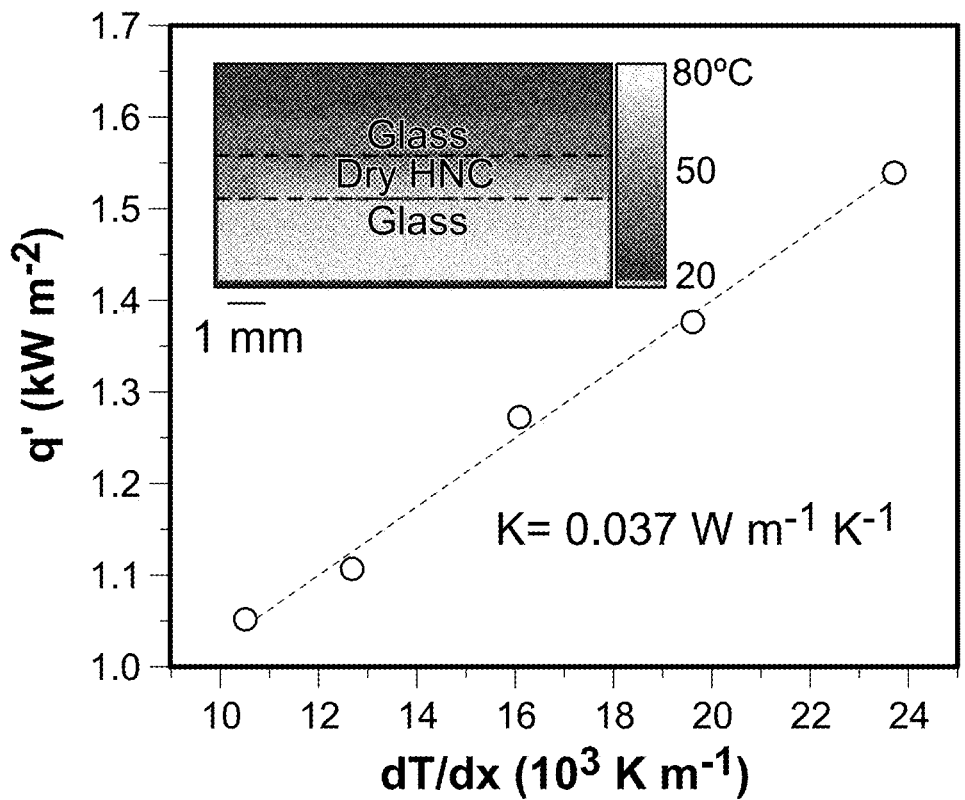
FIG. 9A is an exemplary embodiment of the thermal conductivity of a dry BNC film in accordance with the present disclosure.
Figure 9B:
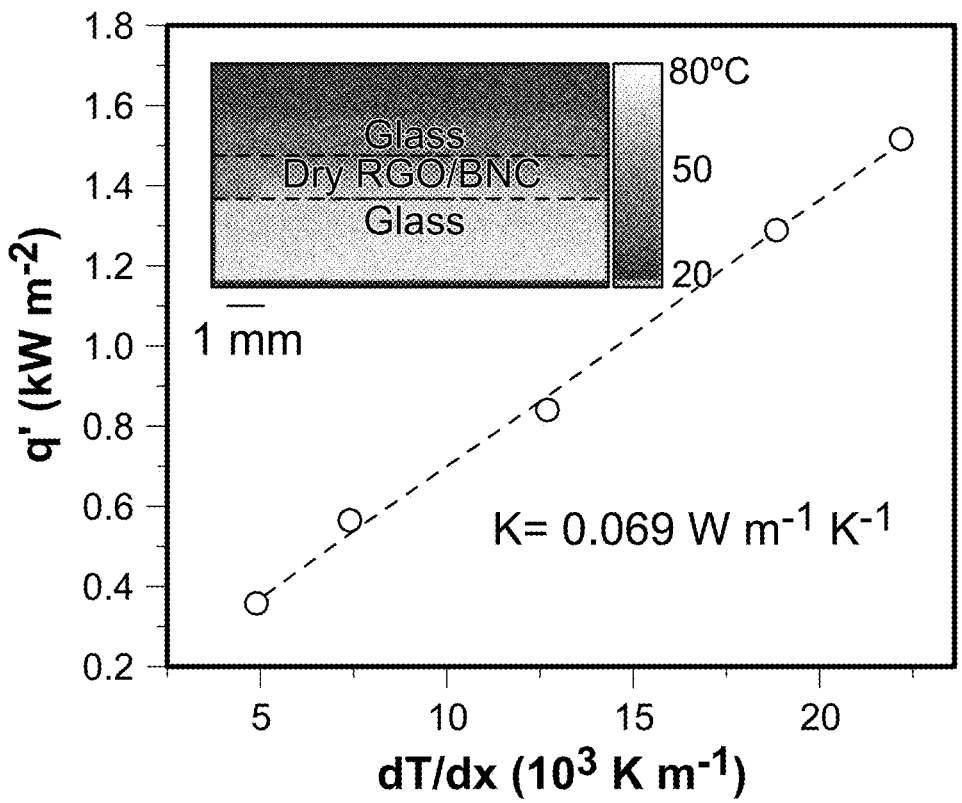
FIG. 9B is an exemplary embodiment of the thermal conductivity of an RGO/BNC foam in accordance with the present disclosure.

After harvesting the hydrogel comprising BNC and GO, the composition was subjected to a high temperature base wash to remove residual oxidative debris from the graphene oxide flakes. The composition changed from a clear brown suspension to a black aggregate confirming that chemical modification had occurred. The sample was analyzed using X-ray photoelectron spectroscopy (XPS) and Fourier Transform Infrared Spectroscopy (FTIR), and the results are shown in FIGS. 3C and 3D and FIG. 8.

Example 4: Thermal Conductivity Measurements of Wet/Dry RGO/BNC Aerogel and Bare BNC The thermal conductivities of the wet/dry RGO/BNC aerogel and the BNC aerogel were measured by sandwiching the materials between two glass microscope slides. The sandwich was placed between a hot plate and a glass slide with ice on top. The temperature distribution along the thickness was monitored using an IR camera (ICI 7320 USB camera). The emissivity coefficient of glass slide and sample to be 0.9 to obtain the temperature distribution. The Fourier equation was used to calculate the thermal conductivity of each sample:

$$q' = K \frac{\Delta T}{\Delta X}$$

Since the thermal conductivity (K) is known for glass slides (1.05 W/m·K was used), the heat flux (q') per unit area was calculated. Assuming the samples and the glass slides were experiencing the same heat flux, the thermal conductivity of the samples was calculated.

Example 5: Solar-Steam-Generation Experiment

A 1 cm×1 cm two layer aerogel with a thickness of around 21 mm was floated on water in a plastic cuvette with dimensions of 12.5 mm (W)×12.5 mm (D)×49 mm (H). The solar beam from a solar simulator (Newport AM1.5) was concentrated using a magnifying lens and illuminated onto the floating aerogel. The power density of the solar beam at the sample surface was controlled to be 10 kW/m$^2$. Each sample was illuminated for 15 min and the weight loss over the entire duration was recorded. The temperature was measured using an IR camera and the weight change from evaporation was measured using an electronic mass balance with an accuracy of 0.1 mg. The steam was generated at 100° C. under 10 kW/m$^2$ illumination. The evaporation efficiency (η) is given by:

$$\eta = \frac{mh_{LV}}{l}$$

where m is the evaporation rate, $h_{LV}$ is the total enthalpy of sensible heat (294 J/g, from 30 to 100° C. with a specific heat of 4.2 J·g/K and phase change of liquid to water (2257 J/g), and l is the incident laser power density. FIGS. 10B and 10C graph the temperature increase and the mass of water evaporated as a function of time.

Example 6. Preparation of Wood-GO Composite

Graphene oxide was synthesized using the method reported by Tour. The wood-GO composite was prepared by drop casting an aqueous GO solution (0.3 wt %) on the surface of the radially-cut wood and set aside for the GO solution to naturally dry.

Material Characterization

Scanning electron microscopy (SEM) images were obtained on a FEI Nova NanoSEM 2300 at an acceleration voltage of 10 kV. AFM images were obtained using Dimension 3000 (Bruker Inc.) in light tapping mode. The Raman spectra were obtained using a Renishaw inVia confocal Raman spectrometer mounted on a Leica microscope with a 50π objective and a 514 nm wavelength laser as an excitation source. Absorption spectra were collected using a Shimadzu UV-1800 UV-VIS spectrophotometer. XPS spectra were obtained using a Physical Electronics 5000 VersaProbe II Scanning ESCA (XPS) Microprobe.

Thermal Conductivity Measurements

The thermal conductivity of wood in the dry and wet state was measured by sandwiching the wood between two glass slides. The sandwich structure was placed on a hot plate with ice on the top side of glass. The temperature distribution along the cross-section of the sandwich structure was monitored using an IR camera (ICI 7320 P-Series). The Fourier equation was used to calculate the thermal conductivity using Equation (1):

$$q' = K\frac{\Delta T}{\Delta X} \quad \text{Equation (1)}$$

where q' is heat flux per unit area, K is thermal conductivity of glass (1.05 W/m·K), $\Delta T$ is temperature difference, $\Delta X$ is distance difference. The calculation of thermal conductivity was based on the assumptions that the sample and the glass slides were experiencing the same heat flux, and the emissivity coefficient of sample and glass slide was 0.9.

Example 7. Steam Generation Measurements

The temperature change and weight loss from evaporation of water for wood-GO, wood and water were measured under the irradiation of 808 nm laser at a power density of 5 kW/m$^2$ or simulated solar illumination (Newport AM1.5) at a power density of 12 kW/m$^2$. In the case of solar illumination, the solar beam was concentrated using a magnifying lens and illuminated onto the surface of floating sample. The temperature was measured using an IR camera and the weight loss from evaporation was measurement using an electronic microbalance with an accuracy of 0.0001 g. A 1 cm×1 cm GO-coated wood with a thickness of 3 mm was floated on the surface of water in a plastic cuvette with dimensions of 12.5 mm (W)×12.5 mm (D)×45 mm (H). The evaporation efficiency was calculated as described herein.

Example 8. Preparation of a PDA/BNC Aerogel

*Gluconacetobacter hansenii* (ATCC®53582) was cultured in test tubes containing 16 mL of #1765 medium at 30° C. under shaking at 250 μm. The #1765 medium is composed of 2% (w/v) glucose, 0.5% (w/v) yeast extract, 0.5% (w/v) peptone, 0.27% (w/v) disodium phosphate, and 0.5% (w/v) citric acid. Polydopamine (PDA) particles were prepared using a method reported by Lu and co-workers. To synthesize PDA particles with the size of 1 μm, ammonia solution (NH$_4$OH, 0.14 mL, 28-30%) was mixed with 31.5 mL of nanopure water (~18 MΩ·cm) and 14 mL of ethanol and the above mixture was shaken for 30 minutes. Dopamine hydrochloride solution (3.5 mL, 0.05 g/mL) was added into the above solution and then transferred to a petri dish. After 30 hours of mild shaking at room temperature, the PDA particles were collected by centrifugation (7000 μm, 20 min) and washed with water for three times and dispersed in nanopure water (40 mL). Bacterial culture solution (3 mL, incubated 3 days) was added to #1765 medium (15 mL) to make a total 18 mL bacterial growth solution. The solution was subsequently transferred to a petri dish (diameter: 6 cm) and incubated at room temperature without disturbance. After 5 days, a thick BNC hydrogel (~4 mm) was obtained. PDA particle solution described above (40 mL) was centrifuged and dispersed in bacterial growth medium (7 mL) and was then added on top of the thick BNC hydrogel. After 12 h, PDA particles formed on the BNC hydrogel and excess medium was removed. After another 12 h, a thin layer of PDA/BNC (~100 μm) was formed on top of the prior thick BNC hydrogel. The bilayered hydrogel was then harvested and washed in boiling water for 2 hours, then dialyzed in nanopure water for one day. The purified PDA/BNC bilayer was then freeze-dried overnight. For PDA/BNC with bigger size, above procedure were simply scaled up and performed in bigger containers.

Microstructure Characterization Methods:

Scanning electron microscope (SEM) images were obtained using a FEI Nova 2300 Field Emission SEM. Transmission electron microscope (TEM) images were obtained using a JEOL JEM-2100F field emission microscopy. Dynamic light scattering (DLS) measurements were performed using Malvern Zetasizer (Nano ZS). Shimadzu UV-1800 spectrophotometer was employed for obtaining UV-vis extinction spectra and transmittance spectra. Reflectance spectra were obtained using a CRAIC micro spectrophotometer (QDI 302) coupled to a Leica optical microscope (DM 4000M) with 20× objective in the range of 450-800 nm with 10 accumulations and 100 ms exposure time in reflection mode. Raman spectra were obtained using a Renishaw inVia confocal Raman spectrometer mounted on a Leica microscope with 20× objective and 785 nm wavelength diode laser as an illumination source. Thermogravimetric analysis (TGA) was performed using TA Instruments Q5000 IR Thermogravimetric Analyzer in air (at rate of 5° C. min-1).

Thermal Conductivity Measurements of Wet/Dry PDA/BNC:

The thermal conductivities of wet/dry PDA/BNC was determined using the procedure described in Example 4 above. The emissivity coefficient of a glass slide and a sample was assumed to be 0.9 to obtain the temperature distribution.

Solar Steam Generation Experiment

A circular bilayer of PDA/BNC with 3 cm diameter and 2.1 mm thickness was floated on water in a 100-ml beaker. The solar beam from a solar simulator (Newport 66921 Arc Lamp) was directly or concentrated using a magnifying lens illuminated onto the PDA/BNC. The power density of the solar beam on the sample surface was controlled to be 1 and 3 kW/m². Each sample was illuminated for 45 min and the weight loss over the entire duration was recorded. For the cycling experiments, a 1 cm×1 cm sample with 4 mm thickness floating on water in a plastic cuvette with dimensions of 12.5 mm (W)×12.5 mm (D)×49 mm (H) was used. The power density of the solar beam at the sample surface for cycling was controlled to be 7 kW/m² (7 sun) for 15 min illumination duration. The temperature was measured using an IR camera and the weight change from evaporation was measured using an electronic mass balance with an accuracy of 0.1 mg. It is assumed that the steam was generated at 100° C. The evaporation efficiency (η) was calculated using the equation in Example 5, wherein $h_{LV}$ is the total enthalpy of sensible heat (294 J/g, from 25° C. to 100° C. with specific heat 4.2 J/g·K) and phase change of liquid to water (2256 J/g), and I is the incident illumination power density.

Example 9. Preparation and Testing of RGO/BNC Membranes

Fabrication of RGO/BNC Membranes

*Gluconacetobacter hansenii* (ATCC53582) was employed to synthesize the cellulose nanofibers. To produce a dense bacterial suspension, the bacteria were cultured in test tubes containing 16 mL of #1765 medium at 30° C. for 3 days under shaking at 250 μm. The #1765 growth medium is composed of 2% (w/v) glucose, 0.5% (w/v) yeast extract, 0.5% (w/v) peptone, 0.27% (w/v) disodium phosphate, and 0.5% (w/v) citric acid. To synthesize GO, an oxidation process was employed.

For in situ incorporation of GO sheets in a BNC membrane, GO solution (150 mL of 0.0725 wt %) was sonicated (2 h), centrifuged, redispersed in #1765 medium, and then centrifuged again to concentrate a wet mixture of GO and medium after the supernatant was decanted. The densely cultured *Gluconacetobacter hansenii* suspension was added to the GO/medium wet mixture, making a total of 150 mL with 0.0725 wt % GO contents. The solution was subsequently transferred to a Pyrex glassware dish (18 cm×18 cm) and incubated at room temperature without disturbance. After 2 days, a thin hydrogel of GO/BNC had formed, and it was harvested from the bakeware for cleaning. To remove the residual bacteria and growth medium, the hydrogel was boiled in 2.5 L of 0.1 M NaOH aqueous solution for 2 h. The obtained RGO/BNC hydrogel was then dialyzed in deionized water for 1 day. The purified RGO/BNC hydrogel was dried to obtain an RGO/BNC membrane. Test results showed that the size and contents of GO in membranes and membrane thickness affected the water flux and solute rejection of RGO/BNC membranes. The specific GO concentration (0.0725 wt %), employed for preparing RGO/BNC membranes, provided the best flux performance and good solute rejection.

Microstructure Characterization and Property Measurements

Scanning electron microscopy (SEM, FEI Nova 2300 Field Emission SEM at an accelerating voltage of 10 kV) provided micron-scale images of RGO/BNC and pristine BNC. Atomic force microscopy (AFM) images were obtained for determining the thickness of GO flakes, using a Dimension 3000 (Bruker Inc.) instrument in light tapping mode. To investigate the relative oxygen and carbon ratio of GO and RGO flakes, carbon 1s peak was analyzed by X-ray photoelectron spectroscopy (XPS, a Physical Electronics 5000 VersaProbe II Scanning ESCA Microprobe). The pore size distribution of RGO/BNC membranes was measured by the Brunauer-Emmett-Teller (BET) method using an Autosorb-1C (AX1C-MP-LP) at 298 K.

Stability Tests of RGO/BNC Membranes

To study the stability of the RGO/BNC membrane, the membranes were placed in Petri dishes filled with solutions at pH 4, 7, and 9 and sonicated them for 5 h (483 W, 8892, Cole-Parmer). The pH values were chosen because they occur in many natural and engineering aqueous systems. Subsequently, the release of RGO from the membranes were quantified from the UV-vis absorbance spectra (Shimadzu UV-1800 spectrophotometer, 400 to 1000 nm) of the solutions. SEM was used to monitor the surface morphologies of the RGO/BNC membrane after sonication. To study the mass change of RGO/BNC membrane before and after sonication, thermogravimetric analysis (TGA) was performed using a TA Instruments Q5000 IR thermogravimetric analyzer in air at a rate of 5° C./min.

Because the GO membranes were frequently prepared by vacuum filtration, two types of control samples were made for comparison. First, a similar amount of base-washed RGO flakes was deposited on top of a BNC hydrogel, using the vacuum-assisted method, and dried to obtain a dry film. Second, BNC dispersions were premixed with GO solutions and were then filtered to make membranes. Both control membranes were subjected to the same aqueous stability tests as the RGO/BNC membrane.

Evaluation of Mass Transport of RGO/BNC Membranes

To estimate pore sizes of RGO/BNC membranes, the mass transport performance of RGO/BNC membranes was evaluated by using a side-by-side diffusion cell system. This cell system is particularly useful because it requires a much smaller sample volume (~10 mL) than that of benchtop cross-flow system (~15 L). An RGO/BNC membrane was first mounted between the two cells (Adams & Chittenden Scientific Glass, 5 mL volume). Then, ethanol and water were used to rinse the membrane several times to avoid subsequent air bubble formation.

To test diffusion-driven transport across an RGO/BNC membrane, 0.5 mM of rhodamine 6G (R6G, ~1 nm, 479 Da) and lysozyme (3.8-4 nm, 14 300 Da) were used. The observation of transport behaviors of two model solutes (R6G and lysozyme) helped to reveal the approximate pore size of RGO/BNC membrane, and consequently, determined the filtration type of RGO/BNC membranes. R6G is a cationic dye, and thus it is positively charged. The isoelectric points for lysozyme are 10.5, and its pH value at 0.5 mM concentration is 3.53, indicating that lysozyme was positively charged under the experimental conditions. The solute was introduced on the feed side, while the dialysate side was just DI water. Solutions in both cells were subjected to vigorous stirring to minimize concentration polarization effects close to the membrane. The diffusing concentrations of the solute were monitored in the wavelength range of 300-700 nm, using a Shimadzu UV-1800 spectrometer. The RGO/BNC membranes grown in independent batches were then utilized, and diffusion tests were conducted with three replicates.

Ultrafiltration Efficiency and Flux Tests

The water fluxes of the RGO/BNC membrane and commercial ultrafiltration membrane (YMGESP3001, GE) were tested using a benchtop cross-flow system, and then compared to those permeate fluxes. The commercial ultrafiltration membrane, used for comparison, was designed for pretreatment, dye reduction, and purification with 1000 Da cutoff sizes. The benchtop cross-flow system included a crossflow membrane cell (CF042D, Sterlitech Corp.) and a Hydracell pump (M03S, Wanner Engineering, Inc.).

During the measurement of the permeate flux, the pressure and the feed flux was set as 100 psi and 0.66 L/min, with 25° C. water. For the experiments, the RGO/BNC membranes utilized were grown in independent batches and the water fluxes were measured with three replicates. Furthermore, gold nanoparticles (AuNPs) with a diameter of around 5 nm were synthesized using the seed-mediated growth method, and their size distribution was determined from TEM images.

AuNP solutions were then filtered by RGO/BNC membranes, using the above cross-flow system under 100 psi. Before and after filtration, AuNP concentrations in filtration/permeate solutions were measured by UV-Vis spectrometry (400 to 1000 nm). The rejection rate (RR) was calculated using the equation below:

$$RR = \frac{E_f}{E_p} \times 100$$

where $E_f$ is the optical extinction of the feed solution and $E_p$ is the optical extinction of the permeate solution.

Photothermal and Bactericidal Performance of RGO/BNC Membranes Under Illumination The photothermal performance of the membranes was tested using a solar simulator (Newport 66921, Arc Lamp). Both the RGO/BNC membrane and BNC membrane were illuminated at a power density of 2.9 kW/m$^2$ for 180 s. The temperature map of the surface of both membranes under water was monitored by an IR camera (Ti 100, FLUKE).

To test bactericidal activity, MG 1655 E. coli was grown in Luria-Bertani liquid medium at 37° C. All cultures were in 125 mL baffled shake flasks (25 mL working volume, shaking at 225 μm). Cells in log phase (>108 live cells/mL) were harvested after 12 h of incubation and then used for bactericidal tests. A layer of MG 1655 E. coli biofilms was grown on the RGO/BNC and BNC membrane surfaces, and then exposed to simulated sunlight for 180 s at 2.9 kW/m$^2$. Before/after light illumination, the biofilms were exposed to fluorescent dyes (Molecular Probes Live/Dead Bacterial cell viability kit, Thermo Fisher Scientific) for 30 min and then imaged under a Leica microscope (DM 4000M, Leica microsystems) to identify live (blue fluorescent filter, 340-380 nm) and dead (green fluorescent filter, 450-490 nm) cells.

Results and Discussion

Characterization of the RGO/BNC Membranes

Figure 27A:
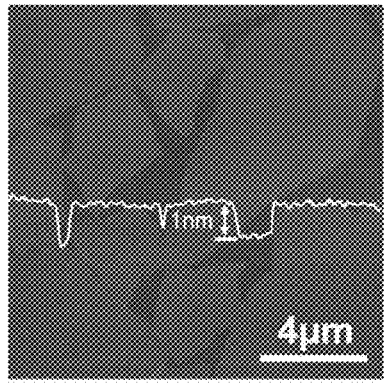
FIGS. 27A-27I are exemplary embodiments of the chemical composition and microstructure of RGO/BNC membranes in accordance with the present disclosure.

The RGO/BNC membranes were fabricated by in situ incorporation of GO flakes within the BNC network via bacteriamediated growth under aerobic and static conditions (FIGS. 26A and 26B). To determine the average thickness of synthesized GO flakes, they were deposited on a silicon substrate and measured with AFM. The thicknesses were ~1.0±0.2 nm, corresponding to a bilayer of GO (the thickness of a monolayer is ~0.7 nm) (FIG. 27A).

After washing, GO flakes were dispersed in broth solution with bacteria at an optimized concentration to achieve a desired BNC growth rate (FIG. 26A). The GO dispersed solution was left undisturbed under ambient conditions to obtain GO/BNC hydrogels. To remove bacteria and residual broth solution from in situ grown GO/BNC hydrogel, it was immersed in NaOH solution (0.1 M) at boiling temperature, which partially reduced the GO flakes. The cleaned RGO/BNC hydrogel was dried to obtain a large, robust RGO/BNC membrane (FIG. 26B).

Figure 27B:
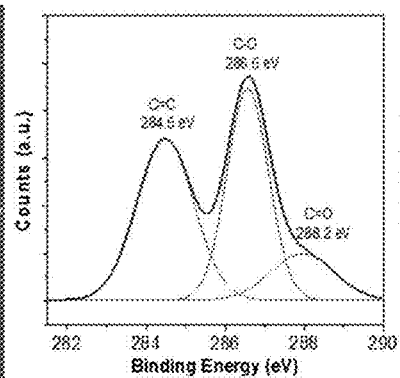
Figure 27C:
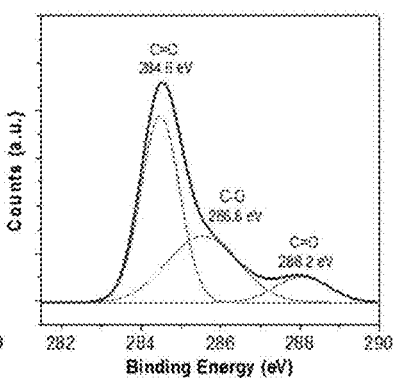

To understand the chemical reduction of GO during cleaning, GO flakes were added to a boiling 0.1 M NaOH solution, which turned uniformly distributed GO particles into black aggregated particles, indicating the partial reduction and restacking of the RGO. To confirm the reduction of GO after exposure to the basic solution, X-ray photoelectron spectroscopy (XPS) was utilized (FIGS. 27B and 27C). The high resolution is spectra of carbon were obtained and were deconvoluted into three peaks, corresponding one sp$^2$ domain (C—C with a binding energy of 284.6 eV) and two oxidized sp$^3$ domains (C—O with a binding energy of 286.6 eV, and C—O with a binding energy of 288.2 eV).

The relative carbon and oxygen ratio was calculated based on the peak area, and this ratio was utilized to estimate the reduction extent of GO. For synthesized GO, the C/O ratio was 1.7, indicating that ~58% of the GO was oxidized (FIG. 27B). After an extensive base wash, the C/O ratio increased to 4.6, indicating that ~37% of the oxygen functional groups were reduced (FIG. 27C). This result confirms that base washing to kill residual bacteria also reduced GO flakes in the BNC matrix.

Figure 27D:
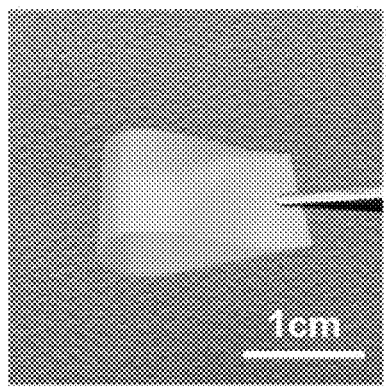
Figure 27E:
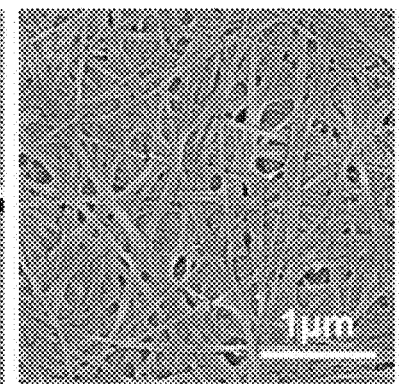
Figure 27F:
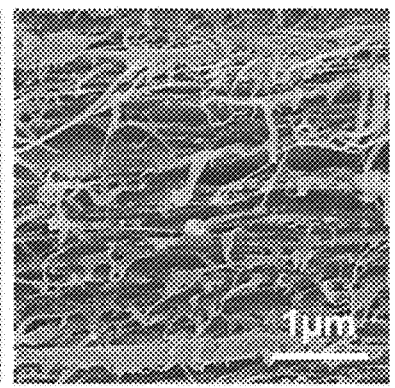

In the absence of GO flakes, bacteria-mediated growth results in a white, translucent BNC membrane with outstanding flexibility and mechanical strength (FIG. 27D). Because bacteria-mediated synthesis of nanocellulose requires oxygen, a dense network of nanocellulose fibers (20-100 nm in diameter) forms near the air/liquid interface, where abundant oxygen is available (FIG. 27E). As the oxygen diffuses deeper into the medium, the first dense layer guided the formation of subsequent BNC layers, which then stacked together to form a 3D BNC network. Due to this "layer-by-layer" formation, the cellulose nanofibrils are preferentially oriented parallel to the surface (i.e., normal to the thickness) of the membrane, which results in denser physical entanglements of the cellulose nanofibers parallel to the surface (FIG. 27F).

Figure 27G:
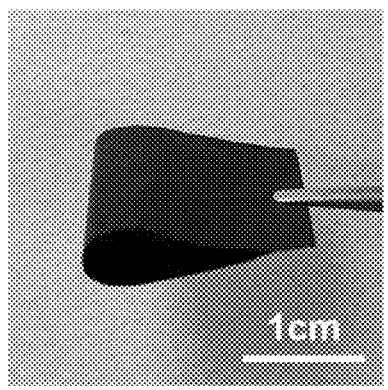
Figure 27H:
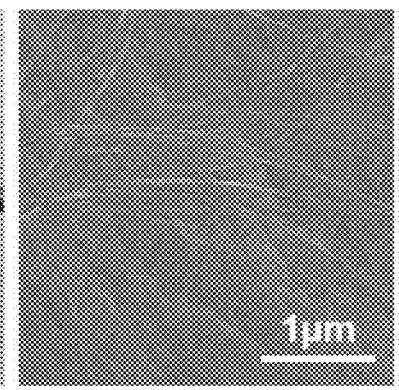
Figure 27I:
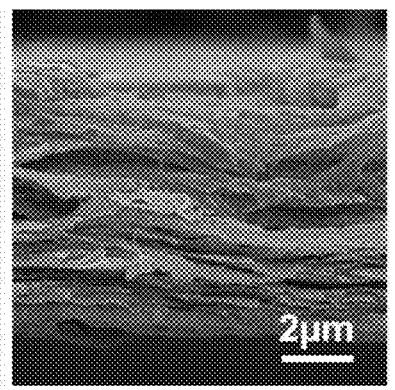

To form RGO/BNC membranes as shown in FIG. 27G, GO flakes were added during in situ growth, and a subsequent base washing process was conducted. Compared to pristine BNC membrane, the RGO/BNC membrane is smoother and less fibrillar (FIG. 27H), due to the presence of 2D RGO sheets. For quantitative comparisons, nanoscale surface roughness of BNC and RGO/BNC membranes was measured by AFM, and the results showed the surface roughness of 32.4±9.46 nm and 25.0±14.2 nm, respectively, indicating the rougher surface of BNC membranes. Cross-sectional SEM image showed that the membrane was ~8 μm thick (FIG. 27I). The image also showed the embedded RGO flakes between BNC layers due to the "layered" formation of BNC, starting from the liquid/air interface as described above. Because the hydrophilicity is an important property to influence the water flux of membrane, the contact angles of RGO/BNC and BNC membranes were measured. Due to reduction of hydrophilic GO flakes during inevitable cleaning process, the RGO/BNC membrane showed a higher contact angle (65±130) than that of BNC membrane (23±50).

Mechanical and Chemical Stability of the RGO/BNC Membranes

To investigate the mechanical and chemical stability of the RGO/BNC membranes, the membranes were exposed to ultrasonic agitation for 5 h in solutions at pH 4, 7, and 9.

Even after this vigorous mechanical agitation at environmentally relevant pH conditions, the RGO/BNC membranes did not exhibit any signs of disintegration or loss of RGO flakes (FIG. 28A and its inset). This result was further supported by SEM images of the membrane surface, which did not show a discernible change in the morphology after sonication (FIG. 28B).

Then, to evaluate the thermal stability of the RGO/BNC membrane, TGA was conducted. The RGO/BNC membrane showed a first mass loss of ~2 wt % at ~100° C., due to the loss of absorbed water. A second mass loss of ~3 wt % at ~200° C. was attributed to the decomposition of functional groups of GO. A third mass loss of ~46 wt % began at 280° C. and was due to the degradation of cellulose. A fourth mass loss (~49 wt %) at 390° C. was attributable to the continued decomposition of residual cellulose and sublimation or burning of damaged graphitic regions in RGO flakes and BNC. On the basis of the mass loss profiles of the RGO/BNC membrane, RGO flakes, and pristine BNC membrane, the mass loading of RGO in RGO/BNC was calculated to be ~45 wt %, and it indicated excellent thermal stability of the RGO/BNC membrane up to 200° C. The RGO/BNC membrane after ultrasonic treatment also showed an identical mass loss profile (FIG. 28C), implying that the embedded RGO flakes within the BNC matrix remained intact.

GO-based membranes have been extensively investigated in the past several years. Most of these membranes were fabricated by vacuum filtration of GO flakes onto a supporting membrane, but this coating method always leaves doubt about its long-term aqueous stability. Here, the mechanical stability of in situ embedded RGO/BNC was compared with that of an RGO-coated BNC membrane prepared by depositing RGO particles (base-washed) on top of a BNC membrane using vacuum filtration. After 5 h of ultrasonic agitation in solutions at pH 4, 7, and 9, the RGO particles had disintegrated completely, and the solution exhibited broad absorbance, a feature of RGO flakes in solution (FIG. 28D). This disintegration was further confirmed by surface SEM images and quantified by TGA. After sonication, the membrane prepared through vacuum filtration showed an initial mass loss (~5%) at 100° C., attributed to absorbed water, and the decomposition of cellulose at ~280° C. (~63%) and at ~340° C. (~32%). All of these findings indicated the absence of RGO flakes (FIG. 28F).

Conventional GO-based membranes rely on hydrogen bonding or metal ion incorporation for mechanical stability. However, mechanical agitation during water filtration or cleaning procedures, as well as pH variations in the feedwater, can compromise the mechanical stability of these membranes. In contrast, in situ RGO/BNC membranes are robust because during the BNC growth, plate-like GO particles are physically locked into the layered BNC matrices, which provides its excellent mechanical and chemical stability. Moreover, intensive vortexing has been employed to wash used in situ RGO/BNC membranes, and did not cause any discernible damage on these membranes, indicating the mechanical stability under the mechanical stress. This finding further indicates the durability of the in situ RGO/BNC membrane during potential cleaning process.

Mass Transport Performance and Water Flux Tests

To probe the diffusive transport capability of small molecules across the RGO/BNC membranes, a two-cell setup was employed (FIG. 29A) and tested it with 0.5 mM of two model solutes, having different sizes and molecular weights: rhodamine 6G (R6G, ~1 nm, 479 Da) and lysozyme (3.8-4 nm, 14 300 Da). Because ultrafilters have pore sizes between 1 and 100 nm, and thus remove contaminants via a size exclusion mechanism, these two different solutes helped to determine the pore size and filtration capability of RGO/BNC membranes.

A UV-Vis spectrometer was used to monitor the concentration of model solutes from the feed side to the permeate side. For a pristine BNC membrane, all two solutes rapidly diffused through because the BNC fiber network is composed of microscale pores even if the nanofibers are densely packed (FIG. 29B). By contrast, the addition of graphene oxide flakes within the matrix completely blocked the diffusion of lysozyme (3.8-4 nm), although R6G (~1 nm) passed through. These results are in accordance with the BET measurements which indicate the pore size of the RGO/BNC membrane is around 2.2 nm (radius), which falls into the range of ultrafiltration membranes. Moreover, the unique mass transport properties of GO-based membranes originate from the nanocapillary network formed by lamellar stacking of GO, and the mass-transport behavior can be adjusted by tuning functional groups or inserting external species with desired dimensions. The presence of bacterial cellulose nanofibers between RGO flakes lead to an overall tortuous network of pores in the membrane, even though no visible pores are seen in an SEM image of the surface of the RGO/BNC membranes.

To further demonstrate the potential of the novel RGO/BNC membrane for an ultrafiltration system, flux tests and particle rejection tests were performed using size-controlled gold nanoparticles (AuNPs) via a benchtop cross-flow system (FIG. 29C). For particle rejection tests, spherical gold nanoparticles with diameters of 5.15±0.4 nm were synthesized using the seed-mediated method. The prepared AuNPs showed a very narrow size distribution (RSD <8%), which made the particle rejection study accurate. The particle rejection rates were calculated by measuring the UV-Vis extinction spectra of solutions before/after filtration through the RGO/BNC membranes (FIG. 29D). This result indicated that AuNPs of 5 nm diameter were ~100% rejected (inset of FIG. 29D). In the same way, a rejection test was also performed for a commercial ultrafiltration membrane (pore size of around 1.66 nm), which also showed ~100% rejection for 5 nm gold nanoparticles.

Under 100 psi, the RGO/BNC membranes showed higher water fluxes than a commercial ultrafiltration (UF) membrane. Because the pore size for both membrane types belongs to the range between UF and nanofiltration (NF), water flux was intentionally tested at a higher operating pressure than the usual operating pressure for UF (7.3-73 psi). Over a 5 h-long flux test after stabilization, the water flux of the RGO/BNC membrane was found to be 52.6±2.5 L/m$^2$·h, and that of the commercial ultrafiltration membrane was 21.6±0.8 L/m$^2$·h (FIG. 29E). Importantly, the RGO/BNC membrane withstood an operating pressure as high as 100 psi without any supporting membrane. This performance emphasized the remarkable mechanical strength of RGO/BNC, considering that most of the GO-based membranes reported require a support membrane or a carefully designed apparatus due to their limited mechanical strength.

Photothermal and Bactericidal Performance Under Illumination

Next, the photothermal and bactericidal ability of the RGO/BNC membrane was examined using a Newport 66921 Arc Lamp with a power density of 2.9 kW/m$^2$. IR imaging was used to monitor the temperature profile of the RGO/BNC membrane in an aqueous environment during illumination (FIG. 30B). The reduction of GO flakes during inevitable sample preparation (cleaning) process provides the benefits for better photothermal conversion efficiency because the abundant delocalized π electrons in conjugated sp²-bonded carbon create the closely spaced energy levels.

Upon illumination, the temperatures of the RGO/BNC membrane rapidly increased from room temperature (26° C.) to ~60° C. (FIG. 30C). Specifically, the temperature rapidly increased during the first 20 s after the onset of irradiation and remained constant over the entire duration (120 s). In comparison, the pristine BNC membranes showed only a small temperature increase (3° C.). The large rise in temperature was caused by the broad optical absorption of many RGO flakes arranged within the BNC matrix. Once light was absorbed by the RGO flakes, they immediately generated heat, which then dissipated to the surrounding water and BNC. Due to the decrease of thermal radiation along the distance between IR camera and surface (~30 cm), the temperature profile obtained from the IR camera underestimated the actual temperature at the surface of the RGO/BNC membrane.

Therefore, biological species were exposed to a temperature higher than ~60° C. To test whether the heat generated by light exposure would affect the mass transport and water flux performance of the RGO/BNC membrane, BET and water flux tests were performed before and after long duration of light exposure (2.9 kW/m²). Both the pore size distribution and the water flux performance of RGO/BNC membrane remained stable with minor variation after light exposure.

To test the bactericidal ability, the RGO/BNC membrane was covered with *E. coli* bacteria, and then light was shined on the membrane surface. After light illumination, the bacteria on the membrane surface were stained by a live/dead cell viability assay. As a result, before irradiation, both RGO/BNC and pristine BNC membranes showed substantial and well distributed green fluorescence, corresponding to live bacteria, and no sign of red fluorescence, indicating the absence of dead bacteria (FIG. 30D). After irradiation (2.9 kW/m²) for 180 s, the bacteria on the RGO/BNC membrane exhibited predominantly red fluorescence (dead bacteria) and a complete visible absence of green fluorescence. However, the *E. coli*-covered pristine BNC membrane exhibited green fluorescence corresponding to live bacteria, even after irradiation (FIG. 30E).

The SEM images showed morphological changes and leakage of bacteria, indicating that the high temperature at the RGO/BNC membrane had disrupted the cell walls and cell membranes (FIGS. 30F and 30G). Before light irradiation, live *E. coli* bacteria on an RGO/BNC membrane showed a rod-like structure, while after irradiation they were significantly shrunken and wrinkled. Because the cell walls of *E. coli* are known to deteriorate near 70° C., this change implied that upon illumination, the surface of the RGO/BNC membrane had rapidly heated to above 70° C. and killed bacteria within a short time (180 s). *E. coli* bacteria on an RGO/BNC membrane without illumination showed only green fluorescence signals even after 1 h exposure, indicating the bactericidal activity of RGO/BNC membrane only occurs upon light illumination. Here, the excellent bactericidal performance of the RGO/BNC membrane in harvesting light was demonstrated, and this capability makes the RGO/BNC membrane highly attractive for energy-saving and environmentally friendly water purification applications.

When introducing elements of the present disclosure or embodiments thereof, the articles "a," "an," "the," and "said" are intended to mean that there are one or more of the elements. The terms "comprising," including," and "having" are intended to be inclusive and mean that there may be additional elements other than the listed elements.

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

What is claimed is:

1. A method for the preparation of a bilayered biofilm comprising nanocellulose and a nanomaterial, the method comprising:
   providing a bacterial culture of *Gluconacetobacter hansenii* in a growth media;
   incubating the bacterial culture and the nanomaterial until a first biofilm layer forms;
   adding additional growth media on top of the first biofilm layer, said additional growth media comprising the bacterial culture; and,
   incubating the bacterial culture until a second biofilm layer forms thereby forming a bilayered biofilm,
   wherein one of the bacterial cultures in growth media further comprises a nanomaterial.

2. The method of claim 1, further comprising one or more of the following:
   harvesting the bilayered biofilm,
   washing the bilayered biofilm,
   dialyzing the bilayered biofilm in water, or
   freeze-drying the bilayered biofilm.

3. The method of claim 1 wherein the nanomaterial is selected from the group consisting of graphene oxide, reduced graphene oxide, molybdenum disulfide, polydopamine, functionalized multiwalled carbon nanotubes and combinations thereof.

4. The method of claim 1, wherein the nanomaterial is polydopamine.

5. The method of claim 1, wherein the nanomaterial is selected from the group consisting of graphene oxide, reduced graphene oxide and a combination thereof.

* * * * *